US012296016B2

(12) United States Patent
Lencer et al.

(10) Patent No.: US 12,296,016 B2
(45) Date of Patent: *May 13, 2025

(54) CERAMIDE-LIKE LIPID-BASED DELIVERY VEHICLES AND USES THEREOF

(71) Applicant: Children's Medical Center Corporation, Boston, MA (US)

(72) Inventors: Wayne I. Lencer, Jamaica Plain, MA (US); Daniel J F Chinnapen, Quincy, MA (US); Richard I. Duclos, Quincy, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,578

(22) Filed: Aug. 11, 2023

(65) Prior Publication Data

US 2024/0042042 A1 Feb. 8, 2024

Related U.S. Application Data

(63) Continuation of application No. 17/046,753, filed as application No. PCT/US2019/027281 on Apr. 12, 2019, now Pat. No. 11,771,771.

(60) Provisional application No. 62/656,474, filed on Apr. 12, 2018.

(51) Int. Cl.
A61K 47/54 (2017.01)
A61K 9/16 (2006.01)
A61K 31/7105 (2006.01)
A61K 47/65 (2017.01)
A61K 39/00 (2006.01)

(52) U.S. Cl.
CPC .......... *A61K 47/543* (2017.08); *A61K 9/1617* (2013.01); *A61K 31/7105* (2013.01); *A61K 47/65* (2017.08); *A61K 39/00* (2013.01)

(58) Field of Classification Search
CPC .... A61K 47/543; A61K 47/65; A61K 9/1617; A61K 31/7105
See application file for complete search history.

(56) References Cited

U.S. PATENT DOCUMENTS

| | | | |
|---|---|---|---|
| 4,610,868 | A | 9/1986 | Fountain et al. |
| 5,149,794 | A | 9/1992 | Yatvin et al. |
| 5,366,963 | A | 11/1994 | Ladisch |
| 5,846,951 | A | 12/1998 | Gregoriadis |
| 5,965,519 | A | 10/1999 | Yatvin et al. |
| 6,193,997 | B1 | 2/2001 | Modi |
| 9,457,097 | B2 | 10/2016 | Lencer et al. |
| 10,765,757 | B2 | 9/2020 | Lencer et al. |
| 10,806,793 | B2 | 10/2020 | Lencer et al. |
| 11,559,568 | B2 | 1/2023 | Lencer et al. |
| 11,771,771 | B2 * | 10/2023 | Lencer ................. A61K 9/1617 424/450 |
| 2003/0114415 | A1 | 6/2003 | Wurtman et al. |
| 2005/0281772 | A1 | 12/2005 | Bromley et al. |
| 2006/0052316 | A1 | 3/2006 | Porcelli |
| 2006/0171956 | A1 | 8/2006 | Bareholz et al. |
| 2007/0231344 | A1 | 10/2007 | Leadbetter et al. |
| 2008/0064645 | A1 | 3/2008 | Pagano et al. |
| 2008/0299168 | A1 | 12/2008 | Dadey et al. |
| 2010/0092425 | A1 | 4/2010 | Von Andrian et al. |
| 2012/0252727 | A1 | 10/2012 | Lencer et al. |
| 2012/0277158 | A1 | 11/2012 | Castaigne et al. |
| 2014/0171372 | A1 | 6/2014 | Lalezari et al. |
| 2016/0266097 | A1 | 9/2016 | Gagnon |
| 2017/0095563 | A1 | 4/2017 | Lencer et al. |
| 2018/0133332 | A1 | 5/2018 | Lencer et al. |
| 2018/0333499 | A9 | 11/2018 | Lencer et al. |
| 2020/0289619 | A1 | 9/2020 | Lencer et al. |
| 2021/0338823 | A9 | 11/2021 | Lencer et al. |
| 2023/0132279 | A1 | 4/2023 | Lencer et al. |

FOREIGN PATENT DOCUMENTS

| | | |
|---|---|---|
| EP | 1972349 A1 | 9/2008 |
| JP | H07-509227 A | 10/1995 |
| JP | 2016-509013 A | 3/2016 |

(Continued)

OTHER PUBLICATIONS

Ahn et al., Induction of apoptosis by sphingosine, sphinganine, and C(2)-ceramide in human colon cancer cells, but not by C(2)-dihydroceramide. Anticancer Res. Jul. 2010;30(7):2881-4. Erratum in: Anticancer Res. Sep. 2010;30(9):3851.

Albrecht et al., Synthesis and mass spectrometric characterization of digoxigenin and biotin labeled ganglioside GM1 and their uptake by and metabolism in cultured cells. Chem Phys Lipids. Mar. 28, 1997;86(1):37-50. doi: 10.1016/s0009-3084(97)02658-3.

(Continued)

*Primary Examiner* — Michael P Cohen
(74) *Attorney, Agent, or Firm* — Wolf, Greenfield & Sacks, P.C.

(57) ABSTRACT

Provided herein, in some aspects, are delivery vehicles comprising a ceramide and an agent to be delivered attached to the ceramide. In some embodiments, the ceramide does not comprise a fatty acid (i.e., is a sphingosine). In some embodiments, the ceramide comprises a fatty acid. In some embodiments, the ceramide is a glycoceramide. In some embodiments, the agent is attached to the ceramide covalently (e.g., via a linker). In some embodiments, the agent to be delivered is a therapeutic agent. The ceramide is able to deliver the agent to a cell or to a cellular compartment, as well as across the musical barrier. In some embodiments, agents delivered using the ceramide described herein exhibit longer half-life, compared to agents delivered alone. Methods of delivering a therapeutic agent to a subject for treating a disease using the ceramide delivery vehicle are also provided.

23 Claims, 25 Drawing Sheets

(56) References Cited

FOREIGN PATENT DOCUMENTS

| WO | WO 94/01138 A1 | 1/1994 |
|---|---|---|
| WO | WO 99/15201 A1 | 4/1999 |
| WO | WO 99/43356 A1 | 9/1999 |
| WO | WO 03/106474 A2 | 12/2003 |
| WO | WO 2005/097199 A1 | 10/2005 |
| WO | WO 08/111916 A1 | 9/2008 |
| WO | WO 2010/027479 A2 | 3/2010 |
| WO | WO 2013/150532 A1 | 10/2013 |
| WO | WO 2016/118697 A9 | 7/2016 |
| WO | WO 2018/031933 A2 | 2/2018 |

OTHER PUBLICATIONS

Allan, D., Lipid metabolic changes caused by short-chain ceramides and the connection with apoptosis. Biochem J. Feb. 1, 2000;345 Pt 3(Pt 3):603-10. PMID: 10642519;.

Ashkenazi et al., Sphingopeptides: dihydrosphingosine-based fusion inhibitors against wild-type and enfuvirtide-resistant HIV-1. FASEB J. Nov. 2012;26(11):4628-36. doi: 10.1096/fj.12-215111. Epub Aug. 7, 2012.

Augé et al., The sphingomyelin-ceramide signaling pathway is involved in oxidized low density lipoprotein-induced cell proliferation. J Biol Chem. Aug. 9, 1996;271(32):19251-5. doi: 10.1074/jbc.271.32.19251.

Backhed et al., Host-bacterial mutualism in the human intestine. Science. Mar. 25, 2005;307(5717):1915-20.

Bagai et al., Reconstituted Sendai virus envelopes as biological carriers: dual role of F protein in binding and fusion with liver cells. Biochim Biophys Acta. Oct. 10, 1993;1152(1):15-25.

Ballou et al., Interleukin-1-mediated PGE2 production and sphingomyelin metabolism. Evidence for the regulation of cyclooxygenase gene expression by sphingosine and ceramide. J Biol Chem. Oct. 5, 1992;267(28):20044-50.

Brocca et al., Conformation of the oligosaccharide chain of G(M1) ganglioside in a carbohydrate-enriched surface. Biophys J. Jan. 1998;74(1):309-18. doi: 10.1016/S0006-3495(98)77788-4.

Brown, Lipid rafts, detergent-resistant membranes, and raft targeting signals. Physiology (Bethesda). Dec. 2006;21:430-9.

Chigorno et al., Formation of a cytosolic ganglioside-protein complex following administration of photoreactive ganglioside GM1 to human fibroblasts in culture. FEBS Lett. Apr. 24, 1990;263(2):329-31.

Chiricozzi et al., GM1 Ganglioside Is a Key Factor in Maintaining the Mammalian Neuronal Functions Avoiding Neurodegeneration. Int J Mol Sci. Jan. 29, 2020;21(3):868. doi: 10.3390/ijms21030868.

Dickinson et al., Bidirectional FcRn-dependent IgG transport in a polarized human intestinal epithelial cell line. J Clin Invest. Oct. 1999; 104(7):903-11.

Dickinson et al., Ca2+-dependent calmodulin binding to FcRn affects immunoglobulin G transport in the transcytotic pathway. Mol Biol Cell. Jan. 2008;19(1):414-23. Epub Nov. 14, 2007.

Dobrowsky et al., Ceramide activates heterotrimeric protein phosphatase 2A. J Biol Chem. Jul. 25, 1993;268(21):15523-30.

Doyle et al., Glucagon-like peptide-1. Recent Prog Horm Res. 2001;56:377-99.

Franchini et al., Synthesis of a fluorescent sulfatide for the study of CD1 antigen binding properties. Eur J Org Chem. Dec. 2004;2004(23):4755-61.

Gao et al. Potentiation of Cationic Liposome-Meidated Gene Delivery by Polycations. Biochemistry 1996, 35, 1027-1036. (Year: 1996).

Gidwani et al., Disruption of lipid order by short-chain ceramides correlates with inhibition of phospholipase D and downstream signaling by FcepsilonRI. J Cell Sci. Aug. 1, 2003;116(Pt 15):3177-87. doi: 10.1242/jcs.00621.

Gudz et al., Direct inhibition of mitochondrial respiratory chain complex III by cell-permeable ceramide. J Biol Chem. Sep. 26, 1997;272(39):24154-8. doi: 10.1074/jbc.272.39.24154.

Hanna et al., A novel pathway for tumor necrosis factor-alpha and ceramide signaling involving sequential activation of tyrosine kinase, p21(ras), and phosphatidylinositol 3-kinase. J Biol Chem. Apr. 30, 1999;274(18):12722-9. doi: 10.1074/jbc.274.18.12722.

Holowka et al., Short chain ceramides disrupt immunoreceptor signaling by inhibiting segregation of Lo from Ld Plasma membrane components. Biol Open. Sep. 27, 2018;7(9):bio034702. doi: 10.1242/bio.034702.

Hölttä-Vuori et al., Modulation of cellular cholesterol transport and homeostasis by Rab11. Mol Biol Cell. Sep. 2002;13(9):3107-22. doi: 10.1091/mbc.e02-01-0025.

Hsu et al., Ceramide inhibits lipopolysaccharide-mediated nitric oxide synthase and cyclooxygenase-2 induction in macrophages: effects on protein kinases and transcription factors. J Immunol. May 1, 2001;166(9):5388-97. doi: 10.4049/jimmunol.166.9.5388.

Khazanov et al., Physicochemical and biological characterization of ceramide-containing liposomes: paving the way to ceramide therapeutic application. Langmuir. Jun. 1, 2008;24(13):6965-80. doi: 10.1021/la800207z. Epub May 30, 2008.

Kieffer et al., The glucagon-like peptides. Endocr Rev. Dec. 1999;20(6):876-913.

Kolesnick et al., Compartmentalization of ceramide signaling: physical foundations and biological effects. J Cell Physiol. Sep. 2000;184(3):285-300. doi: 10.1002/1097-4652(200009)184:3<285::AID-JCP2>3.0.CO;2-3.

Kondo et al., Control of ceramide-induced apoptosis by IGF-1: involvement of PI-3 kinase, caspase-3 and catalase. Cell Death Differ. Jun. 2002;9(6):682-92. doi: 10.1038/sj.cdd.4401019.

Ledeen et al., The multi-tasked life of GM1 ganglioside, a true factotum of nature. Trends Biochem Sci. Jul. 2015;40(7):407-18. doi: 10.1016/j.tibs.2015.04.005. Epub May 26, 2015.

Lencer et al., The intracellular voyage of cholera toxin: going retro. Trends Biochem Sci. Dec. 2003;28(12):639-45.

Lencer et al., Transcytosis of cholera toxin subunits across model human intestinal epithelia. Proc Natl Acad Sci U S A. Oct. 24, 1995;92(22):10094-8.

Liu et al., Trifluoromethyl Derivatization of the Ganglioside, GM1. Synthesis. 2010;11:1905-1908. doi: 10.1055/s-0029-1218777.

Lowthers et al., Differential sensitivity to short-chain ceramide analogues of human intestinal carcinoma cells grown in tumor spheroids versus monolayer culture. In Vitro Cell Dev Biol Anim. Sep.-Oct. 2003;39(8-9):340-2. doi: 10.1290/1543-706X(2003)039<0340:DSTSCA>2.0.CO;2.

Makiyama et al., Newly synthetic ceramide-1-phosphate analogs; their uptake, intracellular localization, and roles as an inhibitor of cytosolic phospholipase A(2)a and inducer of cell toxicity. Biochem Pharmacol. Nov. 1, 2010;80(9):1396-406. doi: 10.1016/j.bcp.2010.07.028. Epub Aug. 3, 2010.

Maxfield et al., Endocytic recycling. Nat Rev Mol Cell Biol. Feb. 2004;5(2):121-32.

Möbius et al., Gangliosides are transported from the plasma membrane to intralysosomal membranes as revealed by immuno-electron microscopy. Biosci Rep. Aug. 1999;19(4):307-16. doi: 10.1023/a:1020502525572.

Möbius et al., Intracellular distribution of a biotin-labeled ganglioside, GM1, by immunoelectron microscopy after endocytosis in fibroblasts. J Histochem Cytochem. Aug. 1999;47(8):1005-14. doi: 10.1177/002215549904700804.

Mukherjee et al., Endocytic sorting of lipid analogues differing solely in the chemistry of their hydrophobic tails. J Cell Biol. Mar. 22, 1999;144(6):1271-84.

Mukherjee et al., Role of membrane organization and membrane domains in endocytic lipid trafficking. Traffic. Mar. 2000;1(3):203-11.

Obeid et al., Programmed cell death induced by ceramide. Science. Mar. 19, 1993;259(5102):1769-71. doi: 10.1126/science.8456305.

Okazaki et al., Role of ceramide as a lipid mediator of 1 alpha,25-dihydroxyvitamin D3-induced HL-60 cell differentiation. J Biol Chem. Sep. 15, 1990;265(26):15823-31.

Orskov et al., Biological effects and metabolic rates of glucagonlike peptide-1 7-36 amide and glucagonlike peptide-1 7-37 in healthy subjects are indistinguishable. Diabetes. May 1993;42(5):658-61.

(56) References Cited

OTHER PUBLICATIONS

Panasiewicz et al., Preparation of Alexa Fluor 350-conjugated nonradioactive or 3H-labeled GM1 ganglioside derivatives with different ceramides. Anal Biochem. Feb. 1, 2009;385(1):168-70. Epub Oct. 2, 20081.

Pohl et al., Rapid transmembrane diffusion of ceramide and dihydroceramide spin-labelled analogues in the liquid ordered phase. Mol Membr Biol. Apr. 2009;26(3):194-204.

Polyakova et al., New GM1 Ganglioside Derivatives for Selective Single and Double Labelling of the Natural Glycosphingolipid Skeleton. Eur. J. Org. Chem. Oct. 2009;2009;30:5162-77. doi: 10.1002/ejoc.200900645. Epub Oct. 6, 2009.

Prioni et al., Interactions between gangliosides and proteins in the exoplasmic leaflet of neuronal plasma membranes: a study performed with a tritium-labeled GM1 derivative containing a photoactivable group linked to the oligosaccharide chain. Glycoconj J. 2004;21(8-9):461-70. doi: 10.1007/s10719-004-5536-4.

Rakoff-Nahoum et al., Innate immune recognition of the indigenous microbial flora. Mucosal Immunol. Nov. 2008;1 Suppl 1:S10-4. doi: 10.1038/mi.2008.49.

Rockendorf et al., Synthesis of a fluorescent ganglioside GM1 derivative and screening of a synthetic peptide library fir GM1 binding sequence motifs. Bioconjugate Chemistry. 2003; 18:573-578.

Saslowsky et al., Ganglioside GM1-mediated transcytosis of cholera toxin bypasses the retrograde pathway and depends on the structure of the ceramide domain. J Biol Chem. Sep. 6, 2013;288(36):25804-25809. doi: 10.1074/jbc.M113.474957. Epub Jul. 24, 2013.

Shang et al., Toll-like receptor signaling in small intestinal epithelium promotes B-cell recruitment and IgA production in lamina propria. Gastroenterology. Aug. 2008;135(2):529-38. doi: 10.1053/j.gastro.2008.04.020. Epub Apr. 22, 2008.

Simon et al., Membrane-destabilizing properties of C2-ceramide may be responsible for its ability to inhibit platelet aggregation. Biochemistry. Feb. 17, 1998;37(7):2059-69. doi: 10.1021/bi9710636.

Simons et al., Model systems, lipid rafts, and cell membranes. Annu Rev Biophys Biomol Struct. 2004;33:269-95.

Simons et al., Cholesterol, lipid rafts, and disease. J Clin Invest. Sep. 2002;110(5):597-603.

Sonnino et al., Aggregation properties of semisynthetic GM1 ganglioside (II3Neu5AcGgOse4Cer) containing an acetyl group as acyl moiety. Chem Phys Lipids. Nov. 1990;56(1):49-57. doi: 10.1016/0009-3084(90)90087-8.

Sonnino et al., Preparation of GM1 ganglioside molecular species having homogeneous fatty acid and long chain base moieties. J Lipid Res. Feb. 1985;26(2):248-57.

Sot et al., Molecular associations and surface-active properties of short- and long-N-acyl chain ceramides. Biochim Biophys Acta. Jun. 1, 2005;1711(1):12-9. doi: 10.1016/j.bbamem.2005.02.014. Epub Mar. 16, 2005.

Spiekermann et al., Receptor-mediated immunoglobulin G transport across mucosal barriers in adult life: functional expression of FcRn in the mammalian lung. J Exp Med. Aug. 5, 2002;196(3):303-10.

Stover et al., Liposomal delivery enhances short-chain ceramide-induced apoptosis of breast cancer cells. J Pharmacol Exp Ther. Nov. 2003;307(2):468-75. Epub Sep. 15, 2003.

Sturm et al., Structure-function studies on positions 17, 18, and 21 replacement analogues of glucagon: the importance of charged residues and salt bridges in glucagon biological activity. J Med Chem. Jul. 16, 1998;41(15):2693-700.

Te Welscher et al., Unsaturated glycoceramides as molecular carriers for mucosal drug delivery of GLP-1. J Control Release. Feb. 10, 2014;175:72-8. doi: 10.1016/j.jconrel.2013.12.013. Epub Dec. 23, 2013.

Tsai et al., Protein disulfide isomerase acts as a redox-dependent chaperone to unfold cholera toxin. Cell. Mar. 23, 2001;104(6):937-48.

Van Genderen et al., Differential targeting of glucosylceramide and galactosylceramide analogues after synthesis but not during transcytosis in Madin-Darby canine kidney cells. J Cell Biol. Nov. 1995;131(3):645-54.

Vavrova et al., Synthetic ceramide analogues as skin permeation enhancers: structure-activity relationships. Bioorganic & Medicinal Chemistry. 2003;11:5381-5390.

Vodovozova, Photoaffinity labeling and its application in structural biology. Biochemistry (Mosc). Jan. 2007;72(1):1-20. doi: 10.1134/s0006297907010014.

Welsher et al., Unsaturated glycoceramides as molecular carriers for mucosal drug delivery of GLP-1. J Control Release. Feb. 10, 2014;175:72-8.

Xiao et al., Biological activities of glucagon-like peptide-1 analogues in vitro and in vivo. Biochemistry. Mar. 6, 2001;40(9):2860-9.

Zheng et al., Ceramides and other bioactive sphingolipid backbones in health and disease: lipidomic analysis, metabolism and roles in membrane structure, dynamics, signaling and autophagy. Biochim Biophys Acta. Dec. 2006;1758(12):1864-84. doi: 10.1016/j.bbamem.2006.08.009. Epub Aug. 22, 2006.

Zhu et al., C2-ceramide induces cell death and protective autophagy in head and neck squamous cell carcinoma cells. Int J Mol Sci. Feb. 21, 2014;15(2):3336-55. doi: 10.3390/ijms15023336.

Sueyoshi et al., Apoptosis of Neuro2a cells induced by lysosphingolipids with naturally occurring stereochemical configurations. J Lipid Res. Aug. 2001;42(8):1197-202.

\* cited by examiner

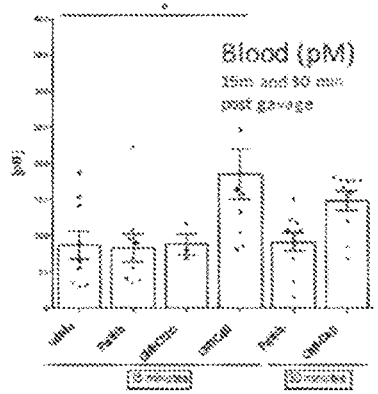 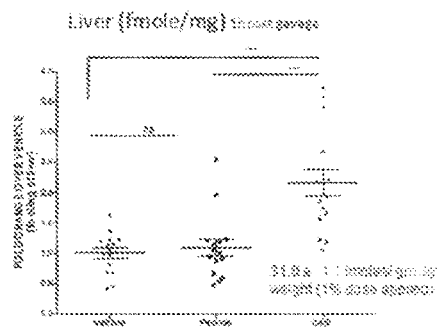
FIG. 4A　　　　　　　　　FIG. 4B
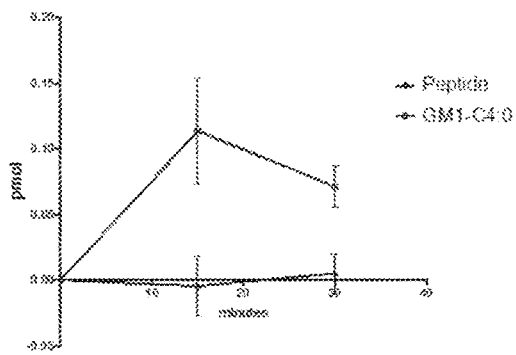 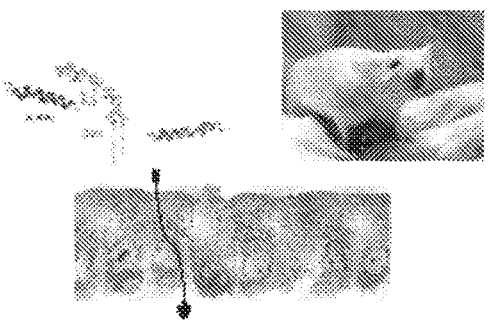
FIG. 4C　　　　　　　　　FIG. 4D
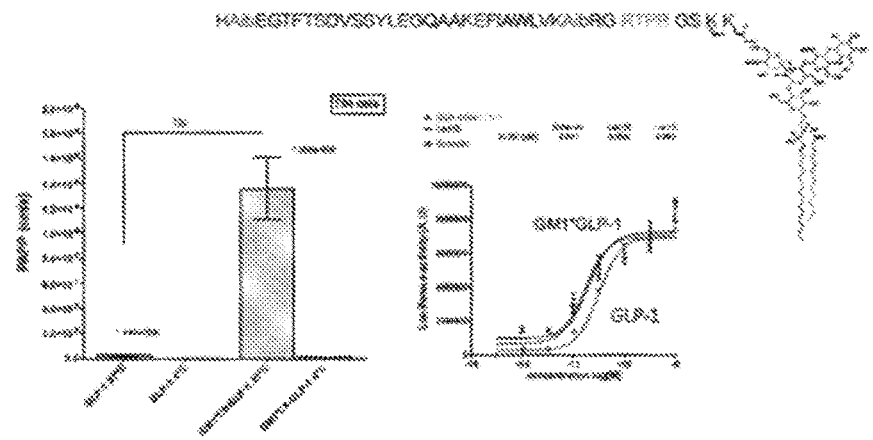
FIG. 5A　　　　　　　　　FIG. 5B human microvascular
endothelial cells

CERAMIDE-LIKE LIPID-BASED DELIVERY VEHICLES AND USES THEREOF

RELATED APPLICATIONS

This application is a Continuation of U.S. application Ser. No. 17/046,753, filed Oct. 9, 2020, which is a National Stage filing under 35 U.S.C. § 371 of International Application No. PCT/US2019/027281, filed Apr. 12, 2019, which claims the benefit under 35 U.S.C. § 119 (e) to U.S. Provisional Application No. 62/656,474, filed Apr. 12, 2018, and entitled "CERAMIDE-LIKE LIPID-BASED DELIVERY VEHICLES AND USES THEREOF," the entire contents of each of which are incorporated herein by reference.

FEDERALLY SPONSORED RESEARCH

This invention was made with government support under Grant Nos. DK048106, DK104868, DK090603, and DK034854, awarded by the National Institutes of Health. The Government has certain rights in the invention.

BACKGROUND

One of the major challenges for applying protein and peptide biologics to clinical medicine is the lack of rational and efficient methods to circumvent epithelial and endothelial cell barriers separating large molecules from target tissues. In the case of epithelial cells lining mucosal surfaces, the pathway for absorption of large solutes (e.g., biologics) is by transcytosis—a process of transcellular endosome trafficking that connects one surface of the cell with the other.

SUMMARY

The present disclosure, in some aspects, relates to using ceramides (e.g., naturally occurring ceramides and ceramide analogs or ceramide-like molecules) as delivery vehicles to deliver agents (e.g., therapeutic agents) into cells or across epithelial and/or endothelial barriers. The sorting of the agents via different endocytic pathways relate to the structure of the ceramide. In some embodiments, the ceramides are used to deliver agents to a targeted site, e.g., to treat a disease in a subject.

Some aspects of the present disclosure provide delivery vehicles comprising a ceramide and an agent to be delivered, wherein the ceramide: (a) does not contain a fatty acid; or (b) comprises a fatty acid of C1-C28; and wherein the agent is attached to the ceramide.

In some embodiments, the ceramide is a ceramide analog. In some embodiments, the ceramide analog is selected from the group consisting of: 2-hydroxy-ceramide, diene-deoxy-ceramide, dihydroceramide, phytosphingosine, dihydroceramide phosphate, o-acyl-ceramide, ceramide phosphate, sphinganine, and methyl-sphingosine. In some embodiments, the ceramide analog comprises an unsaturated hydrocarbon chain attached to ornithine, tyrosine, glycine, leucine, proline, glutamine, or taurine.

In some embodiments, the ceramide is a glycoceramide. In some embodiments, the glycoceramide comprises a sugar selected from the group consisting of: glucose, galactose, fructose, and GalNac. In some embodiments, the agent to be delivered is attached to the sugar.

In some embodiments, no sugar is attached to the ceramide. In some embodiments, the ceramide is a sphingosine. In some embodiments, the agent to be delivered is attached to the primary hydroxyl group of the ceramide. In some embodiments, the agent to be delivered is attached to the secondary hydroxyl group of the ceramide.

In some embodiments, the agent to be delivered is attached to the ceramide via a linker. In some embodiments, the linker is a pseudo-glycopeptide linker. In some embodiments, the pseudo-glycopeptide linker comprises at least one sugar attached to an amino acid backbone. In some embodiments, the at least one sugar is selected from the group consisting of: glucose, galactose, and N-Acetylgalactosamine. In some embodiments, the at least one sugar is attached to the amino acid backbone via a serine side chain.

In some embodiments, the linker is a cleavable linker. In some embodiments, the cleavable linker comprises an ester linkage. In some embodiments, the cleavable linker is a peptide linker comprising an ester linkage. In some embodiments, the cleavable linker comprises a cleavage motif for an endosomal protease. In some embodiments, the endosomal protease is furin or matriptase. In some embodiments, the linker is a disulfide linkage.

In some embodiments, the ceramide comprises a fatty acid of C1-C6. In some embodiments, the ceramide comprises a fatty acid of C4. In some embodiments, the ceramide comprises a fatty acid of C6. In some embodiments, the fatty acid has no double bonds between two carbon atoms. In some embodiments, the ceramide comprises a fatty acid of C7-C28. In some embodiments, the ceramide comprises a fatty acid of C8. In some embodiments, the fatty acid has at least one cis double bonds between two carbon atoms. In some embodiments, the at least one cis double bond is in C1-C18 region. In some embodiments, the fatty acid comprises a chemical moiety in C1-C18 region. In some embodiments, the ceramide does not comprise a fatty acid.

In some embodiments, the ceramide comprises a fatty acid of C1-C12.

In some embodiments, the agent to be delivered is selected from the group consisting of proteins, peptides, nucleic acids, polysaccharides and carbohydrates, lipids, glycoproteins, small molecules, synthetic organic and inorganic drugs exerting a biological effect when administered to a subject, and combinations thereof. In some embodiments, the agent to be delivered is a therapeutic agent. In some embodiments, the therapeutic agent is an anti-inflammatory agent, a vaccine antigen, a small molecule drug, an anti-cancer drug or chemotherapeutic drug, a clotting factor, a hormone, a steroid, a cytokine, an antibiotic, an antibody, a ScFv, a nanobody, a vaccine adjuvant, or a drug for the treatment of a cardiovascular disease, an infectious disease, an autoimmune disease, allergy, a blood disorder, a metabolic disorder, a skin disease, an eye disease, a lysosomal storage disease or a neurological disease.

In some embodiments, the agent to be delivered is a protein or a peptide. In some embodiments, the protein or peptide is a vaccine antigen. In some embodiments, the protein or peptide is an antibody, a ScFv, or a nanobody. In some embodiments, the protein or peptide is an enzyme. In some embodiments, the enzyme is a lysosomal replacement enzyme. In some embodiments, the protein or peptide is a hormone. In some embodiments, the protein or peptide is a neurotransmitter. In some embodiments, the protein or peptide is GLP-1, or a functional fragment thereof. In some embodiments, the protein or peptide is Exendin-4, or a functional fragment thereof. In some embodiments, the therapeutic agent comprises GLP-1 or a functional fragment thereof, and Exendin-4 or a functional fragment thereof. In some embodiments, the therapeutic agent comprises a ligand for a cell receptor. In some embodiments, the cell receptor is a growth factor receptor, a G-protein coupled receptor, or a toll-like receptor.

In some embodiments, the therapeutic agent is a nucleic acid.

Other aspects of the present disclosure provide ceramide-therapeutic agent complexes comprising a ceramide and an agent to be delivered, wherein the ceramide: (a) does not comprise a fatty acid; or (b) comprises a fatty acid of C1-C28; and wherein the agent is attached to the ceramide.

In some embodiments, the ceramide is a ceramide analog. In some embodiments, the ceramide analog is selected from the group consisting of: 2-hydroxy-ceramide, diene-deoxy-ceramide, dihydroceramide, phytosphingosine, dihydroceramide phosphate, o-acyl-ceramide, ceramide phosphate, sphinganine, and methyl-sphingosine. In some embodiments, the ceramide analog comprises an unsaturated hydrocarbon chain attached to ornithine, tyrosine, glycine, leucine, proline, glutamine, or taurine.

In some embodiments, the ceramide is a glycoceramide. In some embodiments, the glycoceramide comprises a sugar selected from the group consisting of: glucose, galactose, fructose, and GalNAc. In some embodiments, the agent to be delivered is attached to the sugar. In some embodiments, no sugar is attached to the ceramide. In some embodiments, the ceramide is a sphingosine. In some embodiments, the agent to be delivered is attached to the primary hydroxyl group of the ceramide. In some embodiments, the agent to be delivered is attached to the secondary hydroxyl group of the ceramide.

In some embodiments, the agent to be delivered is attached to the ceramide via a linker. In some embodiments, the linker is a pseudo-glycopeptide linker. In some embodiments, the pseudo-glycopeptide linker comprises at least one sugar attached to an amino acid backbone. In some embodiments, the at least one sugar is selected In some embodiments, the at least one sugar is attached to the amino acid backbone via a serine side chain.

In some embodiments, the linker is a cleavable linker. In some embodiments, the cleavable linker comprises an ester linkage. In some embodiments, the cleavable linker is a peptide linker comprising an ester linkage. In some embodiments, the cleavable linker comprises a cleavage motif for an endosomal protease. In some embodiments, the endosomal protease is furin or matriptase. In some embodiments, the linker is a disulfide linkage.

In some embodiments, the ceramide comprises a fatty acid of C1-C6. In some embodiments, the ceramide comprises a fatty acid of C4. In some embodiments, the ceramide comprises a fatty acid of C6. In some embodiments, the fatty acid has no double bonds between two carbon atoms. In some embodiments, the ceramide comprises a fatty acid of C7-C28. In some embodiments, the ceramide comprises a fatty acid of C8. In some embodiments, the fatty acid has at least one cis double bonds between two carbon atoms. In some embodiments, the at least one cis double bond is in C1-C18 region. In some embodiments, the fatty acid comprises a chemical moiety in C1-C18 region. In some embodiments, the ceramide does not comprise a fatty acid.

In some embodiments, the ceramide comprises a fatty acid of C1-C12.

In some embodiments, the therapeutic agent is selected from the group consisting of proteins, peptides, nucleic acids, polysaccharides and carbohydrates, lipids, glycoproteins, small molecules, synthetic organic and inorganic drugs exerting a biological effect when administered to a subject, and combinations thereof. In some embodiments, the therapeutic agent is an anti-inflammatory agent, a vaccine antigen, a small molecule drug, an anti-cancer drug or chemotherapeutic drug, a clotting factor, a hormone, a steroid, a cytokine, an antibiotic, an antibody, a ScFv, a nanobody, a vaccine adjuvant, or a drug for the treatment of cardiovascular disease, an infectious disease, an autoimmune disease, allergy, a blood disorder, a metabolic disorder, a skin disease, an eye disease, a lysosomal storage disease, or a neurological disease. In some embodiments, the therapeutic agent is a protein or a peptide. In some embodiments, the protein or peptide is a vaccine antigen. In some embodiments, the protein or peptide is an antibody, a ScFv, or a nanobody. In some embodiments, the protein or peptide is an enzyme. In some embodiments, the enzyme is a lysosomal storage enzyme. In some embodiments, the protein or peptide is a hormone. In some embodiments, the protein or peptide is a neurotransmitter. In some embodiments, the protein or peptide is GLP-1, or a functional fragment thereof. In some embodiments, the protein or peptide is Exendin-4, or a functional fragment thereof. In some embodiments, the therapeutic agent comprises GLP-1 or a functional fragment thereof, and Exendin-4 or a functional fragment thereof. In some embodiments, the therapeutic agent comprises a ligand for a cell receptor. In some embodiments, the cell receptor is a growth factor receptor, a G-protein coupled receptor, or a toll-like receptor.

In some embodiments, the therapeutic agent is a nucleic acid.

Further provided herein are compositions comprising the delivery vehicle, or the ceramide-therapeutic agent complex described herein. In some embodiments, the composition further comprises a pharmaceutically acceptable carrier.

Other aspects of the present disclosure provide methods of delivering an agent into a cell, across a mucosal surface, or across an endothelial barrier the method comprising contacting the delivery vehicle the ceramide-therapeutic complex with the cell, the mucosal surface, or the endothelial lumenal surface, under conditions appropriate for uptake of the delivery vehicle or the agent into the cell or absorption of the delivery vehicle or the agent across the mucosal surface or endothelial barrier.

Other aspects of the present disclosure provide methods of delivering an agent into a cell or across a mucosal or endothelial surface, the method comprising contacting the composition described herein with the cell, the mucosal surface, or the endothelial lumenal surface, under conditions appropriate for uptake of the composition or the agent into the cell or absorption of the composition or the agent across the mucosal surface or the endothelial barrier.

Other aspects of the present disclosure provide methods of delivering an agent into a cells, across a mucosal surface, or across an endothelial barrier in a subject, the method comprising administering to the subject the delivery vehicle, the ceramide-therapeutic agent, or the composition described herein.

Other aspects of the present disclosure provide methods of enhancing the half-life of an agent in a subject, the method comprising administering to the subject the delivery vehicle, the ceramide-therapeutic agent, or the composition described herein.

Other aspects of the present disclosure provide methods of treating a disease or condition in a subject in need thereof, the method comprising administering to the subject an effective amount of the delivery vehicle, the ceramide-therapeutic agent, or the composition described herein, wherein the effective amount is an amount sufficient to ameliorate/reduce the extent to which the disease or condition occurs in the subject. In some embodiments, the delivery vehicle, the ceramide-therapeutic agent complex, or the composition is administered parenterally. In some embodiments, the delivery vehicle, the ceramide-therapeutic agent complex, or the composition is administered intravenously, intramuscularly, intradermally, subcutaneously, intrathecally, intraperitoneally, intraarterially, intracardiacally, intraosseously, intraocularly, intravitreally, intranasally or intrapleurally. In some embodiments, the delivery vehicle, the ceramide-therapeutic agent complex, or the composition is administered nonparenterally. In some embodiments, the delivery vehicle, the ceramide-therapeutic agent complex, or the composition is administered orally, sublingually, topically, rectally, or via inhalation. For delivery across tight endothelial barriers, in some embodiments, the ceramide-therapeutic agent complex is delivered intravenously, intramuscularly, or subcutaneously.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 4A-4D. In vivo mouse studies. Absorption from intestine into blood for GM-fusion molecules 15 and 30 minutes after gastric gavage (FIG. 4A), and absorption from intestine into liver for GM-fusion molecules 1 hour after gastric gavage (FIG. 4B) are shown. Peptide alone was not absorbed. Time course for absorption into blood was plotted (FIG. 4C). N=3 independent studies. Schematic of the GM-fusion molecule is shown in FIG. 4D.

FIGS. 5A-5B. Transcytosis of the incretin hormone GLP-1 when fused to the GM1 transport vehicles across model epithelial barriers in vitro. GLP-1 incretin function is retained after fusion to the oligosaccharide domain of GM1 (FIG. 5B) (half-log loss in activity). When tested in vitro, GLP-1 was transported across epithelial barriers by the short-chain GM1-species nearly 100-fold above that observed for the peptide alone (FIG. 5A).

(FIG. 13A) Control peptide. (FIG. 13B) Crude reaction of ceramide to peptide. (FIG. 13C) After purification. (FIG. 13D) Mass spectrometry analysis confirmed the presence of peptide linked to ceramide (2+ and 3+ charged species).

(FIG. 24A) N-acyloxyacyl-ornitine. (FIG. 24B) Cerilipin. (FIG. 24C) Brominated mololipids. R1, R2=C14 to C20 fatty acid. (FIG. 24D) iso-3-hydroxy heptadecanoic acid-containing lipid. (FIG. 24E) Lipstatin. (FIG. 24F) N-stearoyl proline. (FIG. 24G) Volicitin. (FIG. 24H) N-acyl Taurine.

(FIG. 25A) A schematic of endosomal sorting in human microvascular endothelial cells (HMECs). (FIG. 25B) Images HMECs incubated either with C16:0-GM1-peptide (top panels), or peptide alone (bottom panel). Cells were treated with 2 μM fluorescently green labeled compound for 1 hour for continuous uptake on coverslips, and imaged in the presence of Lysotracker-Red (red). The C16-GM1 lipid colocalized mostly to lysosomes (yellow puncta), whereas the peptide alone did not enter into cells. (FIG. 25C) C12-GM1 (green) was incubated for continuous uptake for 1 hour with HMEC cells and colocalized to lysosomes (yellow), in addition to plasma membrane localization, indicating that this lipid can be sorted both the recycling and lysosomal pathways. The merged image on the left is zoomed in and displayed as Merged, green, and red channels on the right. Scale bars=10 μm.

(FIG. 32A) Validation of the fusion molecule in mice. (FIG. 38B) Serum levels of intravenously administered GM1-peptide fusion or peptide alone 1 day after administration. (FIG. 32C) Serum levels of intravenously administered GM1-peptide fusion or peptide alone 1 day after administration.

DETAILED DESCRIPTION OF CERTAIN EMBODIMENTS

Figure 1:
FIG. 1. Schematic for trafficking pathway for delivery of peptide or protein drugs across tight epithelial and endothelial barriers.
Figure 2:
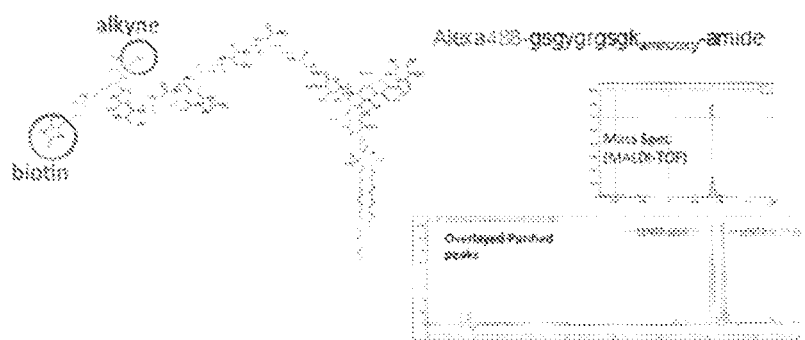
FIG. 2. Schematic of reporter peptide (amino acid sequence: GSGYGRGSGK, SEQ ID NO: 1) fused to the glycoceramide GM1.
Figure 3:
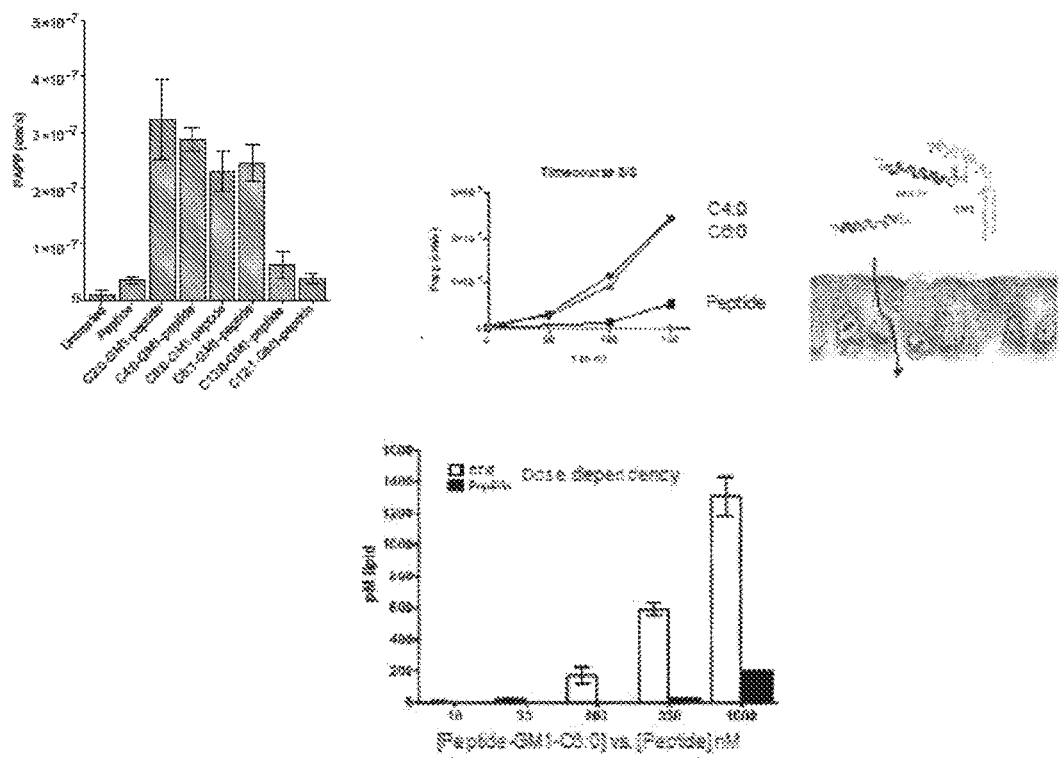
FIG. 3. Structure function studies on GM1 ceramide domain. Non-native GM1 species with amplified transcytosis across epithelial barriers in vitro were identified. Time course studies and dose dependency of fusion molecules compared to peptide alone are shown.
Figure 6:
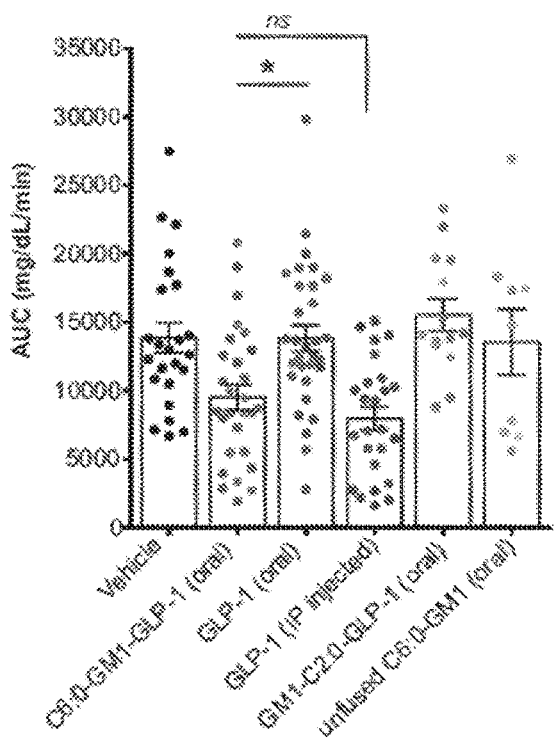
FIG. 6. In vivo intestinal absorption of GLP-1-GM1 fusion molecules delivered by gastric gavage (oral) to mice corrected serum glucose levels after glucose challenge (glucose tolerance test) at about the same dose administered by intraperitoneal injection (IP). N=6 independent experiments.

Delivery of biologically active molecules across tight mucosal epithelial barriers is a major challenge preventing application of most therapeutic peptides for oral drug delivery. The sorting endosome sorts cargo into four separate pathways: the lysosome pathway, the retrograde pathway to Golgi and ER, the recycling pathway back to the plasma membrane, and (in polarized cells like epithelial and endothelial cells) into the transcytotic pathway that connects one cell surface with the other, allowing for adsorption. The pathways are distinct and do not intersect with each other (e.g., as described in Saslowsky et al., J Biol Chem. Sep 6; 288(36):25804-9, incorporated herein by reference). It is possible that lipid sorting into these different pathways may be regulated by the molecular shape of the lipid allowing them to move into highly-curved membrane buds and tubules that serve the recycling, retrograde and transcytotic pathways. Additionally, there can be specific sorting into the different pathways via distinct sorting mechanisms.

Glycosphingolipids are present within the outer membrane leaflet of cell membranes. They contain a ligand-binding oligosaccharide domain that faces the extracellular space, and a ceramide domain that anchors the lipid in the membrane bilayer. Ceramides consist of a sphingosine chain (typically C18:1 or C20:1) coupled to a fatty acid that can have diverse structures. The oligosaccharide domain prevents lipid flip-flop between membrane leaflets, causing all the glycosphingolipids to be distributed among intracellular compartments only by vesicular trafficking. Sorting of proteins and certain sphingolipids to various intracellular compartments of eukaryotic cells depends on movement of membranes through the secretory and endocytic pathways by vesicular carriers. For proteins, this occurs according to multiple and hierarchically ordered sorting determinants structurally encoded within the protein itself or within the structure of an associated receptor or chaperone. Methods of using glycosphingolipids isoforms containing a ceramide that comprises fatty acids of different structures (e.g., different fatty acid chain length, with or without double bonds) to deliver an agent (e.g., a therapeutic agent) into a cell or across a mucosal barrier have been described (e.g., in U.S. Pat. No. 9,457,097, incorporated herein by reference).

Simplifying the lipid carrier may simplify their synthesis, amplify their activity in transport of biologics, and promote their clinical translation. It is known that ceramides alone (e.g., without the oligosaccharide group, or simply glycoceramide) can flip flop from one membrane leaflet to another (e.g., as described in López-Montero et al., Biochim Biophys Acta. July; 1798(7):1348-56, incorporated herein by reference). Provided herein, in some aspects, are the use of ceramides (e.g., ceramides alone or glycoceramide) for trafficking agents (e.g., therapeutic agents) intracellularly or across epithelial or endothelial barriers.

Accordingly, some aspects of the present disclosure provide delivery vehicles comprising a ceramide and an agent to be delivered, wherein the ceramide: (a) does not comprise a fatty acid; or (b) comprises a fatty acid of C1-C28; and wherein the agent is attached to the ceramide. A "delivery vehicle" refers to a molecule or system that delivers an agent (e.g., a therapeutic agent) to a desired location, e.g., without limitation, to enter a cell or to reach a desired cellular compartment (e.g., the endoplasmic reticulum), to reach a desired part in a subject (e.g., an organ), or to reach a diseased site in a subject (e.g., a tumor site). In some embodiments, the delivery vehicle includes the agent to be delivered. In some embodiments, the delivery vehicle is associated with (or attached to) the agent to be delivered. In these situations, complexes comprising the delivery vehicle and the agent to be delivered are formed and termed herein a "ceramide-agent complex." In some embodiments, the agent is a therapeutic agent and the complex comprising the delivery vehicle and the therapeutic agent is herein termed a "ceramide-therapeutic agent complex."

A "ceramide," as used herein, refers to a molecule comprising a sphingosine core structure. A sphingosine is an amino alcohol with an unsaturated hydrocarbon chain that is typically 18-carbon or 20-carbon in length, which forms a primary part of sphingolipids (e.g., ceramides). The unsaturated hydrocarbon chain is attached to the amino acid serine to form the sphingosine. The term "ceramide" encompasses natural ceramides and ceramide analogs (e.g., synthetic or natural ceramide analogs). In some embodiments, the ceramide is a sphingolipid composed of sphingosine and a fatty acid. In some embodiments, the ceramide of the present disclosure is a ceramide analog. For example, the ceramide of the present disclosure may contain additional chemical moieties appended to a natural ceramide or contain modifications compared to a natural ceramide. Non-limiting examples of ceramide analogs that may be used in accordance with the present disclosure include: 2-hydroxy-ceramide, diene-deoxy-ceramide, dihydroceramide, dihydroceramide phosphate, o-acyl-ceramide, ceramide phosphate, sphinganine, and methyl-sphingosine.

In some embodiments, the ceramides of the present disclosure encompass ceramide analogs with the core structure built upon amino acids other than serine (i.e., having a core structure other than sphingosine). For example, in some embodiments, the ceramide described herein comprises amino acid backbones containing ornithine (e.g., N-acyloxyacyl-ornithine, and bacterial cerilipin, as described in Kawai et al., FEMS Immunol Med Microbiol 1999, 23, 67 and Tahara et al., Agric Biol Chem 1976, 40, 243, incorporated herein by reference), tyrosine (e.g., Brominated molo-lipids from sea sponge as described in Ross et al., J Nat Prod 2000, 63, 501, incorporated herein by reference), glycine (e.g., iso-3-hydroxy heptadecanoic acid-containing lipid from Cytophaga johnsonae, as described in Kawazoe et al., J Bacteriol 1991, 173, 5470, incorporated herein by reference), leucine (e.g., Lipstatin, which is an inhibitor of pancreatic protease, as described in Weibel et al., J Antibiot 1987, 1081, incorporated herein by reference), proline (e.g., N-stearoyl proline as described in Sivasamy et al., JAOCS 2001, 78, 897, incorporated herein by reference), glutamine (e.g., Volicitin. N-(17-hydroxylinolenoyl)-1-glutamine, as described in Pare et al., PNAS 1998, 95, 13971, incorporated herein by reference) or taurine (e.g., N-acyl taurine, as described in Saghatelian et al., Biochemistry 2006, 45, 9007, incorporated herein by reference). Non-limiting, exemplary structures of these ceramide analogs are provided in FIGS. 24A-24G.

A "fatty acid" is a carboxylic acid with an aliphatic chain, which is either saturated or unsaturated. Fatty acids that have double bonds between backbone carbons are known as unsaturated. Fatty acids without double bonds between backbone carbons are known as saturated. The length of a fatty acid chain, is herein referred to using the number of backbone carbons atoms in the fatty acid chain. For example, a fatty acid chain with X number of backbone carbons is expressed as CX herein, wherein X is an integer. In some embodiments, X is 0, meaning the ceramide does not comprise a fatty acid. A ceramide that does not have a fatty acid is a sphingosine (also referred to as a "lyso-ceramide" herein). When a sphingosine is referred to herein, it also means the molecule does not have a sugar moiety. In some embodiments, X is an integer between 1-30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30). In some embodiments, the ceramide of the present disclosure comprises a fatty acid of C1-C28 (e.g., C1, C2, C3, C4, C5, C6, C7, C8, C9, C10, C11, C12, C13, C14, C15, C16, C17, C18, C19, C20. C21, C22, C23, C24, C25, C26, C27, or C28) in length. The number of double bonds between backbone carbons in a fatty acid chain with X number of backbone carbons is expressed as CX:Y, wherein Y is the number of double bonds between backbone carbons and is an integer. For example, a fatty acid chain with 20 backbone carbons and 1 double bond is expressed as "C20:1" herein. In some embodiments. Y is 0, meaning the fatty acid does not contain a double bond between backbone carbons (i.e., a saturated fatty acid). The ceramide chain of the present disclosure, in some embodiments, contains one or more (e.g., 1, 2, 3, 4, 5, 6, 7, 8, 9, 10, or more) double bonds between backbone carbons. In some embodiments, the double bond is a cis-double bond. A "cis-double bond" refers to an isoform of a double bond formed between two carbon atoms. In addition to the double bond, other chemical groups (e.g., —H, —CH3, —COOH) also form bonds with the carbon atom involved in the cis-double bond, and "cis" indicates that the chemical groups other than —H are on the same side of the carbon chain. One skilled in the art is familiar with these terms.

In some embodiments, the ceramide comprises a fatty acid of C1-C12 (e.g., for transcytosis applications). In some embodiments, the ceramide comprises a fatty acid of C13-C28 (e.g., for non-transcytosis applications).

In some embodiments, the ceramide comprises a fatty acid of C1-C6 (e.g., C1. C2, C3, C4, C5, or C6) in length. In some embodiments, the fatty acid of C1-C6 has no double bond between two carbon atoms (e.g., any of the backbone carbons). In some embodiments, the ceramide comprises a fatty acid chain of C4. In some embodiments, the ceramide comprises a fatty acid chain of C6. In some embodiments, the fatty acid of C1-C6 comprises at least one cis-double bond (e.g., 1, 2, or more cis double bond).

In some embodiments, the ceramide comprises a fatty acid of C7-C28 (e.g., C7. C8, C9. C10. C11, C12, C13. C14, C15, C16. C17. C18, C19, C20, C21. C22. C23, C24. C25. C26. C27, or C28) in length. In some embodiments, the ceramide comprises a fatty acid chain of C8. In some embodiments, the fatty acid of C7-C28 comprises at least one cis-double bonds between two carbon atoms (e.g., any of the backbone carbons). For example, the fatty acid of C7-C28 may comprise 1-10 cis-double bonds. In some embodiments, the fatty acid of C7-C28 comprises 1-10, 1-9, 1-8, 1-7, 1-6, 1-5, 1-4, 1-3, 1-2, 2-10, 2-9, 2-8, 2-7, 2-6, 2-5, 24, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-10, or 9-10 cis-double bonds. In some embodiments, the fatty acid of C7-C28 comprises 1, 2, 3, 4, 5, 6, 7, 8, 9, 10, or more cis-double bonds. In some embodiments, the fatty acid is C7-C16 and comprises at least one cis-double bonds. In some embodiments, the fatty acid is C17-C28 and comprises at least one cis-double bonds in C1-C18 region of the fatty acid. For example, the at least one cis-double bonds may be in C1-C18, C1-C17, C1-C16, C1-C15. C1-C14, C1-C13, C1-C12, C1-C11. C1-C10, C1-C9, C1-C8. C1-C7, C1-C6, C1-C5, C1-C4. C1-C3, C1-C2, C2-C18, C2-C17, C2-C16. C2-C15, C2-C14. C2-C13, C2-C12, C2-C11, C2-C10. C2-C9, C2-C8. C2-C7. C2-C6, C2-C5, C2-C4, C2-C3. C3-C18. C3-C17, C3-C16, C3-C15. C3-C14, C3-C13, C3-C12. C3-C11, C3-C10. C3-C9, C3-C8, C3-C7, C3-C6. C3-C5, C3-C4, C4-C18, C4-C17, C4-C16. C4-C15, C4-C14. C4-C13, C4-C12. C4-C11. C4-C10, C4-C9, C4-C8, C4-C7, C4-C6, C4-C5, C5-C18, C5-C17. C5-C16, C5-C15. C5-C14, C5-C13. C5-C12, C5-C11. C5-C10, C5-C9. C5-C8. C5-C7, C5-C6. C6-C18, C6-C17, C6-C16, C6-C15. C6-C14, C6-C13, C6-C12. C6-C11, C6-C10. C6-C9, C6-C8, C6-C7, C7-C18. C7-C17, C7-C16. C7-C15, C7-C14. C7-C13, C7-C12. C7-C11. C7-C10, C7-C9. C7-C8, C8-C18, C8-C17, C8-C16. C8-C15, C8-C14. C8-C13, C8-C12. C8-C11, C8-C10, C8-C9. C9-C18. C9-C17, C9-C16. C9-C15, C9-C14. C9-C13. C9-C12, C9-C11. C9-C10, C10-C18. C10-C17. C10-C16, C10-C15, C10-C14, C10-C13, C10-C12, C10-C11, C11-C18, C11-C17, C11-C16, C11-C15. C11-C14, C11-C13, C11-C12, C12-C18. C12-C17, C12-C16, C12-C15, C12-C14, C12-C13, C13-C18, C13-C17, C13-C16, C13-C15, C13-C14, C14-C18. C14-C17, C14-C16, C14-C15. C15-C18, C15-C17. C15-C16, C16-C18. C16-C17, or C17-C18 region of the fatty acid. In some embodiments, the fatty acid is C17-C28 and the at least one cis-double bonds are in C1-C16 region of the fatty acid. In some embodiments, the fatty acid is C17-C28 and the at least one cis-double bonds are in C1-C14 region of the fatty acid. In some embodiments, the fatty acid of C7-C28 has no double bond between two carbon atoms (e.g., any of the backbone carbons).

In some embodiments, the fatty acid of C7-C28 comprises one or more (e.g., 1, 2, 3, 4, 5, 6, 7, 8, 9, 10, or more) chemical moieties (e.g., bulky chemical moieties) appended (e.g., covalently attached) to the fatty acid chain. Non-limiting examples of chemical moieties that may be appended to the C7-C28 fatty acid chain of the ceramide described herein include: branched methylation or acylation, bulky non-polar fluorophores such as BODIPY, aromatic rings, sterols, prenylation, halogenation (e.g., fluorination), and any compound that deviates from the linear structure of a fully saturated hydrocarbon chain. In some embodiments, the fatty acid is C7-C16 and comprises at least one chemical moieties (e.g., bulky chemical moieties) appended to the fatty acid chain. In some embodiments, the fatty acid is C17-C28 and comprises at least one chemical moieties (e.g., bulky chemical moieties) appended to the fatty acid chain in C1-C18 region of the fatty acid. For example, the at least one chemical moieties (e.g., bulky chemical moieties) may be appended in C1-C18, C1-C17. C1-C16, C1-C15, C1-C14. C1-C13, C1-C12. C1-C11. C1-C10, C1-C9. C1-C8, C1-C7. C1-C6. C1-C5, C1-C4, C1-C3, C1-C2, C2-C18, C2-C17. C2-C16, C2-C15. C2-C14, C2-C13, C2-C12, C2-C11, C2-C10, C2-C9, C2-C8, C2-C7, C2-C6, C2-C5, C2-C4, C2-C3. C3-C18, C3-C17. C3-C16, C3-C15, C3-C14, C3-C13. C3-C12, C3-C11. C3-C10, C3-C9. C3-C8, C3-C7, C3-C6. C3-C5, C3-C4. C4-C18, C4-C17. C4-C16, C4-C15, C4-C14. C4-C13, C4-C12. C4-C11, C4-C10. C4-C9, C4-C8. C4-C7, C4-C6, C4-C5. C5-C18, C5-C17. C5-C16, C5-C15. C5-C14, C5-C13, C5-C12. C5-C11. C5-C10, C5-C9. C5-C8. C5-C7, C5-C6. C6-C18, C6-C17. C6-C16. C6-C15. C6-C14, C6-C13, C6-C12, C6-C11. C6-C10, C6-C9. C6-C8. C6-C7, C7-C18. C7-C17, C7-C16. C7-C15, C7-C14. C7-C13, C7-C12. C7-C11. C7-C10. C7-C9, C7-C8, C8-C18. C8-C17, C8-C16, C8-C15. C8-C14. C8-C13, C8-C12. C8-C11, C8-C10. C8-C9, C9-C18. C9-C17. C9-C16. C9-C15, C9-C14. C9-C13, C9-C12. C9-C11. C9-C10, C10-C18. C0-C17, C10-C16. C10-C15. C10-C14. C10-C13. C10-C12. C10-C11. C11-C18. C11-C17. C11-C16. C11-C15. C11-C14. C11-C13, C11-C12. C12-C18, C12-C17. C12-C16, C12-C15. C12-C14, C12-C13. C13-C18. C13-C17, C13-C16. C13-C15, C13-C14. C14-C18, C14-C17. C14-C16. C14-C15, C15-C18, C15-C17. C15-C16, C16-C18. C16-C17, or C17-C18 region of the fatty acid. In some embodiments, the fatty acid is C17-C28 and the at least one chemical moieties (e.g., bulky chemical moieties) are appended in C1-C16 region of the fatty acid. In some embodiments, the fatty acid is C17-C28 and the at least one chemical moieties (e.g., bulky chemical moieties) are appended in C1-C14 region of the fatty acid.

In some embodiments, any of the ceramide of the present disclosure (e.g., a ceramide with or without a fatty acid chain) further comprises a sugar (e.g., a glycoceramide). In some embodiments, the ceramide comprises a fatty acid chain of C1-C6 and further comprises a sugar. In some embodiments, the ceramide comprises a fatty acid chain of C7-C28 and further comprises a sugar. In some embodiments, the ceramide does not comprise a fatty acid chain (i.e., a sphingosine or a lyso-ceramide) and further comprises a sugar. A ceramide that does not contain a fatty acid chain but comprises a sugar is also referred to herein as a "glycosphingosine" or a "lyso-glycoceramide."

Figure 7:
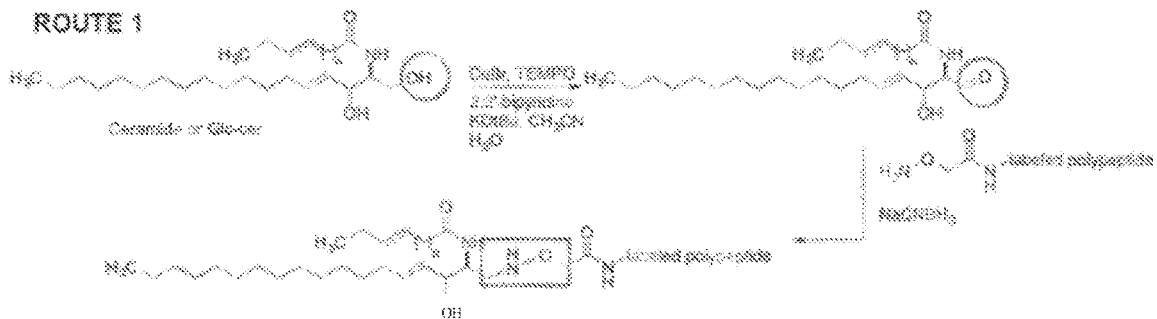
FIG. 7. Chemical synthesis of peptide onto ceramide and glucosylceramide. The primary hydroxyl(circle) located on the ceramide (or on sugar of Glc-Cer) are oxidized to form an aldehyde catalyzed by copper bromide, 2,2,6,6-Tetramethyl-piperidin-1-yl)oxyl (TEMPO) and 2,2 bipyridine. The reaction is enhanced in the presence of the base potassium tert-butoxide (KOtBu). This allows for the reaction to aminooxy containing peptides to form stable bonds (box).

A "glycoceramide" refers to a ceramide comprising a sugar attached to its primary hydroxyl group (FIG. 7). In some embodiments, the sugar is a simple sugar. A "simple sugar" is a monosaccharide made up of single sugar molecules. Non-limiting examples of simple sugars include: glucose, fructose, and galactose. Thus, in some embodiments, the ceramide of the present disclosure is a glucose-ceramide (Glc-Cer), a fructose ceramide, or a galactose ceramide. In some embodiments, the sugar is an oligosaccharide. In some embodiments, the ceramide is a glycoceramide and the agent to be delivered is attached to the sugar of the glycoceramide.

In some embodiments, the ceramide of the present disclosure does not comprise a sugar. In some embodiments, the agent is attached to the ceramide (e.g., to the primary hydroxyl group of the ceramide, see FIG. 7).

The agent may be attached to the ceramide by any methods known in the art. In some embodiments, the agent is attached non-covalently, e.g., without limitation, by van der Waals forces, hydrophobic interaction, hydrogen bond interaction, or ionic interactions.

In some embodiments, the agent is attached covalently. For example, in some embodiments, the ceramide (e.g., the primary hydroxyl group of the ceramide) or the sugar of the glycoceramide may be functionalized with a reactive chemical group. One example of such reactive group is a "click chemistry handle." Click chemistry is a chemical approach introduced describes chemistry tailored to generate substances quickly and reliably by joining small units together. See, e.g., Kolb, Finn and Sharpless Angewandte Chemie International Edition (2001) 40: 2004-2021: Evans, Australian Journal of Chemistry (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). Non-limiting examples of a click chemistry handle include an azide handle, an alkyne handle, or an aziridine handle. Azide is the anion with the formula N3—. It is the conjugate base of hydrazoic acid (HN3). N3— is a linear anion that is isoelectronic with CO2, NCO—, N2O, NO2+ and NCF. Azide can be described by several resonance structures, an important one being —N=N+=N—. An alkyne is an unsaturated hydrocarbon containing at least one carbon-carbon triple bond. The simplest acyclic alkynes with only one triple bond and no other functional groups form a homologous series with the general chemical formula CnH2n-2. Alkynes are traditionally known as acetylenes, although the name acetylene also refers specifically to C2H2, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—CH2—). The parent compound is aziridine (or ethylene imine), with molecular formula C2H5N.

Other non-limiting, exemplary reactive groups include: acetals, ketals, hemiacetals, and hemiketals, carboxylic acids, strong non-oxidizing acids, strong oxidizing acids, weak acids, acrylates and acrylic acids, acyl halides, sulfonyl halides, chloroformates, alcohols and polyols, aldehydes, alkynes with or without acetylenic hydrogen amides and imides, amines, aromatic, amines, phosphines, pyridines, anhydrides, aryl halides, azo, diazo, azido, hydrazine, and azide compounds, strong bases, weak bases, carbamates, carbonate salts, chlorosilanes, conjugated dienes, cyanides, inorganic, diazonium salts, epoxides, esters, sulfate esters, phosphate esters, thiophosphate esters borate esters, ethers, soluble fluoride salts, fluorinated organic compounds, halogenated organic compounds, halogenating agents, aliphatic saturated hydrocarbons, aliphatic unsaturated hydrocarbons, hydrocarbons, aromatic, insufficient information for classification, isocyanates and isothiocyanates, ketones, metal hydrides, metal alkyls, metal aryls, and silanes, alkali metals, nitrate and nitrite compounds, inorganic, nitrides, phosphides, carbides, and silicides, nitriles, nitro, nitroso, nitrate, nitrite compounds, organic, non-redox-active inorganic compounds, organometallics, oximes, peroxides, organic, phenolic salts, phenols and cresols, polymerizable compounds, quaternary ammonium and phosphonium salts, strong reducing agents, weak reducing agents, acidic salts, basic salts, siloxanes, inorganic sulfides, organic sulfides, sulfite and thiosulfate salts, sulfonates, phosphonates, organic thiophosphonates, thiocarbamate esters and salts, and dithiocarbamate esters and salts. The agent to be attached to the ceramide (e.g., via the reactive chemical group) may contain a corresponding chemical group that reacts with the oligosaccharide or ceramide, thus resulting in covalent attachment. For example, an agent that is a protein or polypeptide can be coupled via its N- or C-terminus, or via an endogenous residue (e.g., lysine) by chemical cross-linking.

In some embodiments, the agent is attached to the ceramide via a linker. In some embodiments, the linker is a pseudo-glycopeptide linker (e.g., see FIG. 8). A "pseudo-glycopeptide linker" refers to linkers comprising at least one (e.g., 1, 2, 3, 4, 5, 6, 7, 8, 9, 10, or more) sugar (carbohydrate) covalently attached an amino acid backbone (the peptide) via side chains of the amino acids in the backbone. Non-limiting examples of sugars that may be attached to the amino acid backbone include: fructose, glucose, galactose, sialic acid, and N-Acetylgalactosamine (GalNAc). In some embodiments, the sugar in the pseudo-glycopeptide linker is attached to the amino acid backbone via the side chain of a serine, threonine, or asparagine. For pseudo-glycopeptides that contain more than one sugars, the sugars may be attached to the amino acid backbone via the same or different amino acid side chain. In some embodiments, the amino acid backbone of the pseudo-glycopeptide linker comprises 1-30 amino acids. For example, the amino acid backbone of the pseudo-glycopeptide linker may comprise 1-30, 1-25, 1-20, 1-15, 1-1-, 1-5, 5-10, 5-25, 5-20, 5-15, 5-10, 10-30, 10-25, 10-20, 10-15, 15-30, 15-25, 15-20, 20-30, 20-25, or 25-30 amino acids. In some embodiments, the amino acid backbone of the pseudo-glycopeptide linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the amino acid backbone of the pseudo-glycopeptide linker comprises 1-10 amino acids. For example, the amino acid backbone of the pseudo-glycopeptide linker may comprise 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-10, or 9-10 amino acids. In some embodiments, the amino acid backbone of the pseudo-glycopeptide linker comprises 1, 2, 3, 4, 5, 6, 7, 8, 9, or 10 amino acids. In some embodiments, the amino acid backbone of the pseudo-glycopeptide linker comprises more than 10 amino acids (e.g., 11-30 amino acids). For example, the amino acid backbone of the pseudo-glycopeptide linker may comprise 11, 12, 13, 14, 15, 16, 17, 18, 19, 20, 21, 22, 23, 24, 25, 26, 27, 28, 29, or 30 amino acids.

In some embodiments, the linker is a peptide linker. In some embodiments, the agent is a protein or a peptide. In such instances, one or more of the amino acids of the protein or peptide may be modified to include a chemical entity such as a carbohydrate group, a hydroxyl group, a phosphate group, a farnesyl group, an isofarnesyl group, a fatty acid group, a linker for attaching to the oligosaccharide.

In some embodiments, the linker is a cleavable linker. A "cleavable linker" refers to a linker that can be cleaved by a chemical agent or an enzyme and thus release the agent from the ceramide carrier. In some embodiments, the cleavable linker comprises an ester linkage (e.g., the linker can be a peptide linker comprising an ester linker). In some embodiments, the ester linkage can be cleaved by an esterase (e.g., leukocyte esterase whose level is elevated at sites of inflammation, or carboxylesterase hCE-2 that is specific to gastrointestinal endosomes).

In some embodiments, the cleavable linker comprises a cleavage motif for an endosomal protease. An "endosomal protease" refers to a protease that is present in endosomes. It is herein interchangeably referred to as a "lysosomal protease." Endosomal proteases belong to the aspartic, cysteine, or serine proteinase families of hydrolytic enzymes. Endosomal proteases are expressed ubiquitously, and in a tissue- or cell type-specific manner and are usually detected within all vesicles of the endocytic pathway. Reference and classification of endosomal proteases is available in the art. For example, lists of known endosomal proteases can be found in the MEROPS database (merops.sanger.ac.uk). In some embodiments, the endosomal protease is furin or matriptase. Furin is a calcium-dependent serine endoprotease that can efficiently cleave precursor proteins at their paired basic amino acid processing sites. Furin cleaves proteins downstream of a basic amino acid target sequence (canonically, Arg-X-(Arg/Lys)-Arg'). Matriptase is a trypsin-like integral-membrane serine peptidase and cleaves substrates with Arg or Lys at the P1 position and prefers small side-chain amino acids, such as Ala and Gly, at the P2 position.

In some embodiments, the cleavable linker comprises a disulfide linkage. A "disulfide linkage" is also referred to as a disulfide bond or S—S bond, which is a covalent bond derived from two thiol groups. Disulfide bonds can be formed by oxidation of sulfhydryl groups and can be cleaved via reduction (e.g., via using reductants such as tris(2-carboxyethyl)phosphine (TCEP), 2-Mercaptoethanol IP-ME) or dithiothreitol (DTT)).

The ceramides described herein are able to act as delivery vehicles to deliver an agent across cell membrane or across mucosal barrier and direct intracellular trafficking of the agent. For example, in some embodiments, the ceramide-agent complex are directed by the ceramide to a desired intracellular location, e.g., the endoplasmic reticulum (ER). In some embodiments, the ceramide-agent complex is directed by the ceramide away from degradative pathways (e.g., lysosome). As such, in some embodiments, the cellular half-life of the agent is prolonged when the agent is part of the ceramide-agent complex, compared to when the agent is delivered into cells alone. In some embodiments, the cellular half-life of the agent is prolonged by at least 20% when the agent is part of the ceramide-agent complex, compared to when the agent is delivered into cells alone. In some embodiments, the cellular half-life of the agent is prolonged by at least 20%, at least 30%, at least 40%, at least 50%, at least 60%, at least 70%, at least 80%, at least 90%, at least 100%, at least 2 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or more, when the agent is part of the ceramide-agent complex, compared to when the agent is delivered into cells alone. In some embodiments, the cellular half-life of the agent is prolonged by 20%, 30%, 40%, 50%, 60%, 70%, 80%, 90%, 100%, 2 fold, 5 fold, 10 fold, 20 fold, 30 fold, 40 fold, 50 fold, 60 fold, 70 fold, 80 fold, 90 fold, 100 fold, 500 fold, 1000 fold or more, when the agent is part of the ceramide-agent complex, compared to when the agent is delivered into cells alone.

In some embodiments, the agent is delivered across an epithelial or endothelial barrier (e.g., a mucosal barrier) by transcytosis, when the agent is attached to the ceramide to form a ceramide-agent complex. Mucosal barrier is composed of compact epithelial cell lining (e.g., in the stomach or in the intestines). The intestinal mucosal harrier, also referred to as intestinal barrier, refers to the property of the intestinal mucosa that ensures adequate containment of undesirable luminal contents within the intestine while preserving the ability to absorb nutrients. The gastric mucosal barrier is the property of the stomach that allows it to safely contain the gastric acid required for digestion.

In some embodiments, the agent is not able to cross an epithelial or endothelial barrier (e.g., a mucosal barrier) alone and is able to cross mucosal barriers in complex with the ceramides described herein. In some embodiments, the delivery of the agent across an epithelial or endothelial barrier (e.g., a mucosal barrier) is enhanced (e.g., by at least 20%) when the agent is in complex with the ceramides described herein, compared to when the agent is delivered alone. For example, the delivery of the agent across an epithelial or endothelial harrier (e.g., a mucosal barrier) is enhanced by at least 20%, at least 30%, at least 40%, at least 50%, at least 60%, at least 70%, at least 80%, at least 90%, at least 100%, at least 2 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or more, when the agent is in complex with the ceramides described herein, compared to when the agent is delivered alone. In some embodiments, the delivery of the agent across an epithelial or endothelial barrier (e.g., a mucosal barrier) is enhanced by 20%, 30%, 40%, 50%, 60%, 70%, 80%, 90%, 100%, 2 fold, 5 fold, 10 fold, 20 fold, 30 fold. 40 fold, 50 fold, 60 fold, 70 fold, 80 fold, 90 fold, 100 fold, 500 fold, 1000 fold or more, when the agent is in complex with the ceramides described herein, compared to when the agent is delivered alone.

Other aspects of the present disclosure provide agents that may be delivered by the ceramides described herein. The agent may be any bioactive agent or therapeutic agent. A "therapeutic agent" refers to an agent that has therapeutic effects to a disease or disorder. The complex between the ceramide and the therapeutic agent is referred to herein as the "ceramide-therapeutic agent complex." A therapeutic agent may be, without limitation, proteins, peptides, nucleic acids, small molecules drugs, polysaccharides and carbohydrates, lipids, glycoproteins, small molecules, synthetic organic and inorganic drugs exerting a biological effect when administered to a subject, and combinations thereof. In some embodiments, the therapeutic agent is an anti-inflammatory agent, a vaccine antigen, a vaccine adjuvant, an antibody, a ScFv, a nanobody, and enzyme, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder, a skin disease, an eye disease, a lysosomal storage disease, or a neurological disease. In some embodiments, the therapeutic agent is a protein or a peptide. In some embodiments, the protein or peptide is glucagon-like peptide-1 (GLP-1), or a functional fragment thereof. In some embodiments, the protein or peptide is Exendin-4, or a functional fragment thereof.

"Glucagon-like peptide-1 (GLP-1)" is a 30 amino acid long peptide hormone deriving from the tissue-specific posttranslational processing of the proglucagon gene. It is produced and secreted by intestinal enteroendocrine L-cells and certain neurons within the nucleus of the solitary tract in the brainstem upon food consumption. The initial product GLP-1(1-37) is susceptible to amidation and proteolytic cleavage which gives rise to the two truncated and equipotent biologically active forms, GLP-1(7-36)amide and GLP-1(7-37). Active GLP-1 composes two α-helices from amino acid position 13-20 and 24-35 separated by a linker region. GLP-1 possesses several physiological properties that make it (and its functional analogs) a subject of intensive investigation as a potential treatment of diabetes mellitus. Further, GLP-1 is has the ability to decrease blood sugar levels in a glucose-dependent manner by enhancing the secretion of insulin. Thus, GLP-1 has been associated with numerous regulatory and protective effects. GLP-1-based treatment has been associated with weight loss and lower hypoglycemia risks, two very important aspects of a life with diabetes.

"Exendin-4" is a peptide agonist of the glucagon-like peptide (GLP) receptor that promotes insulin secretion. Exendin-4 binds to the intact human Glucagon-like peptide-1 receptor (GLP-1R) in a similar way to GLP-1 and bears a 50% amino acid homology to GLP-1. Exendin-4 facilitates glucose control via augmentation of pancreas response (i.e. increases insulin secretion) in response to eating meals, suppressing pancreatic release of glucagon in response to eating, reducing rate of gastric emptying, suppressing appetite, and reducing liver fat content. In some embodiments, the therapeutic agent is a fusion protein comprise GLP-1 or a functional fragment thereof and Exendin-4 or a functional fragment thereof.

In some embodiments, the therapeutic agent is a vaccine antigen. A "vaccine antigen" is a molecule or moiety that, when administered to a subject, activates or increases the production of antibodies that specifically bind the antigen. In some embodiments, an antigen is a protein or a polysaccharide. Antigens of pathogens are well known to those of skill in the art and include, but are not limited to parts (coats, capsules, cell walls, flagella, fimbriae, and toxins) of bacteria, viruses, and other microorganisms. A vaccine typically comprises an antigen, and is intentionally administered to a subject to induce an immune response in the recipient subject. The antigen may be from a pathogenic virus, bacteria, or fungi.

Examples of pathogenic virus include, without limitation: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Caliciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruscs, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of pathogenic bacteria include, without limitation: *Helicobacter pyloris, Borelia burgdorferi, Legionella pneumophilia, Mycobacteria* spp. (e.g., *M. tuberculosis, M. avium, M. intracellulare, M. kansasii, M. gordonae*). *Staphylococcus aureus, Neisseria gonorrhoeae, Neisseria meningitidis, Listeria monocytogenes, Streptococcus pyogenes* (Group A *Streptococcus*). *Streptococcus agalactiae* (Group B *Streptococcus*), *Streptococcus* (*viridans* group). *Streptococcus faecalis, Streptococcus bovis, Streptococcus* (anaerobic spp.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp.,

*Erysipelothrix rhusiopathiae, Clostridium perfringens, Clostridium tetani, Enterobacter aerogenes, Klebsiella pneumoniae, Pasteurella multocida. Bacteroides* sp., *Fusobacterium nucleatum. Streptobacillus moniliformis, Treponema pallidum, Treponema pertenue, Leptospira*, and *Actinomyces israeli.*

Examples of pathogenic fungi include, without limitation: *Cryptococcus neoformans, Histoplasma capsulatum, Coccidioides immitis, Blastomyces dermatitidis. Chlamydia trachomatis, Candida albicans*. Other infectious organisms (i.e., protists) include: *Plasmodium falciparum* and *Toxoplasma gondii*.

In some embodiments, the therapeutic agent is an agent that induces immunological tolerance. Immunologic tolerance is a state of immune unresponsiveness specific to a particular antigen or set of antigens induced by previous exposure to that antigen or set. In some embodiments, the immunologic tolerance is oral tolerance. Oral tolerance is the state of local and systemic immune unresponsiveness that is induced by oral administration of innocuous antigen such as food proteins. In some embodiments, the therapeutic agent is an agent for induce immunological tolerance for the treatment of allergy or autoimmune disease (e.g., multiple sclerosis).

Other non-limiting examples of agents that may be delivered using the ceramides described herein are provided.

Non-limiting, exemplary chemopharmaceutically compositions that may be used in the liposome drug delivery systems of the present disclosure include. Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel. Doxifluridine, Doxorubicin. Epirubicin, Epothilone, Etoposide. Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

Examples of antineoplastic compounds include, without limitation: nitrosoureas, e.g., carmustine, lomustine, semustine, strepzotocin; Methylhydrazines, e.g., procarbazine, dacarbazine; steroid hormones, e.g., glucocorticoids, estrogens, progestins, androgens, tetrahydrodesoxycaricosterone, cytokines and growth factors; Asparaginase.

Examples of immunoactive compounds include, without limitation: immunosuppressives, e.g., pyrimethamine, trimethopterin, penicillamine, cyclosporine, azathioprine; immunostimulants, e.g., levamisole, diethyl dithiocarbamate, enkephalins, endorphins.

Examples of antimicrobial compounds include, without limitation: antibiotics, e.g., beta lactam, penicillin, cephalosporins, carbapenims and monobactams, beta-lactamase inhibitors, aminoglycosides, macrolides, tetraclyins, spectinomycin; Antimalarials, Amebicides, Antiprotazoal, Antifungals, e.g., amphotericin beta or clotrimazole, antiviral. e.g., acyclovir, idoxuridine, ribavirin, trifluridine, vidarbine, gancyclovir.

Examples of parasiticides include, without limitation: antihalmintics, Radiopharmaceutics, gastrointestinal drugs.

Examples of hematologic compounds include, without limitation: immunoglobulins; blood clotting proteins; e.g., antihemophilic factor, factor IX complex; anticoagulants, e.g., dicumarol, heparin Na; fibrolysin inhibitors, tranexamic acid.

Examples of cardiovascular drugs include, without limitation: peripheral antiadrenergic drugs, centrally acting antihypertensive drugs. e.g., methyldopa, methyldopa HCl; antihypertensive direct vasodilators, e.g., diazoxide, hydralazine HCl; drugs affecting renin-angiotensin system; peripheral vasodilators, phentolamine; antianginal drugs; cardiac glycosides; inodilators; e.g., amrinone, milrinone, enoximone, fenoximone, imazodan, sulmazole; antidysrhythmic; calcium entry blockers; drugs affecting blood lipids; nadolol, hosentan, rezulin.

Examples of respiratory drugs include, without limitation: syapthomimetic drugs: albuterol, bitolterol mesylate, dobutamine HCl, dopamine HCl, ephedrine SO, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs. e.g., anisotropine methylbromide, atropine SO4, clinidium Br, glycopyrrolate, ipratropium Br, scopolamine HBr.

Examples of neuromuscular blocking drugs include, without limitation: depolarizing, e.g., atracurium besylate, hexafluorenium Br, metocurine iodide, succinylcholine Cl, tubocurarine C1, vecuronium Br; centrally acting muscle relaxants, e.g., baclofen.

Examples of neurotransmitters and neurotransmitter agents include, without limitation: acetylcholine, adenosine, adenosine triphosphate, amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K+ channel toxins.

Examples of antiparkinson drugs include, without limitation: amaltidine HCl, benztropine mesylate, e.g., carbidopa.

Examples of diuretic drugs include, without limitation: dichlorphenamide, methazolamide, bendroflumethiazide, polythiazide.

Examples of uterine, antimigraine drugs include, without limitation: carboprost tromethamine, mesylate, methysergide maleate.

Examples of hormones include, without limitation: pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists, hormonal contraceptives, testicular hormones; gastrointestinal hormones; cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Examples of enzymes include, without limitation: lysosomal storage enzymes, hyaluronidase, streptokinase, tissue plasminogen activator, urokinase, PGE-adenosine deaminase, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidasc, maltasc, isomaltasc), DNascs, and RNascs.

Examples of intravenous anesthetics include, without limitation: droperidol, etomidate, fetanyl citrate/droperidol, hexobarbital, ketamine HCl, methohexital Na, thiamylal Na, thiopental Na.

Examples of antiepileptics include, without limitation, carbamazepine, clonazepam, divalproex Na, ethosuximide, mephenytoin, paramethadione, phenytoin, primidone.

Examples of peptides and proteins that may be used as therapeutic agents include, without limitation: ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins. GP1b-IX complex, GP11b-IIIa complex, vitronectin, thrombomodulin. CD4, CD55, CD58. CD59, CD44, lymphocye function-associated antigen, intercellular adhesion molecule, vascular cell adhesion molecule, Thy-1, antiporters. CA-15-3 antigen, fibronectins, laminin, myelin-associated glycoprotein. GAP, GAP-43, Exendin-4, and GLP-1.

Examples of cytokines and cytokine receptors include, without limitation: interleukin-1 (IL-1). IL-2. IL-3, IL-4, IL-5, IL-6, IL-7, IL-8, IL-9. IL-10, IL-11, IL-12, IL-13, IL-14, IL-15. IL-16. IL-17. IL-18, IL-1 receptor, IL-2 receptor, IL-3 receptor, IL-4 receptor, IL-5 receptor, IL-6 receptor. IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin. Fas, granulocyte colony stimulating factor, granulocyte macrophage colony stimulating factor, interferon-alpha, interferon-beta, interferon-gamma.

Examples of growth factors and protein hormones include, without limitation: erythropoietin, angiogenin, hepatocyte growth factor, fibroblast growth factor, keratinocyte growth factor, nerve growth factor, tumor growth factor-alpha, thrombopoietin, thyroid stimulating factor, thyroid releasing hormone, neurotrophin, epidermal growth factor. VEGF, ciliary neurotrophic factor, LDL, somatomedin, insulin growth factor, insulin-like growth factor I and II.

Examples of chemokines include, without limitation: ENA-78, ELC, GRO-alpha, GRO-beta, GRO-gamma, HRG, LIF, IP-10, MCP-1. MCP-2, MCP-3, MCP-4, MIP-1alpha, M1P-1beta. M1G, MDC, NT-3, NT-4. SCF, LIF, lcptin, RANTES, lymphotactin, cotaxin-1, eotaxin-2, TARC. TECK. WAP-1. WAP-2. GCP-1, GCP-2; alpha-chemokine receptors: CXCR1, CXCR2, CXCR3, CXCR4, CXCR5, CXCR6, CXCR7; beta-chemokine receptors: CCR1, CCR2, CCR3, CCR4, CCR5, CCR6, CCR7.

In some embodiments, antibodies that may be delivered using the delivery vehicle described herein target antigens including, without limitation: (a) anti-cluster of differentiation antigen CD-1 through CD-166 and the ligands or counter receptors for these molecules; (b) anti-cytokine antibodies, e.g., anti-IL-1 through anti-IL-18 and the receptors for these molecules; (c) anti-immune receptor antibodies, antibodies against T cell receptors, major histocompatibility complexes I and R, B cell receptors, selectin killer inhibitory receptors, killer activating receptors, OX-40, MadCAM-1, Gly-CAM1, integrins, cadherens, sialoadherens, Fas, CTLA-4, Fc.gamma.-receptors, Fcalpha-receptors, Fc.epsilon.-receptors, Fc.mu.-receptors, and their ligands; (d) anti-metalloproteinase antibodies, e.g., collagenase. MMP-1 through MMP-8, TIMP-1, TIMP-2; anti-cell lysis/proinflammatory molecules, e.g., perforin, complement components, prostanoids, nitron oxide, thromboxanes; and (e) anti-adhesion molecules. e.g., carcioembryonic antigens, lamins, fibronectins.

Non-limiting, exemplary antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy). MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), cdrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUiX®), MDX-447. MDX-22, MDX-220 (anti-TAG-72). IOR-C5, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure. In some embodiments, the therapeutic agent is a nanobody. A "nanobody" is a therapeutic protein based on single-domain antibody fragments that contain the unique structural and functional properties of naturally-occurring heavy chain only antibodies. In some embodiments, the nanobody is anti-inflammatory. In some embodiments, the nanobody is against pathogenic agents (e.g., anthrax).

In some embodiments, the therapeutic agent is a ligand for a cell receptor (e.g., without limitation, a growth factor receptor, a G-protein coupled receptor, or a toll-like receptor).

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2. Jun, JunB and JunD; ATF; CREB; STAT-1, -2, -3, -4, -5 and -6; NFAT-1, -2 and -4; MAF; Thyroid Factor, IRF; Oct-1 and -2; NF-Y; Egr-1; and USF-43, EGR1, Sp1, and E2F1.

Examples of antiviral agents include, without limitation: reverse transcriptase inhibitors and nucleoside analogs. e.g. ddI, ddC, 3TC, ddA. AZT; protease inhibitors, e.g., Invirase, ABT-538; inhibitors of in RNA processing, e.g., ribavirin.

Other non-limiting examples of known therapeutics which may be delivered by coupling to a ceramide described herein include:

(a) Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb);
(b) Ceclor, Lorabid, Dynabac, Prozac, Darvon, Permax, Zyprexa, Humalog, Axid, Gemzar. Evista (Eli Lily);
(c) Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.);
(d) Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer);
(e) Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn);
(f) Lopid, Accrupil, Dilantin, Cognex, Neurontin, Loestrin, Dilzem, Fempatch, Estrostep, Rezulin, Lipitor, Omnicef, FemHRT, Suramin, Clinafloxacin (Warner Lambert).

Non-limiting examples of therapeutic agents for eye diseases include: Anti-infective drugs (e.g., Aciclovir, Chloramphenicol, Ciprofloxacin. Gentamicin, Neomycin. Polymyxin B); Anti-inflammatory drugs (e.g., Betamethasone. Dexamethasone, Emedastine, Nedocromil sodium, Prednisolone. Sodium cromoglicate); Artificial tears (e.g., Carmellose, Hydroxyethylcellulose. Hypromellose. Polyvinyl alcohol); and Mydriatics (e.g., Atropine, cyclopentolate, Phenylephrine).

Further non-limiting examples of therapeutic agents which may be delivered by the ceramide-therapeutic agent complex of the present invention may be found in: Goodman and Gilman's The Pharmacological Basis of Therapeutics, 9th ed. McGraw-Hill 1996, incorporated herein by reference.

The delivery vehicle comprising a ceramide and an agent to be delivered, or a ceramide-agent complex (e.g., a ceramide-therapeutic agent) complex may be formulated into pharmaceutical compositions. In some embodiments, the pharmaceutical composition further comprises a pharmaceutically acceptable carrier. "Pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" may be a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water, (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1.3 propanediol or 1,3 butandiol.

Among the acceptable vehicles and solvents that may be employed are water, Ringers solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Other aspects of the present disclosure provide methods of delivering an agent (e.g., a therapeutic agent) into a cell or across a mucosal surface or an endothelial barrier, the method comprising contacting the delivery vehicle, the ceramide-agent complex (e.g., the ceramide-therapeutic agent complex), or the pharmaceutical composition comprising the delivery vehicle or the ceramide-agent complex (e.g., the ceramide-therapeutic agent complex) with the cell, the mucosal surface, or the endothelial lumenal surface, under conditions appropriate for uptake of the delivery vehicle or the agent into the cell or absorption of the delivery vehicle or the agent across the mucosal surface or the endothelial barrier (e.g., via transcytosis). In some embodiments, the delivery vehicle, the ceramide-agent complex, or the pharmaceutical composition comprising the delivery vehicle or the ceramide-agent complex (e.g., the ceramide-therapeutic agent complex) are administered to a subject.

Methods of delivering agents (e.g., therapeutic agents) to different organs via intravenous infusion of the delivery vehicle or the ceramide-agent complex are also provided. Such organs may be, for example, without limitation, skeleton, joints, muscles, tendons, various types of glands, oesophagus, stomach, small intestine, large intestine, liver, pancreas, pharynx, larynx, trachea, bronchi, lungs, diaphragm, kidneys, ureters, bladder, urethra, ovaries, uterus, prostate, heart, lymph nodes, bone marrow, thymus, spleen, brain, and spinal cord. In some embodiments, the delivery vehicle or the ceramide-agent complex is delivered across an endothelial barrier (e.g., the endothelial barrier in the heart or brain) when it reaches the organ after intravenous infusion. In some embodiments, the intravenously infused delivery vehicle or the ceramide-agent complex are delivered to different organs and are sorted into intracellular compartments such as the lysosome (e.g., for lysosomal replacement therapies) or ER (e.g., for addressing protein folding problems). Delivery to liver after intravenous infusion of the delivery vehicle or the ceramide-agent complex greatly enhances (e.g., by at least 20%) the delivery of the agent to the liver, compared to delivering the agent alone.

Methods of enhancing the half-life of an agent in a subject are provided, the method comprising administering to the subject the delivery vehicle, the ceramide-therapeutic agent complex, or the composition described herein.

Methods of treating a disease or condition in a subject in need thereof are provided, the method comprising administering to the subject an effective amount of the delivery vehicle, the ceramide-therapeutic agent complex, or the composition described herein, wherein the effective amount is an amount sufficient to ameliorate/reduce the extent to which the disease or condition occurs in the subject. The disease may be any disease that can be treated by the agents described herein. In some embodiments, the disease is infection, allergy, autoimmune diseases (e.g., multiple sclerosis), liver diseases, lung diseases, neurological diseases, eye diseases or cancer.

An "effective amount" is the amount necessary or sufficient to have a desired effect in a subject. The effective amount will vary with the particular condition being treated, the age and physical condition of the subject being treated, the severity of the condition, the duration of the treatment, the nature of the concurrent therapy (if any), the specific route of administration and other factors within the knowledge and expertise of the health care practitioner. For example, an effective amount could be that amount necessary to eliminate a tumor, cancer, or bacterial, viral or fungal infection. This amount will vary from individual to individual and can be determined empirically using known methods by one of ordinary skill in the art.

The delivery vehicle, the ceramide-agent complex, or the pharmaceutical composition comprising the delivery vehicle or the ceramide-agent complex (e.g., the ceramide-therapeutic agent complex) may be administered by any route. Routes of administration include enteral routes, such as oral and any other means by which the gastrointestinal tract is involved, and parenteral routes, such as by injection (subcutaneous, intravenous, intramuscular injection) or infusion (typically by intravenous route). In some embodiments, the administration is done intravenously, intramuscularly, intradermally, subcutaneously, intrathecally, intraperitoneally, intraarterially, intracardiacally, intraosseously, intraocularly, intravitreally, intrapleurally, intranasally, or injection into the joint. The injection can be in a bolus or a continuous infusion. In some embodiments, the administration is done nonparenterally (e.g., done orally, sublingually, topically, rectally, via inhalation, nasally, as eye drops, as eye patches, to the cervix, or to the skin). For delivery across tight endothelial barriers, in some embodiments, the ceramide-therapeutic agent complex is delivered intravenously, intramuscularly, or subcutaneously.

Methods of treating a disease or disorder are also provided. The delivery vehicle, the ceramide-agent complex, or the pharmaceutical composition comprising the delivery vehicle or the ceramide-agent complex (e.g., the ceramide-therapeutic agent complex) may be administered to a subject who has, has had or is susceptible to developing one or more conditions/diseases that require or would benefit from treatment. For example, the compositions described herein may be used to treat, prevent or ameliorate immune system deficiencies, infectious diseases (viral, fungal, bacterial or parasitic), autoimmune diseases, diabetes, blood disorders, cancers, metabolic disorders, allergies, inflammatory bowel disease and skin disorders. In addition, gangliosides attached to antigen can be administered to stimulate a subject's response to a vaccine. The antigen is selected from the group consisting of: an antigen that is characteristic of a pathogen, an antigen that is characteristic of an autoimmune disease, an antigen that is characteristic of an allergen and an antigen that is characteristic of a tumor. In some embodiments, the disease or disorder to be treated is diabetes. In some embodiments, the disease or disorder is infection, e.g., by a pathogenic virus, bacteria, or fungi. In some embodiments, the disease or disorder is cancer.

Immune system deficiencies include any disease or disorder in which a subject's immune system is not functioning normally or in which it would be useful to boost the subject's immune response, for example to eliminate a tumor or cancer (e.g. tumors of the brain, lung (e.g. small cell and non-small cell), ovary, breast, prostate, colon, as well as other carcinomas and sarcomas) or an infection in a subject.

Examples of autoimmune diseases include, without limitation: Addison's disease, diabetes mellitus (type 1). Graves' disease, interstitial cystitis, lupus erythematous, multiple sclerosis and Hashimoto's thyroiditis. Allergic conditions include eczema, allergic rhinitis or coryza, hay fever, bronchial asthma, urticaria (hives) and food allergies, and other atopic conditions.

Non-limiting, exemplary cancers include: neoplasms, malignant tumors, metastases, or any disease or disorder characterized by uncontrolled cell growth such that it would be considered cancerous. The cancer may be a primary or metastatic cancer. Cancers include, but are not limited to, adult and pediatric acute lymphoblastic leukemia, acute myeloid leukemia, adrenocortical carcinoma. AIDS-related cancers, anal cancer, cancer of the appendix, astrocytoma, basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer. Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors. Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinemia, malignant fibrous histiocytoma, medulloblastoma, melanoma. Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma. Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is lung cancer, breast cancer, prostate cancer, colorectal cancer, gastric cancer, liver cancer, pancreatic cancer, brain and central nervous system cancer, skin cancer, ovarian cancer, leukemia, endometrial cancer, bone, cartilage and soft tissue sarcoma, lymphoma, neuroblastoma, nephroblastoma, retinoblastoma, or gonadal germ cell tumor.

As used herein, the term "treating" refers to the application or administration of the delivery vehicle. the ceramide-therapeutic agent complex, or the composition comprising such to a subject in need thereof. "A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., rodent (e.g., mouse or rat), primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). The non-human animal may be a male or female at any stage of development. The non-human animal may be a transgenic animal or genetically engineered animal.

In some embodiments, the subject is a companion animal (a pet). "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

In some embodiments, a "subject in need thereof" refers to a subject that needs treatment of a disease described herein.

Alleviating a disease includes delaying the development or progression of the disease, or reducing disease severity. Alleviating the disease does not necessarily require curative results. As used therein. "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrastemal, intrathecal, intralesional, and intracranial injection or infusion techniques. In addition, it can be administered to the subject via injectable depot mutes of administration such as using 1-, 3-, or 6-month depot injectable or biodegradable materials and methods.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1. Test if the Oligosaccharide Domain of GM) is Essential for Intracellular Trafficking and Cargo Transport Mucosal surfaces represent vast areas where host tissues are separated from the environment only by a delicate but highly effective single layer of columnar epithelial cells, joined by tight junctions that are impermeable to proteins and even small peptides. Proteins non-specifically taken up directly into the epithelial cell by endocytosis are generally transported to lysosomes for degradation. So far, the lack of rational and efficient methods to circumvent this barrier has prevented the application of most therapeutic proteins and peptides for mucosal drug delivery.

Endothelial cells also form vast and highly restrictive single cell thick barriers that separate most tissues from the blood stream. Except for the vasculature in the intestine, glomerulus, and liver, the healthy non-inflamed endothelial barrier strongly limits the permeability of large molecules; thus preventing access of many protein-based biologics to cells of many tissues—even when the therapeutic proteins are applied intravenously.

The pathway for large solutes (e.g., protein and peptide biologics) to cross simple epithelial and endothelial barriers with highly resistant intercellular tight junctions is by transcytosis—a process of transcellular membrane trafficking that connects one surface of polarized cells with the other (FIG. 1). It has been described that the GM1 glycosphingolipid crosses epithelial barriers by transcytosis and the structure of its ceramide domain dictates transport through this pathway. GM1 species containing non-native "short chain" fatty acids in the ceramide domain was shown to allow for more efficient transport across simple epithelial barriers, and some can release from the cell membrane back into solution after transcytosis. It was also found that the "short-chain" GM1 glycosphingolipids can carry therapeutic peptides (GLP-1) across the intestinal epithelial barrier to deliver them systemically. These in vivo studies show absorption far surpassing the best currently achieved for oral delivery of biologics.

It was found in non-polarized cells that GM1-ceramides containing "kinked" cis-unsaturated C18:1 or C16:1 fatty acids, or non-native "short chain" C12:0 to C4:0 fatty acids, enter the sorting/recycling endosome of epithelial cells for transport to various intracellular destinations: including the recycling pathway and retrograde pathway to Golgi and ER. These lipids do not traffic into the late endosome-lysosome pathway. In contrast, the GM1-sphingolipids with long saturated fatty acid chains (C16:0 or longer) sort efficiently into late endosomes and lysosomes (FIG. 19). The results are consistent with models for lipid sorting by molecular shape and membrane domains.

In polarized epithelial cells, another sorting event emerges from the sorting endosome and leads into the transcytotic pathway. This pathway allows for the short- or unsaturated GM1-ceramides to cross the cell to the opposite cell surface, thus breeching the epithelial barrier by transcytosis (FIG. 1). It has been found that GM1 glycolipids can carry the 80 kDa protein cholera toxin fully across polarized monolayers of intestinal epithelial cells in culture, implicating a function for this pathway in protein absorption across the intestine in vivo.

Based on these results, the idea that the glycosphingolipids may be harnessed as trafficking vehicles for biologic drug delivery was tested. A all D-isomer amino acid reporter-peptide carrying a reactive aminooxy C-terminal residue for coupling to sialic acid of the glycoceramide GM1, a biotin group for rapid and high affinity isolation, and an alkyne group for coupling to cargo (e.g., for detection via Alexa Fluor 488) was developed (FIG. 2).

Structure-function studies showed that certain novel short-chain ceramide species allowed for transcellular transport (transcytosis) of the peptide-GM1 fusion molecule across epithelial monolayers in vitro as assessed biochemically (FIG. 3) and morphologically (FIG. 21). Studies using chemical inhibitors and genetic depletion of genes required for transcytosis showed that the peptide-GM1 fusion molecules cross the epithelial monolayers by passing through the cell by transcytosis, and not around the cell by paracellular "leak" (FIG. 22).

When applied orally (by gastric gavage) to mice in vivo, the peptide-GM1 fusion molecules were absorbed across the intestine into the circulation as assessed in blood and in liver tissue (FIGS. 4A-4D). Uncoupled peptides, however, are not absorbed. The absorption of the peptide-GM1 fusion molecules in the nasal epithelium was observed, as assessed biochemically in blood, and morphologically by imaging (FIG. 23).

Translational studies were carried out using the incretin hormone GLP-1 as cargo. Human GLP1 is a cleavage product of proglucagon produced in pancreatic or intestinal enteroendocrine cells. Native GLP-1 possesses several physiological properties on glucose metabolism that make it an effective treatment for diabetes mellitus type II. There also are receptors for GLP-1 in the brain, and evidence that the molecule may operate in appetite control, suggesting other clinical applications. In this case, transport across the epithelial barrier is almost 100-fold above the GLP-1 peptide alone. Fusion of the peptide hormone to the lipid carrier causes a very modest loss of hormone function as assessed by dose response in bioassay shown in panel to right (fusion molecule in RED is about a half-log less potent but still functional in picomolar range). It was found that GLP-1 incretin function is retained after fusion to the oligosaccharide domain of GM1 (FIG. 5A) (half-log loss in activity). When tested in vitro, GLP-1 was transported across epithelial barriers by the short-chain GM1-species nearly 100-fold above that observed for the peptide alone (FIG. 5B).

Consistent with the in vivo studies using the reporter-peptide-GM1 fusion molecules, it was found that when applied to mice via gastric gavage, GLP-1-GM1 fusion molecules were absorbed and had effects over glucose metabolism, evidenced by reduced time to normalize blood sugar in glucose tolerance tests (FIG. 6). An assay was recently developed to confirm biochemically that the GLP-1-GM1 fusion molecules are absorbed into the blood (not shown). The GLP-1 peptide alone is not absorbed and has no detectable effect on glucose metabolism.

Another structural feature of GM1 that might play a role in trafficking is the extracellular oligosaccharide head group. Further described herein are studies designed to test if the oligosaccharide domain of GM1 is essential for intracellular trafficking and cargo transport. Simplifying the lipid carrier may be important to clinical translation. It is tested herein if a simple glycoceramide easily harvested from buttermilk can be used in place of GM1, and if the oligosaccharide domain of GM1 can be eliminated completely, thus defining a simplified core delivery molecule that can be fully and pragmatically synthesized.

Simplifying the glycoceramide structure would have two major significances. First, this would allow for total chemical synthesis of the molecules and permit easier translation to the clinic. Second, structural elements of the oligosaccharide head group that affect trafficking may be identified, enhancing the understanding of the structure-activity relationship for the glycosphingolipids, and aiding in design of new peptide linkers that recapture the lost functionalities.

Some functionality of the sugar head groups are anticipated. At minimum, the oligosaccharide domain of GM1 is expected to function by trapping the ceramide in the outer membrane leaflet, preventing flip-flop and rendering the molecule dependent on membrane trafficking for distribution within and across cells, or by shaping the molecule. Such functions, however, might be reproduced simply by attachment of peptide or protein cargo to the ceramide domain. Still, the oligosaccharide head group of GM1 might also participate in sorting reactions that drive GM1 trafficking. If so, it may be possible to design peptide linkers that recover such trafficking functions. The testing of the oligosaccharide domain and accommodation to its loss are the topics of this aim.

Initially, two simplified structural analogs of GM1 are tested: glucosylceramide (Glc-Cer-one sugar residue), and ceramide alone (no sugars). These lipids are commercially available with different ceramide structures (Avanti Polar Lipids). Because ceramide (Cer) and Glc-Cer lack a sialic acid, this necessitates an alternative chemical strategy to link peptides onto the ceramide headgroup. All lipids are coupled to the reporter peptide using copper-catalyzed "click" chemistry. Because Cer and Glc-Cer lack a sialic acid, this necessitates an alternative chemical strategy to link peptides onto the ceramide headgroup. Details of the chemical reactions are shown in FIG. 7. The primary hydroxyl located on the ceramide (or on glucose ring of Glc-Cer) are oxidized to react with peptides containing aminooxy reactive groups as in established method (12, 13). All compounds are confirmed for mass by MALDI mass spectrometry (or LC-MS) and NMR.

The transcytosis of Glc-Cer and Cer are tested in vitro using polarized cell lines T84, Caco2 and MDCK. Testing the new peptide-ceramide fusion molecules for transcytosis using the same methods described in FIG. 5. Due to a possibility of being less soluble, the lipids are complexed to BSA (1:1) as described in Pagano et al. (43).

Figure 8:
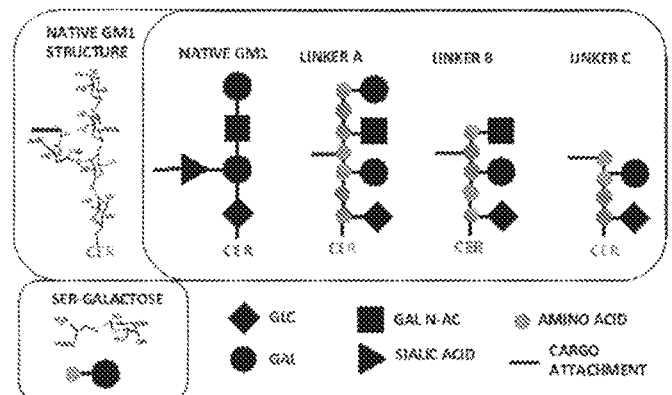
FIG. 8. GM1 oligosaccharide domain structure and replacement with approximated peptide-sugar linkers. The structure of the GM1 headgroup (Left) with the sialic acid site for coupling to cargo molecules (blue line). Linker peptides are synthesized via precursor building blocks of serine attached to different sugar types. Three different linkers are designed to test the minimal structure required.

If reporter peptide fusions to ceramide alone mimic the GM1-trafficking platform, it can be concluded that the sugar groups are dispensable, except perhaps for blocking the sphingolipid from membrane flip-flop to the inner leaflet, a function presumably accommodated by the peptide-linker and cargo. If the oligosaccharide domain contributes decisively to trafficking function (and thus are required), peptide linkers that would replace the functionality of the oligosaccharide domains in trafficking can be designed. Due to the inherent difficulty in synthesizing complex O-linked oligosaccharides onto lipids, pseudo-glycopeptide linkers are synthesized using backbone amino acids coupled to glucose, galactose or galactose-N-acetyl residues via serine side chains (44). FMoc-protected building block amino acids containing monosaccharides are commercially available and will be used for solid phase peptide synthesis of short linear peptides containing up to 4-5 sugar residues each (FIG. 8). Addition of the sugar groups may reproduce the overall "bulk" and strong hydrophilicity imparted by the endogenous GM1 oligosaccharide, or function to display glucose or galactose as ligands for extracellular lectins that could participate in the lipid sorting events—such as that proposed for galectin 3 in non-clathrin mediated endocytosis (41). When necessary, additional peptides are synthesized in a branched manner (as observed with the natural sialic acid residue), or cyclized to alter headgroup geometry to approximate the GM1 oligosaccharide. The transcytosis assay can be performed in a medium throughput manner, thus assess many different peptides constructs together.

If glycoceramide (single sugar) mimics results with the GM1-lipids, but ceramide alone does not, it can be concluded that the sugar groups contribute to glycosphingolipid sorting primarily by anchoring the molecules in the outer-leaflet of the membrane. In both cases, it is possible that simplified sphingolipids can substitute for GM1 (or with redesigned peptide-sugar linkers).

The ability of ceramide alone or Glc-Cer to function as the GM1-lipid platform allow more rapid translation to clinical application, as these molecules can be synthesized or readily purified from milk fats.

Example 2. Test if the Peptide Linker Between GM1 and Cargo can be Designed to Release the Cargo after or During Transcytosis Described herein is the design of a delivery vehicle that releases the cargo after transport. For instance, fusion of GM1 to the smaller peptide hormone GLP-1 causes a 3 to 8-fold loss of function. While still highly potent (pM activity) and physiologically relevant, the GLP-1-GM1 fusion molecule is still less potent than the native peptide. Here, two approaches to design the peptide linker so that it can release cargo from GM1 after uptake into the cell or after arrival in the basolateral endosome were tested. One approach involved the incorporation of an ester linkage in the peptide linker (as target for esterases increased at sites of inflammation. e.g., leukocyte esterase, or carboxylesterase hCE-2 that is specific to gastrointestinal endosomes) (1, 45); and the other involved incorporation of a cleavage motif for the endosomal protease furin (2-4).

Figure 9:
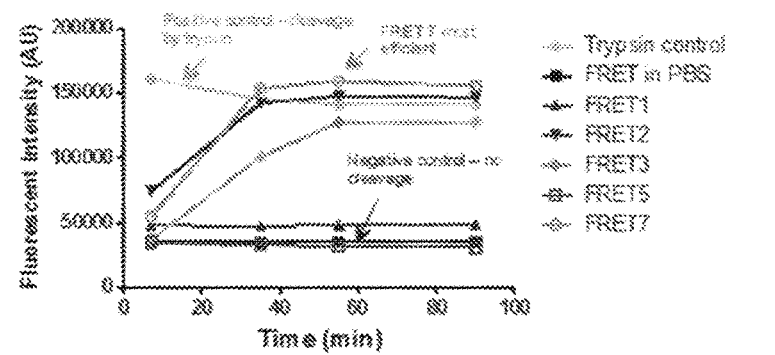
FIG. 9. Optimization of a furin cleavage motif for incorporation into the GM1-cargo linker peptide. A fluorescence energy transfer (FRET) based assay was designed by appending paired fluorophores at each end of the peptide to be tested. Cleavage of the peptide by recombinant purified furin was measured as increase in fluorescence (decrease in FRET quenching) in vitro, using buffer alone as negative control (no cleavage) and high dose trypsin as positive control (the furin motif can be cleaved by other serine proteases). The motif termed FRET 7 was most efficient.
Figure 9:
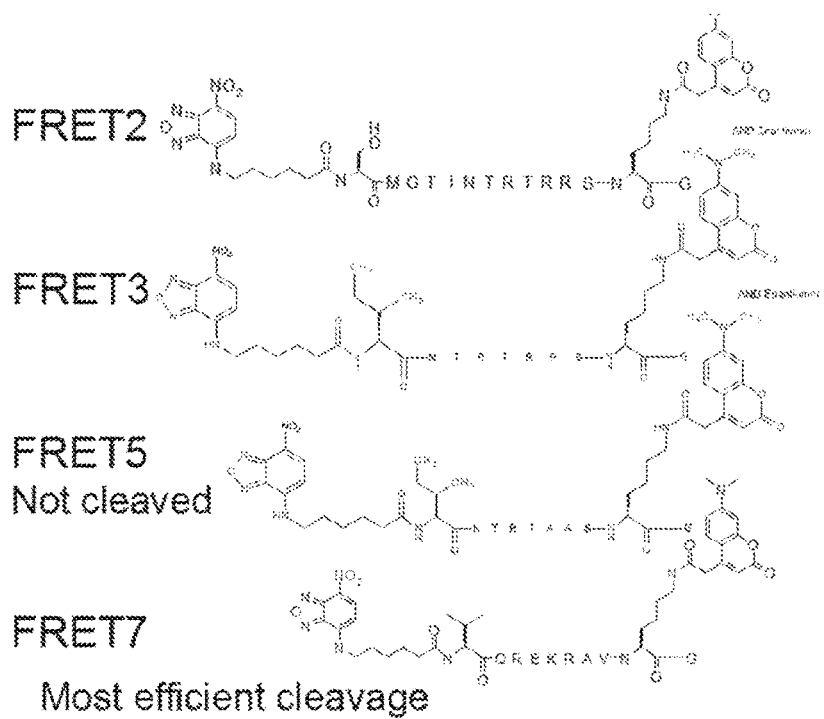
Figure 10:
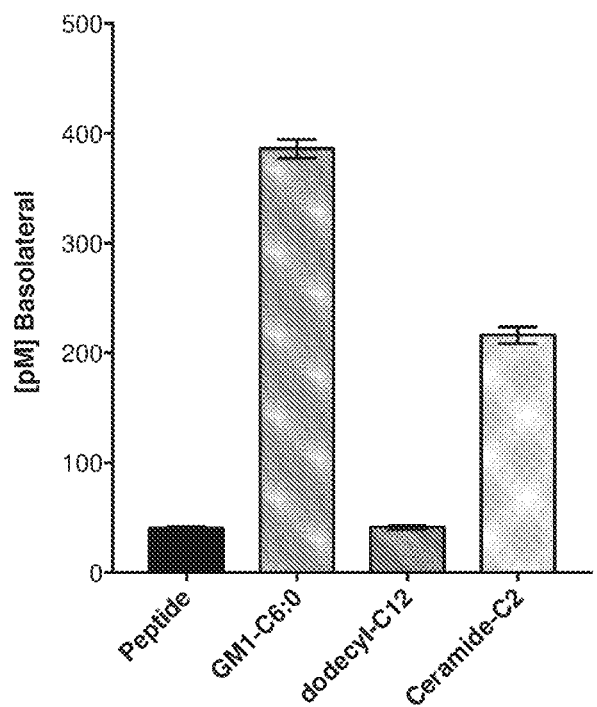
FIG. 10. Linkage to ceramide without sugars led to transcytosis across epithelial barriers in vitro. Linkage to fatty acid alone (dodecyl-C12) did not. Peptide alone did not cross the epithelial barrier, as expected.

Different furin cleavage motifs were tested for activity within the context of short peptide linker. The assay was designed as high-throughput using fluorescence energy transfer (FRET) by appending paired fluorophores at each end of the peptide to be tested. FIG. 9 shows identification of an optimal sequence (FRET 7) for further testing. This motif was incorporated into the linker system described herein and the peptide is synthesized, purified, and validated by mass spec in large quantities. It is ready for coupling to cargo and GM1 for testing in vitro and in vivo.

The FRET 7 furin cleavage motif or a cleavable ester linkage are incorporated into the reporter-peptide linker, and also with GLP-1 incorporated as cargo. The GM1-C12:0 species are used as a fusion partner because this lipid does not readily release from membranes and will provide a more sensitive approach to test this technology. The efficiency for cleavage are first tested in vitro using recombinant esterases or recombinant furin and analyzed by HPLC. If cleavage is confirmed, the fusion molecules are tested for efficiency of cargo transport across highly resistant T84 epithelial barriers (as described in FIG. 5). Control cargos are fused to GM1-C12:0 using non-cleavable linkers. The fusion molecules are applied to apical surfaces of T84 cells in the presence of serine protease inhibitors, BSA as serine-protease decoys, and ester-linked peptide decoys. Rates of transepithelial transport will be compared using non-cleavable peptide linkers as controls. An increase in transepithelial transport (or cytosolic delivery of cargo) above that achieved by the non-cleavable peptide linkers suggests that cleavable linker technologies are feasible.

REFERENCES

1. Zhang S, Ermann J. Succi M D. Zhou A, Hamilton MJ. Cao B. Korzenik J R, Glickman J N, Vemula P K, Glimcher L H, et al. An inflammation-targeting hydrogel for local drug delivery in inflammatory bowel disease. *Science translational medicine.* 2015; 7(300):300ra128.
2. Bohme D. and Beck-Sickinger A G, Drug delivery and release systems for targeted tumor therapy. *J Pept Sci.* 2015; 21(3):186-200.

3. Mayer G, Boileau G, and Bendayan M. The proprotein convertase furin colocalizes with caveolin-1 in the Golgi apparatus and endosomes of hepatocytes. *Cell Tissue Res.* 2004; 316 (1): 55-63.
4. Simmen T. Nobile M. Bonifacino J S, and Hunziker W. Basolateral sorting of furin in MDCK cells requires a phenylalanine-isoleucine motif together with an acidic amino acid cluster. *Mol Cell Biol.* 1999; 19(4):3136-44.
5. Maxfield F R, and McGraw T E, Endocytic recycling. *Nat Rev Mol Cell Biol.* 2004; 5(2):121-32.
6. Saslowsky D E, te Welscher Y M, Chinnapen D J, Wagner J S, Wan J, Kern E. and Lencer W I, Ganglioside GM1-mediated transcytosis of cholera toxin bypasses the retrograde pathway and depends on the structure of the ceramide domain. *Journal Of Biological Chemistry.* 2013; 288(36):25804-9.
7. Chinnapen D J, Hsieh W T, Te Welscher Y M, Saslowsky D E, Kaoutzani L. Brandsma E. D'Auria L, Park H. Wagner J S, Drake K R, et al. Lipid Sorting by Ceramide Structure from Plasma Membrane to ER for the Cholera Toxin Receptor Ganglioside GM1. *Developmental cell.* 2012; 23(3):573-86.
8. Truong-Le V. Lovalenti P M, and Abdul-Fattah A M. Stabilization Challenges and Formulation Strategies Associated with Oral Biologic Drug Delivery Systems. *Adv Drug Deliv Rev.* 2015:93 (95-108.
9. Degroote S. Wolthoorn J, and van Meer G. The cell biology of glycosphingolipids. *Semin Cell Dev Biol.* 2004; 15(4):375-87.
10. Simons K, and van Meer G. Lipid sorting in epithelial cells. *Biochemistry.* 1988; 27 (6197-202.
11. van Meer G, and Holthuis J C, Sphingolipid transport in eukaryotic cells. *Biochim Biophys Acta.* 2000; 1486(1): 145-70.
12. van Meer G, and Vaz W L, Membrane curvature sorts lipids. Stabilized lipid rafts in membrane transport. *EMBO Rep.* 2005; 6(5):418-9.
13. Mukherjce S. and Maxfield F R, Role of membrane organization and membrane domains in endocytic lipid trafficking. *Traffic.* 2000; 1(3):203-11.
14. Mukherjee S, Soe T T, and Maxfield F R, Endocytic sorting of lipid analogues differing solely in the chemistry of their hydrophobic tails. *Journal Of Cell Biology.* 1999; 144 (1271-1284).
15. Brown D A, Lipid rafts, detergent-resistant membranes, and raft targeting signals. *Physiology* (Bethesda, Md. 2006:21 (430-9.
16. Simons K, and Ehehalt R. Cholesterol, lipid rafts, and disease. *J Clin Invest.* 2002; 110(5):597-603.
17. Simons K, and Vaz W L, Model systems, lipid rafts, and cell membranes. *Annu Rev Biophys Biomol Struct.* 2004; 33 (269-95.
18. Tsai B, Rodighiero C. Lencer W I, and Rapoport T. Protein disulfide isomerase acts as a redox-dependent chaperone to unfold cholera toxin. *Cell.* 2001; 104 (937-48.
19. Lencer W I. and Tsai B. The intracellular voyage of cholera toxin: going retro. *Trends Biochem Sci.* 2003; 28(12):639-45.
20. Mayor S, Presley J F, and Maxfield F R, Sorting of membrane components from endosomes and subsequent recycling to the cell surface occurs by a bulk flow process. *Journal Of Cell Biology.* 1993; 121(6):1257-69.
21. Tuma P L, and Hubbard A L, Transcytosis: crossing cellular barriers. *Physiol Rev.* 2003:83(3):871-932.
22. Tencer W I. Moe S, Rufo P A, and Madara J L, Transcytosis of cholera toxin subunits across model human intestinal epithelia. *Proc Natl Acad Sci USA.* 1995; 92 (10094-8.
23. Kieffer T J, and Habener J F. The glucagon-like peptides. *Endocr Rev.* 1999; 20 (876-913.
24. Heppner K M, and Perez-Tilve D. GLP-1 based therapeutics: simultaneously combating T2DM and obesity. *Front Neurosci.* 2015; 9 (92.
25. Mendieta Zeron H. Dominguez Garcia M V, Camarillo Romero Mdel S. and Flores-Merino M V, Peripheral Pathways in the Food-Intake Control towards the Adipose-Intestinal Missing Link. *Int J Endocrinol.* 2013; 2013 (598203.
26. te Welscher Y M, Chinnapen D J, Kaoutzani L, Mrsny R J, and Lencer W1. Unsaturated glycoceramides as molecular carriers for mucosal drug delivery of GLP-1. *Journal of controlled release: official journal of the Controlled Release Society.* 2014; 175 (72-8.
27. Chan H M, Jain R. Ahren B, Pacini G. and D'Argenio D Z, Effects of increasing doses of glucagon-like peptide-1 on insulin-releasing phases during intravenous glucose administration in mice. *Am J Physiol Regul Integr Comp Physiol.* 2011:300 (5): R1126-33.
28. Burmeister M A, Bracy D P, James F D, Holt R M, Ayala J, King E M, Wasserman D H, Drucker D J, and Ayala J E, Regulation of glucose kinetics during exercise by the glucagon-like peptide-1 receptor. *J Physiol.* 2012; 590 (Pt 20):5245-55.
29. Ewart-Toland A. Mounzih K, Qiu J, and Chehab F F. Effect of the genetic background on the reproduction of leptin-deficient obese mice. Endocrinology. 1999:140(2): 732-8.
30. Miranda L P, Winters K A, Gegg C V, Patel A, Aral J, Long J, Zhang J, Diamond S. Guido M. Stanislaus S, et al. Design and synthesis of conformationally constrained glucagon-like peptide-1 derivatives with increased plasma stability and prolonged in vivo activity. *Journal of medicinal chemistry.* 2008:51(9):2758-65.
31. Bird G H, Boyapalle S, Wong T. Opoku-Nsiah K, Bedi R, Crannell W C, Perry A F, Nguyen H, Sampayo V. Devareddy A, et al. Mucosal delivery of a double-stapled RSV peptide prevents nasopulmonary infection. *J Clin Invest.* 2014; 124(5):2113-24.
32. Walensky L D, and Bird G H, Hydrocarbon-stapled peptides: principles, practice, and progress. *Journal of medicinal chemistry.* 2014:57(15):6275-88.
33. Spickermann G M, Finn P W, Ward E S, Dumont J. Dickinson B L, Blumberg R S, and Lencer W I, Receptor-mediated immunoglobulin G transport across mucosal barriers in adult life: functional expression of FcRn in the mammalian lung. *J Exp Med.* 2002:196(3):303-10.
34. Abbott N J, Blood-brain barrier structure and function and the challenges for CNS drug delivery. *Journal of inherited metabolic disease.* 2013; 36(3):437-49.
35. van Bloemendaal L. Ten Kulve J S, la Fleur S E, Ijzerman R G, and Diamant M. Effects of glucagon-like peptide 1 on appetite and body weight: focus on the CNS. *J Endocrinol.* 2014; 221 (1): T1-16.
36. Frick M. Bright N A, Riento K, Bray A. Merrified C. and Nichols B J, Coassembly of flotillins induces formation of membrane microdomains, membrane curvature, and vesicle budding. *Curr Biol.* 2007:17(13):1151-6.
37. Glebov OO. Bright N A, and Nichols B J, Flotillin-1 defines a clathrin-independent endocytic pathway in mammalian cells. *Nat Cell Biol.* 2006; 8(1):46-54.

38. Langhorst M F, Reuter A, Jaeger F A, Wippich F M, Luxenhofer G, Plattner H, and Stuermer C A, Trafficking of the microdomain scaffolding protein reggie-1/flotillin-2. *Eur J Cell Biol.* 2008; 87(4):211-26.

39. Langhorst M F, Reuter A. and Stuermer C A, Scaffolding microdomains and beyond: the function of reggie/flotillin proteins. *Cell Mol Life Sci.* 2005; 62 (19-20):2228-40.

40. Morrow I C, and Parton R G, Flotillins and the PHB domain protein family: rafts, worms and anaesthetics. *Traffic.* 2005; 6(9):725-40.

41. Lakshminarayan R. Wunder C, Becken U, Howes M T, Benzing C. Arumugam S, Sales S. Ariotti N, Chambon V. Lamaze C. et al. Galectin-3 drives glycosphingolipid-dependent biogenesis of clathrin-independent carriers. *Nat Cell Biol.* 2014; 16(6):595-606.

42. Johannes L. Parton R G, Basscreau P, and Mayor S. Building endocytic pits without clathrin. *Nat Rev Mol Cell Bial.* 2015; 16(5):311-21.

43. Pagano R E, and Martin O C. A series of fluorescent N-acylsphingosines: synthesis, physical properties, and studies in cultured cells. *Biochemistry.* 1988; 27(12): 4439-45.

44. Jones E M, and Polt R. CNS active O-linked glycopeptides. *Front Chem.* 2015; 3 (40.

45. Imai T, and Ohura K. The role of intestinal carboxylesterase in the oral absorption of prodrugs. *Curr Drug Metab.* 2010; 11(9):793-805.

Example 3. Fatty Acid Length & Double Bond Positioning Dictate Endosomal Sorting of Glycosphingolipids The ceramide structure plays a decisive role in determining the cellular fate of glycosphingolipids after endocytosis—explained by their propensity to sort into highly curved tubules and buds emerging from the sorting endosome. It was tested herein whether glycosphingolipid sorting depends on molecular shape or on assembly into nano-domains (or both). GM1 species with saturated long chain fatty acids might a higher propensity to self-assemble with cholesterol into nano-domains. These domains might be recognized by cellular factors and sorted into the degradative pathway; preventing entering the recycling endosomal tubules.

To investigate the role of double bond positioning & hydrocarbon chain length of the ceramide fatty acid in lipid packing and subsequent differential endosomal sorting, GM1 isoforms with identical oligosaccharide head groups but ceramides of different endogenous structure were synthesized, by systematically increasing length and double bond position (C12:0 to C26:1).

Figure 17:
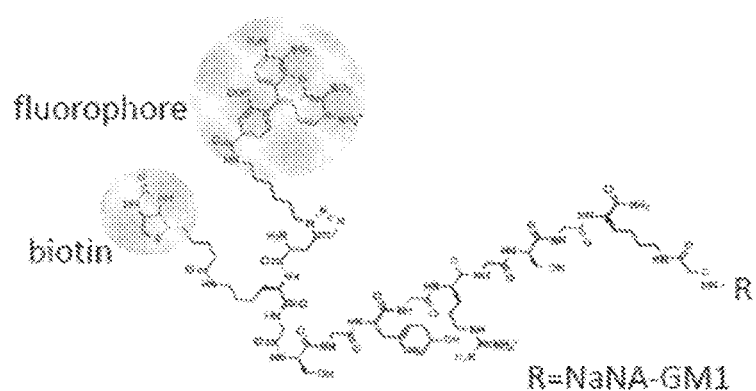
FIG. 17 Functionalization of GM1 species.

The GM1 species with different ceramide structures were functionalized with a D-amino acid reporter peptide, containing a biotin and fluorophore group. Alternatively, a fluorophore was directly onto the sialic acid of the sugar head group. Lipids were purified by HPLC and structures validated by LC/MS (FIG. 17).

Figure 18:
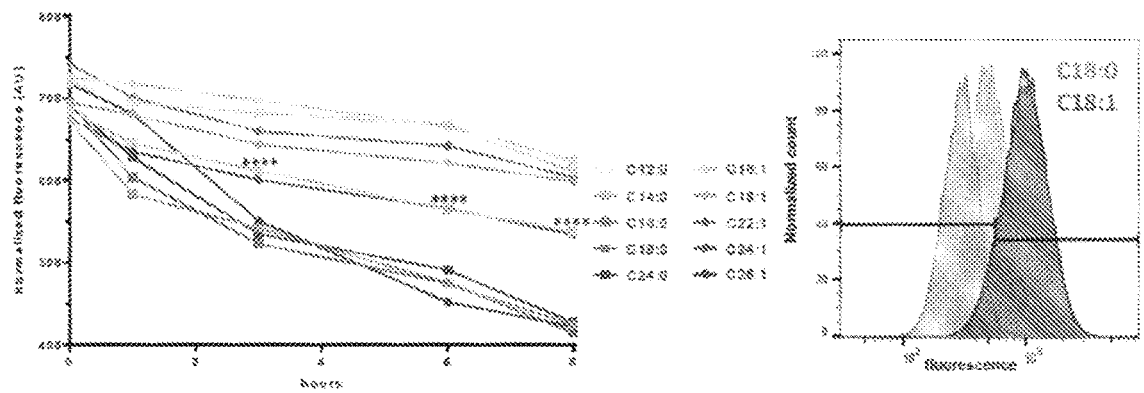
FIG. 18. Intracellular lipid trafficking—plasma membrane depletion dynamics of GM1 shows transport to the lysosome for some GM1 species.

Surface GM1 at steady state depends on lipid-sorting into highly curved tubules of the recycling pathway and this can be detected using fluorescent avidin probes. GM1 with saturated longer chain (>C14:0) fatty acid or long chain unsaturated fatty acid (>C24:1) are depleted from the plasma membrane, presumably sorted to the lysosome, suggesting inefficient entry into sorting tubules. GM1 containing a ceramide with C14:0 or C24:1 fatty acid have intermediate phenotype (FIG. 18).

Figure 19:
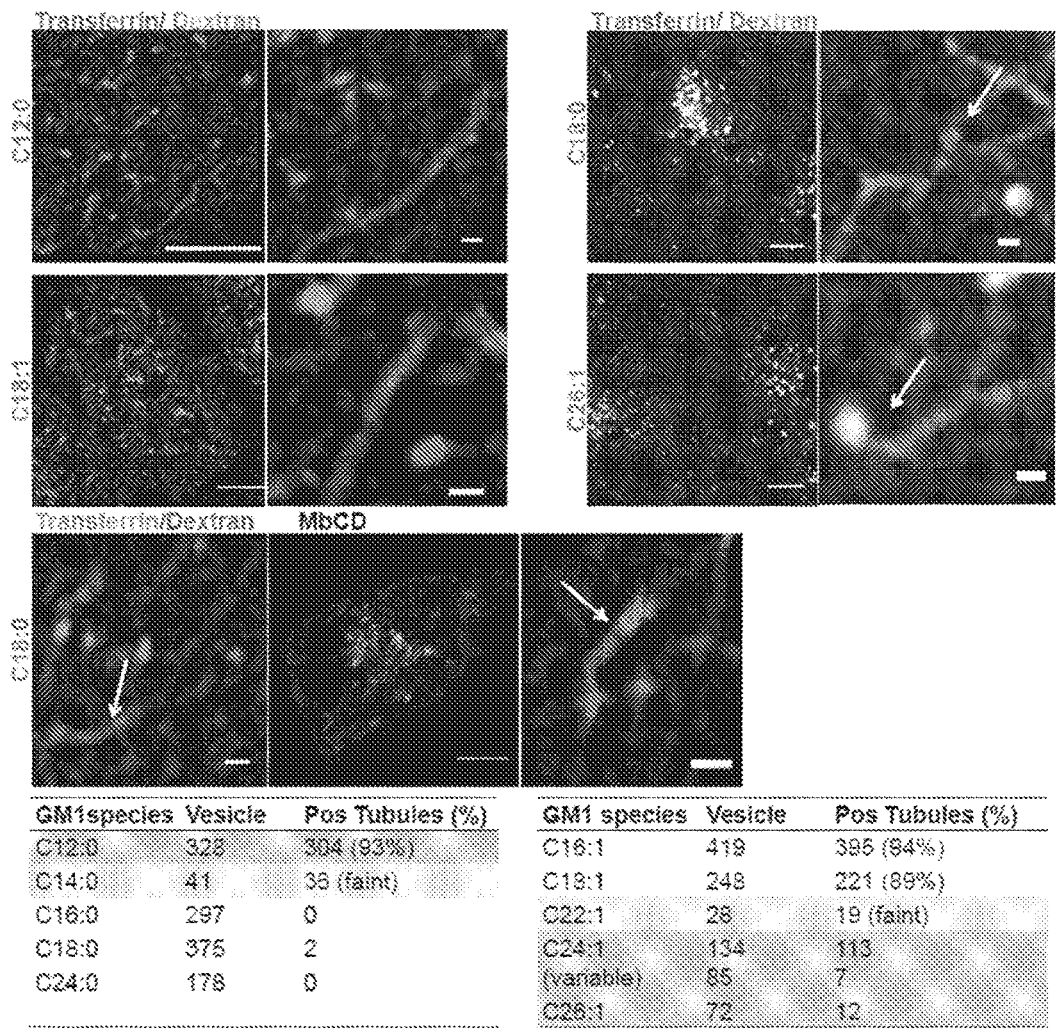
FIG. 19. Live cell direct fluorescence images of different GM1 species in sorting endosomes and sorting endosome tubules. Table quantifies degree of entry into sorting tubules for the different GM1 species.

Fluorescently-labeled GM1 in sorting tubules emerging from early endosomes (labeled with dextran and TFnR) was measured directly in A431 cells and quantified. GM1 with short (<C14:0) or unsaturated (<C24:1) fatty acids escaped the degradative pathway and enter recycling endosomal tubules. Depletion of cellular cholesterol by MbCD releases GM1 species with long (>C14:0, ≥C24:1) fatty acids into recycling endosomal tubules (FIG. 19).

Figure 20:
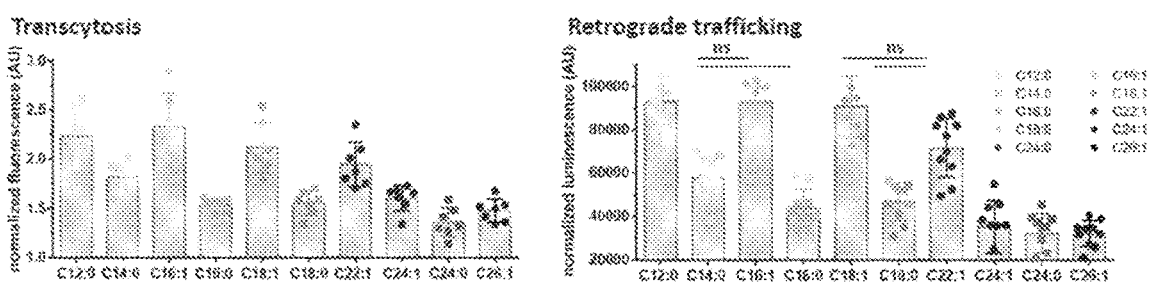
FIG. 20. Intracellular lipid sorting-transcytosis and retrograde trafficking. Shows how the position of the double bond influences entry into endosome sorting tubules that traffic across the cell by transcytosis or retrograde into the ER.
Figure 21:
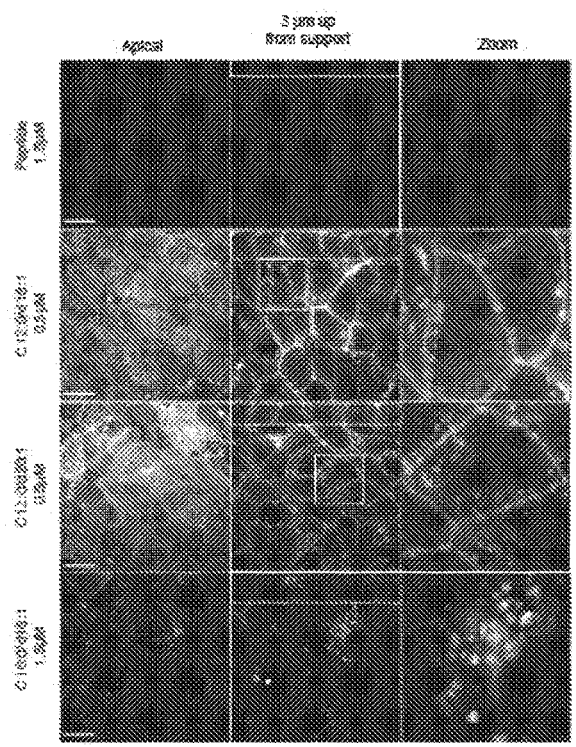
FIG. 21. Confocal fluorescence images of transcytosis in MDCK polarized cells. Only the short chain GM1 C12:0 species were transcytosed.
Figure 22:
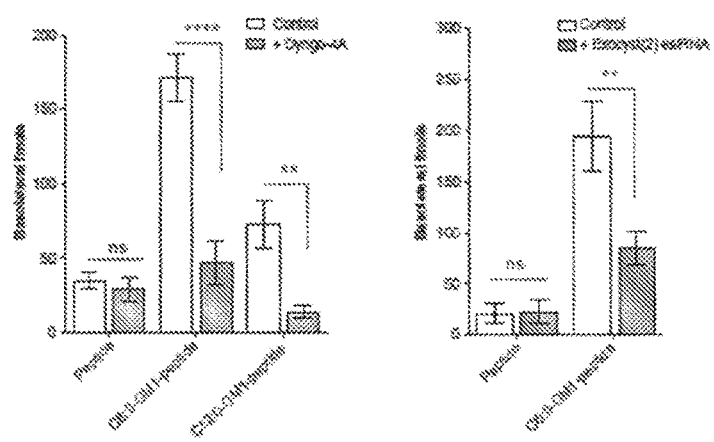
FIG. 22. Knockdown or inhibition of cellular machinery involved in transcytosis by Dyngo-4a chemical inhibition (for Dynamin, left panel), and gene knockdown by siRNA for Exocyst2 for the exocyst complex (right panel).
Figure 23:
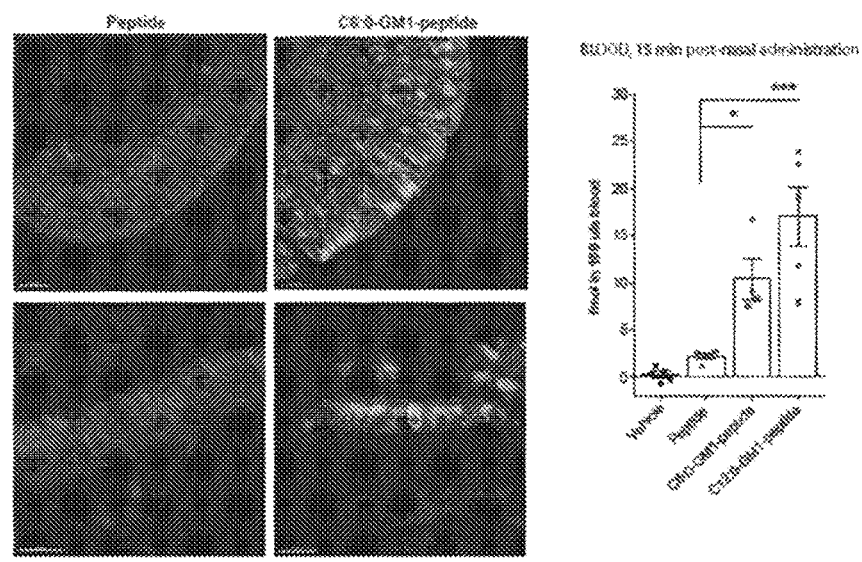
FIG. 23. Immunostaining images of C6-GM1 peptide or peptide alone transported across mouse nasal epithelium by 2-photon microscopy (left) and analysis of blood by streptavidin pull-down assay (right).
Figure 24A:
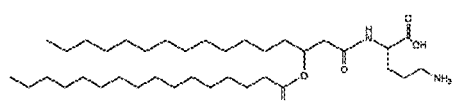
FIGS. 24A-24H. Ceramide analogs.
Figure 24B:
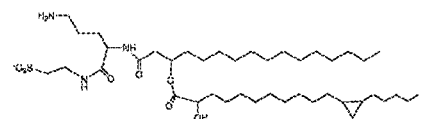
Figure 24C:
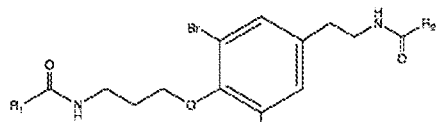
Figure 24D:
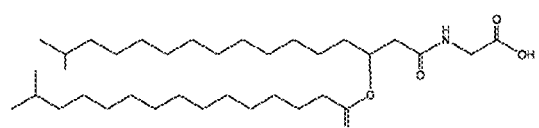
Figure 24E:
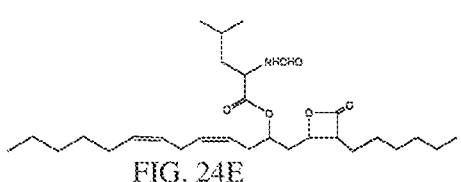
Figure 24F:
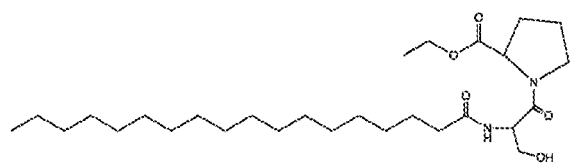
Figure 24G:
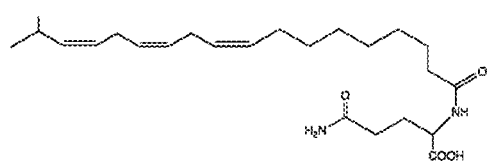
Figure 24H:
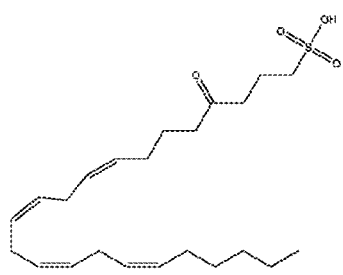
Figure 25A:
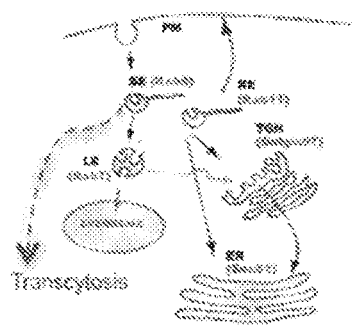
FIGS. 25A-25C. Confocal fluorescence microscopy images of lysosomal transport of GM1-peptides.
Figure 25B:
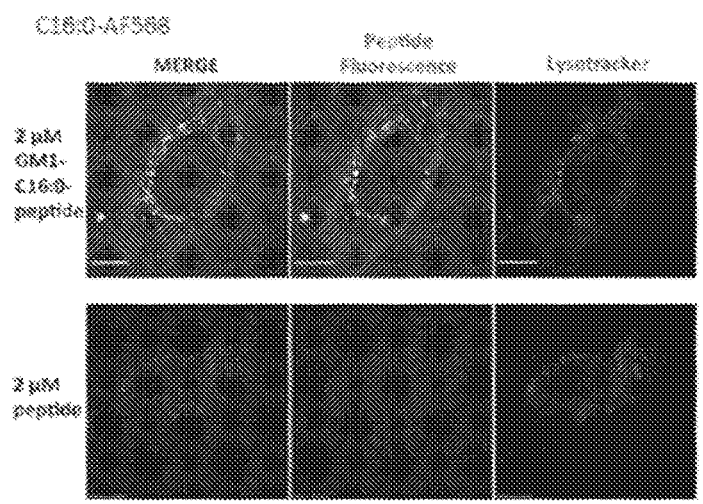
Figure 25C:
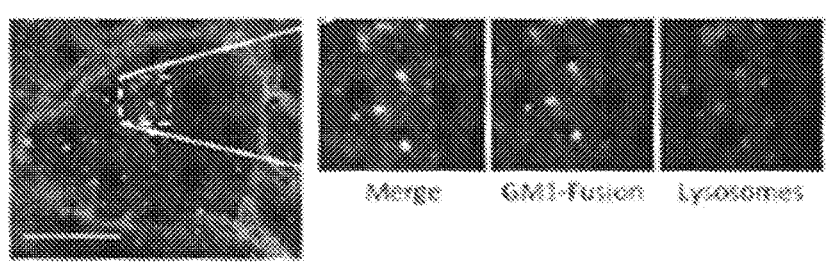

Two additional endocytic pathways depend upon sorting into highly curved tubules—transcytosis and retrograde, providing other quantitative measures for GM1 entry into sorting tubules. Transcytosis of individual GM1 species were measured in polarized MDCK cells detecting apical to basolateral transport of GM1 with a fluorescent avidin probe. Retrograde trafficking of individual GM1 species was measured using cAMP after intoxification by cholera toxin as read out in GM1 negative cell lines. The toxin must traffic retrograde to the ER to induce cAMP. GM1 with longer chain fatty acids (≥C14:0) or ceramides containing a mono-unsaturated fatty acid (≥C22:1) inefficiently enter sorting tubules and (presumably) are retained in the lysosomal pathway (FIG. 20). The position of the unsaturated bond suggests a decisive factor may be interaction with cholesterol.

Methods of Examples 1-3

Synthesis of Peotide-GM1 Conjugates

A short reporter peptide (all-D isomer) was synthesized and chemically linked onto the headgroup of ceramide lipid containing a C2:0 fatty acid tail. The chemistry to do this was very difficult due to the nature of the components and insolubility on standard solvents. Many different approaches had been tried a strategy that worked well was found. The 3-step synthetic approach is described herein.

Step 1: Oxidation of C2-Ceramide

Figure 11:
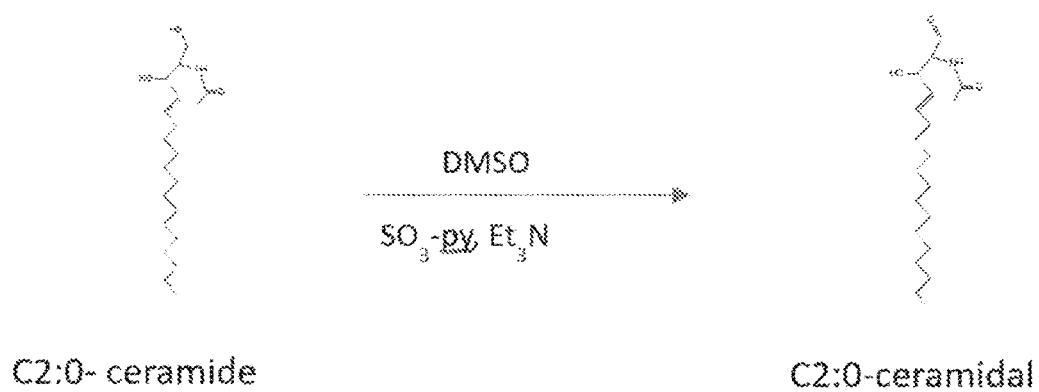
FIG. 11. Oxidation of C2-Ceramide. A method called "Parikh-Doering" oxidation was used to oxidize the head group of ceramide to a reactive aldehyde in organic solvent.

A method called "Parikh-Doering" oxidation was used to oxidize the headgroup of ceramide to a reactive aldehyde in organic solvent. Reaction mixture contains: (1) SO3Py: 190-400 mg/mL in dry DMSO; (2) C8 glucosylceramide: 0.2-0.6M solution in dry DMSO with Triethylamine; and (3) Triethylamine: 7-17 equivalents. The resulting product was purified by solvent extraction and dried in a speed vac (FIG. 11).

Step 2: Reaction of Peptide Containing Aminooxy to the Aldehyde Group

Figure 12:
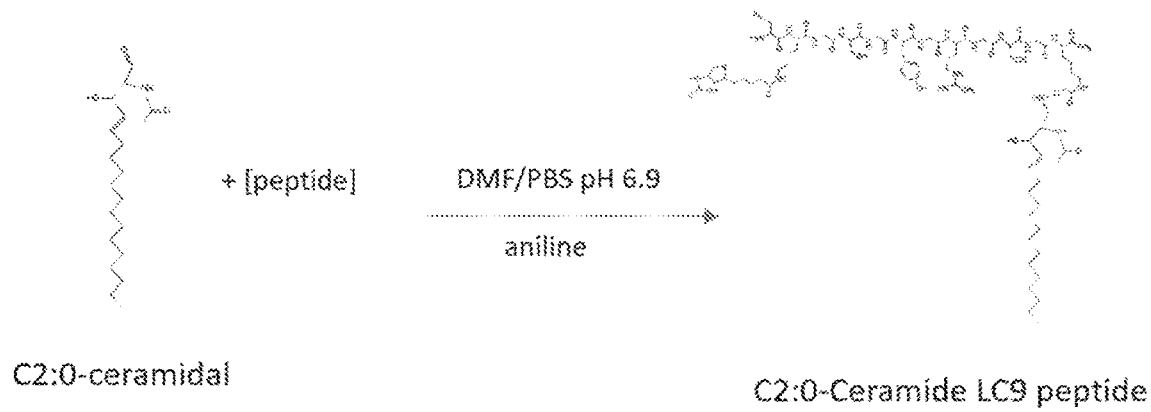
FIG. 12. Reaction of peptide containing aminooxy to the aldehyde group. The "LC9" (D-isomer) linker peptide was coupled using oxime-mediated reductive amination. LC9-sequence: [alkyne]-[lys-bio]-GSGYGRGSG-[lys-aoa].

The "LC9" (D-isomer) linker peptide was coupled using oxime-mediated reductive amination (FIG. 12) in 80% DMF in 20% PBS pH6.9 in 500 µL. The reaction mixture contained 471 nmoles peptide, 1.642 nmoles oxidized ceramide, and 1 µL aniline. After overnight incubation, 5 mM sodium cyanoborohydride was added to reduce the oxime bond formed and to make it a permanently stable bond.

Figure 13A:
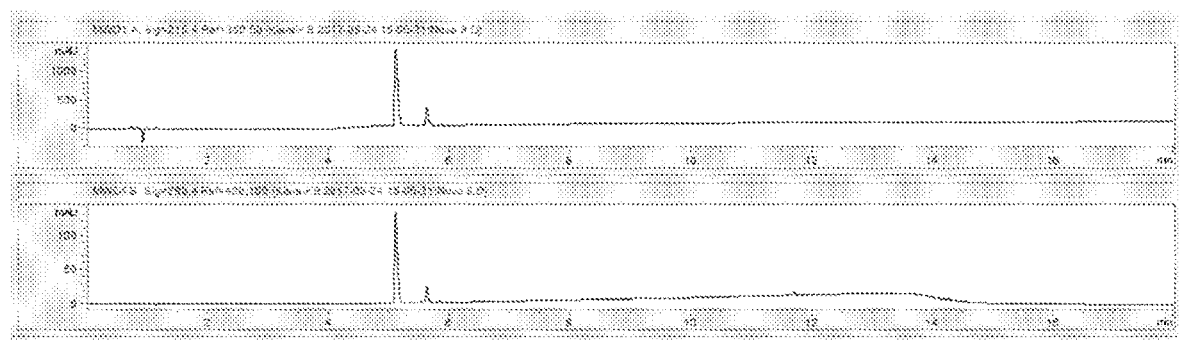
FIGS. 13A-13D. HPLC chromatograms of the products generated in FIG. 12.
Figure 13B:
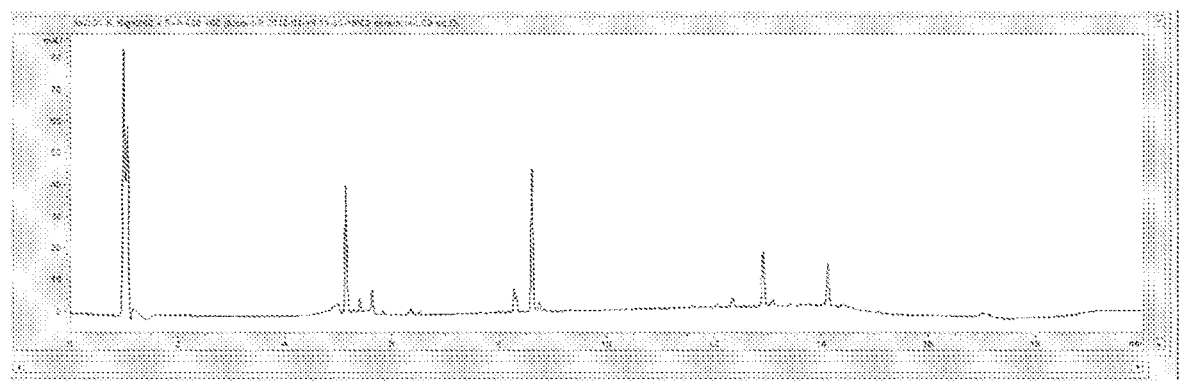
Figure 13C:
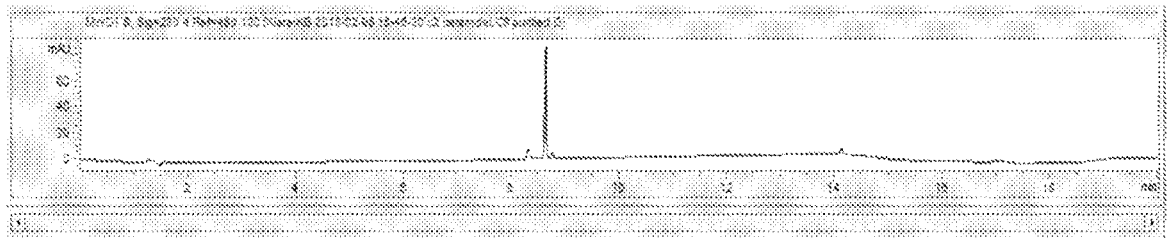
Figure 13D:
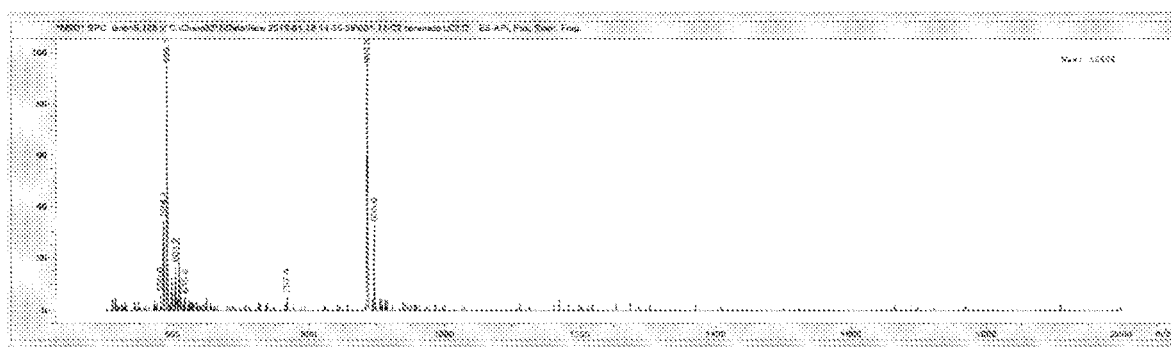

The resulting crude peptide-ceramide conjugates or purified conjugates (60% yield) were analyzed by HPLC (FIGS. 13A-13C). The products were also analyzed by mass spectrometry to confirm the presence of the peptide-ceramide conjugates (FIG. 13D).

Step 3: Copper Click Reaction of Alexa Fluor 488 to Ceramide-Peptide Conjugate

Figure 14:
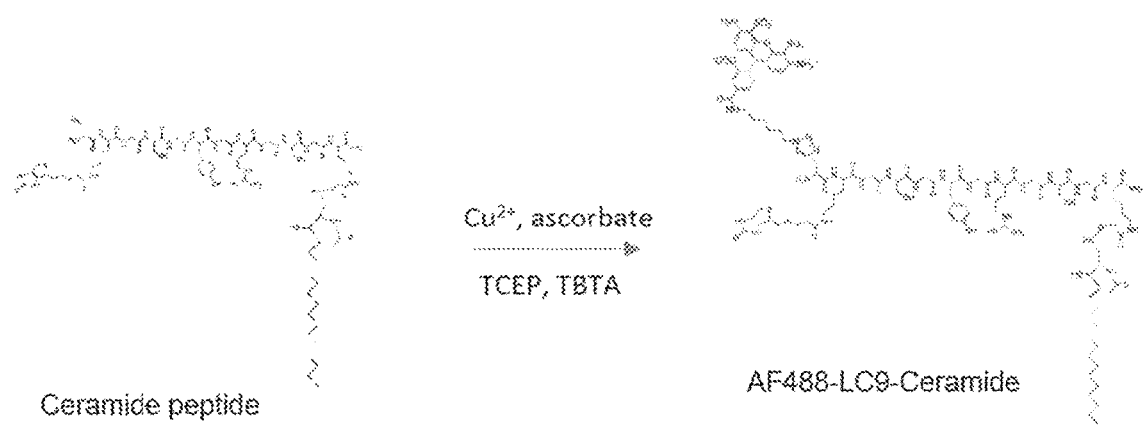
FIG. 14. Copper click reaction of Alexa Fluor 488 to ceramide-peptide conjugate.
Figure 15:
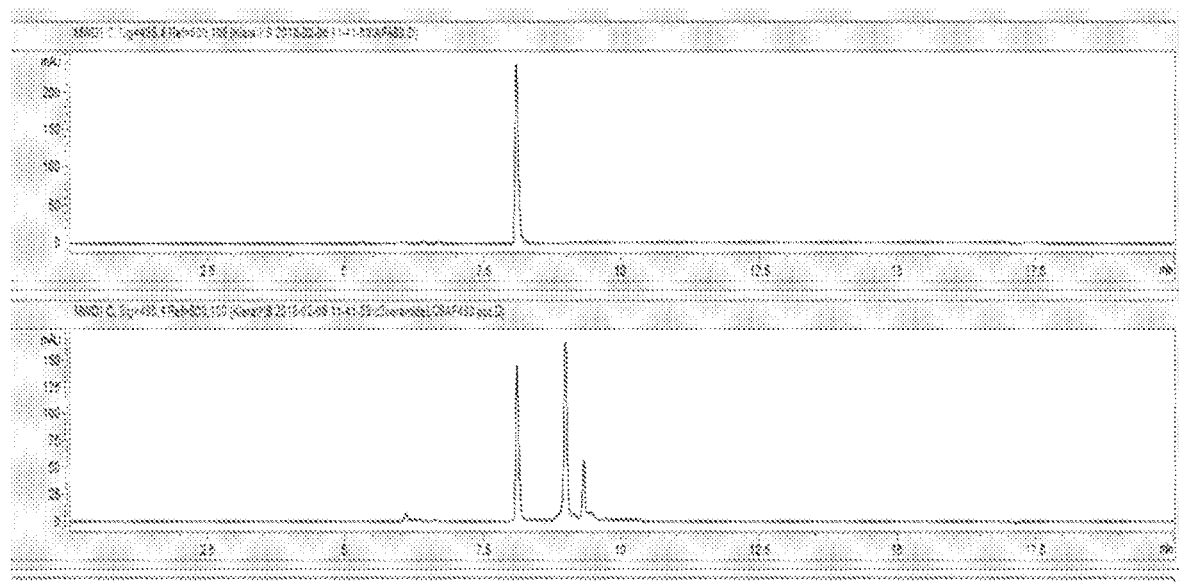
FIG. 15. HPLC chromatograms of the ceramide-peptide conjugated prepared in FIG. 14.
Figure 16:
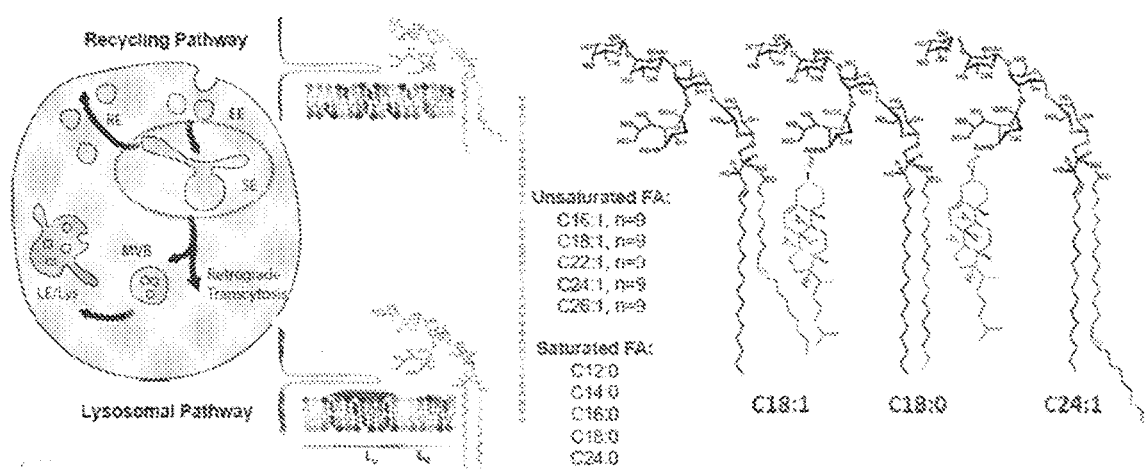
FIG. 16. Investigating the role of double bond positioning & hydrocarbon chain length of the ceramide fatty acid in lipid packing and subsequent differential endosomal sorting. GM1 isoforms with identical oligosaccharide head groups but ceramides of different endogenous structure, by systematically increasing length and double bond position (C12:0 to C26:1) were synthesized. Partially adopted from Arumugam et al., Essays in Biochemistry 57(1):109-119, incorporated herein by reference.

Alexa Fluorophore containing an azide reactive group was reacted to the peptide-ceramide conjugate via the N-terminal alkyne using Huisgen copper-catalyzed cycloaddition chemistry (FIG. 14). Briefly, Ceramide-peptide conjugate at 186 nmoles were reacted to 279 nmoles fluorophore in 50 mM Tris-Cl pH8, containing 100 mM ascorbate, 5 mM copper sulfate. 0.06 mM TBTA and 1 mM TCEP. The products were analyzed and purified by semi-preparative HPLC (FIG. 15). Final molecular weight of the produce was 2,425.1 Da Transcytosis in MDCK Cells The in vitro transport (transcytosis) of the peptide-GM1 conjugates across a monolayer of MDCK cells, and in vivo transport across an intestinal or nasal barrier into the blood are assessed. The peptide alone are used as negative controls, and the GM1 analogs as positive controls. C6, and C12 fatty acid analogs of ceramide were also included in the experiments as direct comparisons to the GM1 and GM3 species.

MDCK cells were seeded in 0.33 $cm^2$ inserts 3 days prior in media containing HBSS and 100 mM defatted BSA. Electrical resistance was checked on day of experiment.

Test Samples 1) peptide Control
2) GM1-C6:0-peptide
3) Peptide-C12 fatty acid
4) Ceramide-C2-

Media Preparation

Make: 27 mL T84-SF PLUS 1% dfBSA (add 270 mg dfBSA to 27 mL)
Make: 500 uL×50 samples=25 mL T84-SF PLUS 0.1% dfBSA (add 25 mg to 25 mL)

Transwell Assay

1) Check electrical resistance by EVOM.
2) Prepare stock solutions above.
3) Wash cells apical and basolateral with HBSS, without FBS. (dunk method)
4) EVOM the cells.
5) Replace apical with HBSS+0.1 uM dfBSA, basolateral with HBSS+1% dfBSA.
6) Incubate again for 20 minutes. Re-check EVOM.
7) Wait another 20 minutes and remove/replace apical with 200□L compound.
8) Continue incubation for 3 hours total.
9) Remove apical media to tubes.
10) Replace with apical media and recheck EVOM final.
11) Remove basolateral media to eppendorf tubes on ice.

Pull-down Assay

1) Washed Stretavidin Magnetic beads with TBS-T 4×, to remove azide.
2) Resuspend heads in 800 uL TBS then aliquoted 50 uL out to each tube
3) Add 1000 μL to streptavidin heads overnight at 4° C. with rotation O/N covered in foil.
4) Remove media and wash 3×TBS-T.

5) Elute by addition of 220 ul 95% Formamide. 10 mM EDTA 0.4 mg/ml biotin—2 min@65° C.
6) Pipetted 100 uL of each sample×2 on 96 well plate
7) Fluorescence was read out on a microplate reader for Fluorescein channel, and against a standard curve.

Example 4. Pharmacokinetics and Bioavailability of Peptide-GM1-C6:0 Fusion

Figure 26:
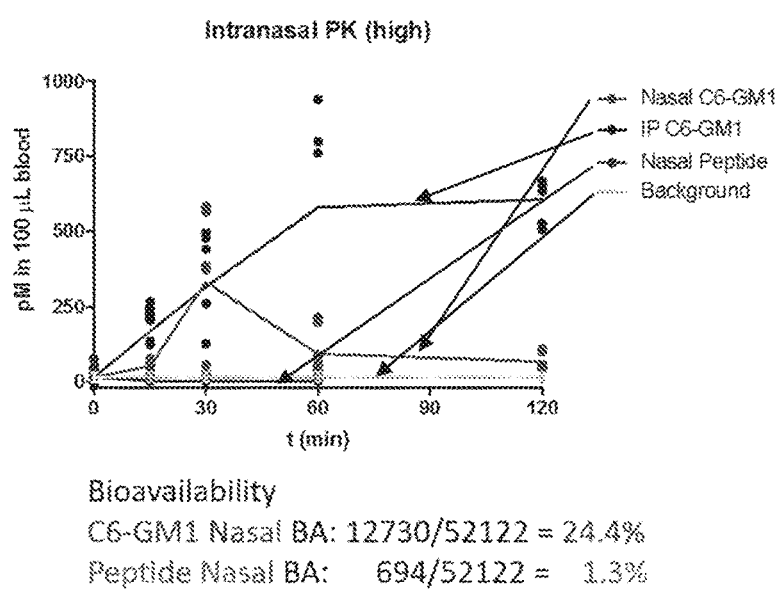
FIG. 26 shows the nasal bioavailability of a peptide fused to GM1-6. Apparent bioavailability for peptide fused to GM1-C6:0 was 24.4% compared to the same molecule injected intraperitoneally. Bioavailability of peptide alone was 1.3% compared to the for peptide fused to GM1-C6:0 injected intraperitoneally.

The bioavailability of the peptide-GM1-C6:0 fusion molecule when applied nasally to mice and the pharmacokinetics are shown in FIG. 26 (means of two independent experiments). The dose was 2.5 nmol/kg for 7 week old C57B/6J with an intranasal administration volume of 10 μL and an intraperitoneal injection volume of 200 μL. Nasal bioavailability of C6-GM1 is 24.4%, and nasal bioavailability of the peptide alone is 1.3%. The 24% absorption compared to intraperitoneal injection of the same molecule is high for mucosal absorption of therapeutic peptides.

Figure 32A:
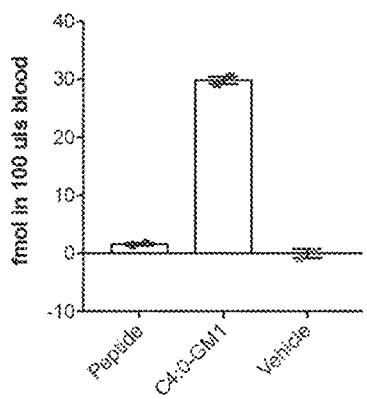
FIGS. 32A-32C show that serum half-life is strongly prolonged by fusion to GM1-C4:0.
Figure 32B:
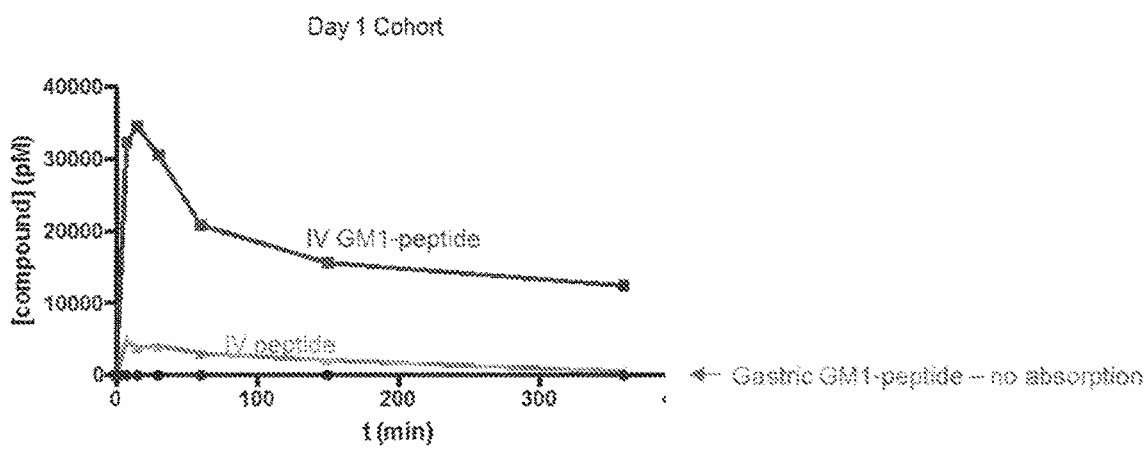
Figure 32C:
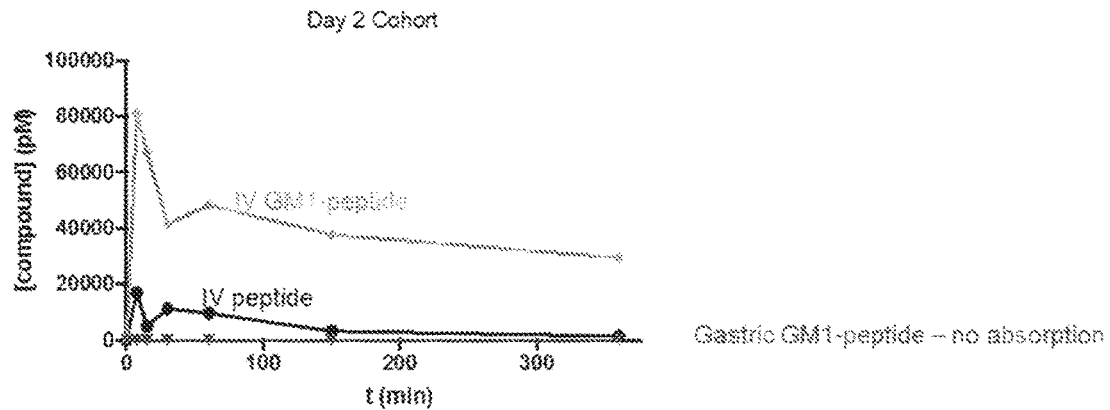

Next, the bioavailability and pharmacokinetics of a peptide fused to GM-C4:0 was tested in vivo in rat. The fusion molecule was validated in mice before the experiment (FIG. 32A). The peptide alone or the peptide-GM1-C4:0 conjugated was administered to rat via gastric route or via intravenous injection. The result showed that there was no adsorption of gastric peptide-GM1-C4:0 conjugate. However, serum half-life of the peptide was strongly prolonged by fusing the peptide to GM1-C4:0, which is consistent with protection against degradation or excretion by GM1-dependent trafficking into recycling endosomes of endothelial and other cell types (liver, lymphocytes, spleen, etc.). The results showed that, on day one after intravenous injection, the level of peptide-GM1-C4 fusion in rat serum was 5.6 nmol/kg and the level of peptide alone in rat serum was 10.8 nmol/kg (FIG. 32B). On day two after intravenous injection, the level of peptide-GM1-C4 fusion in rat serum was 14.4 nmol/kg and the level of peptide alone in rat serum was 12.8.8 nmol/kg (FIG. 32C).

Example 5. Ceramides and Analogs as Delivery Vehicles

Figure 27:
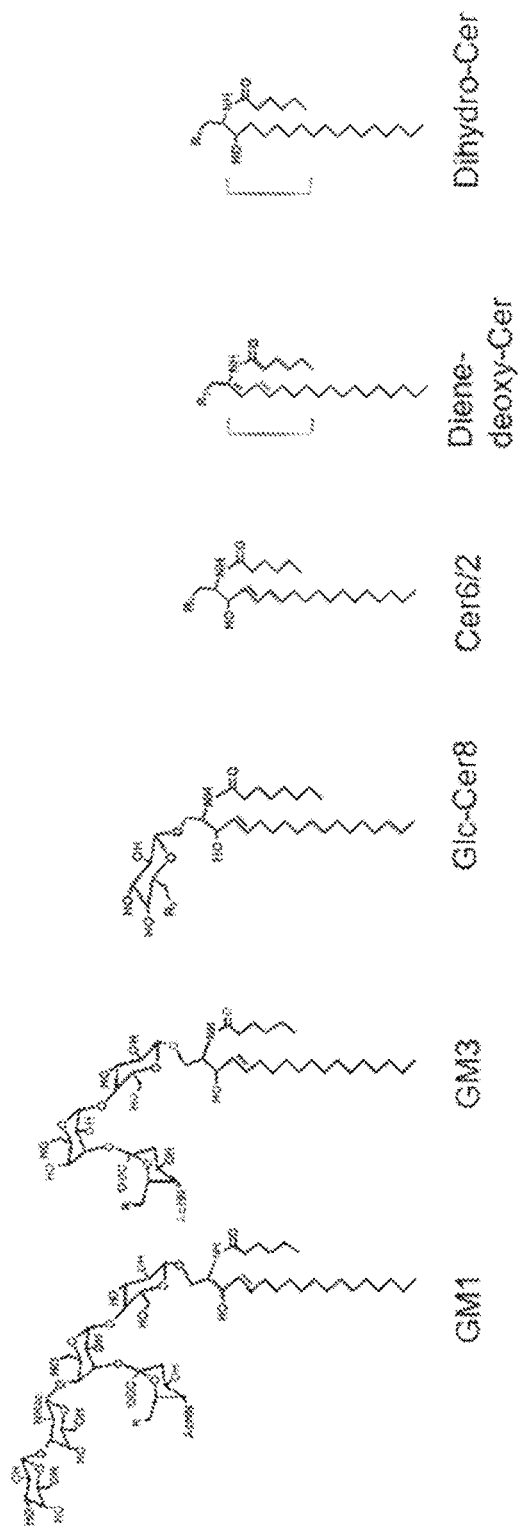
FIG. 27 shows the structure of a panel of ceramides and ceramide analogs (Diene-deoxy-Cer and Dihydro-Cer.
Figure 28:
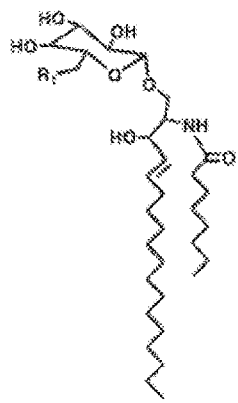
FIG. 28 shows transcytosis of Glc-Cer-C8 and Cer-C6 across MDCKII cells. Efficiency of transcytosis is greater than for peptides fused to GM1 or GM3 species
Figure 28:
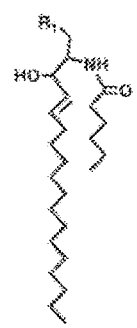
Figure 28:
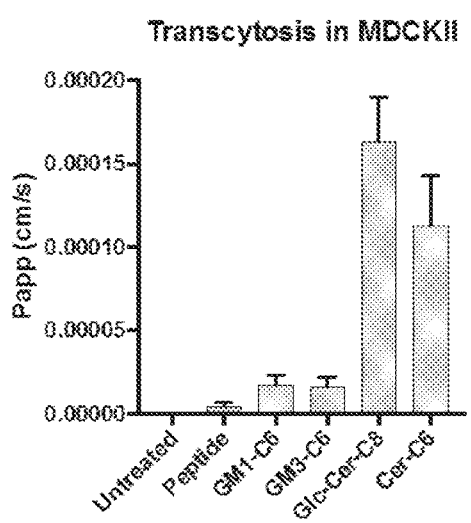
Figure 28:
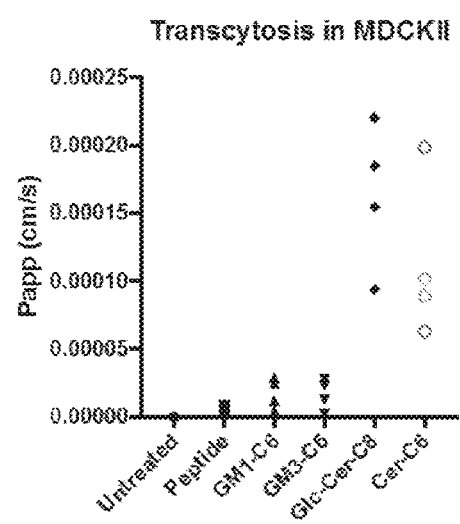
Figure 29:
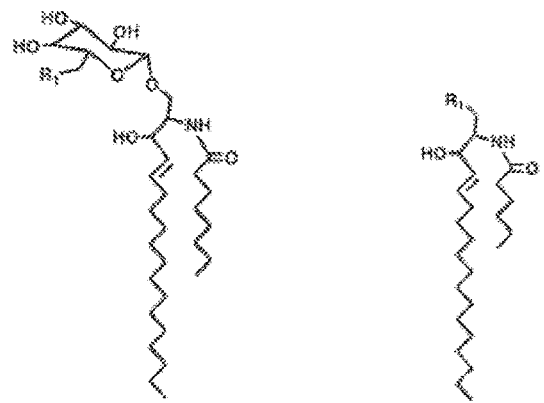
FIG. 29 shows transcytosis of Glc-Cer-C8 and Cer-C6 across T84 intestinal cells. Efficiency of transcytosis is greater than for peptides fused to GM1 or GM3 species
Figure 29:
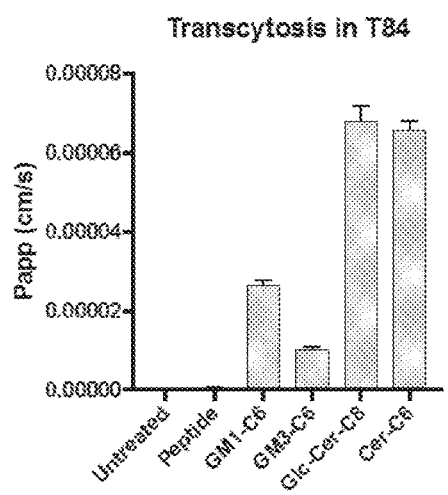
Figure 29:
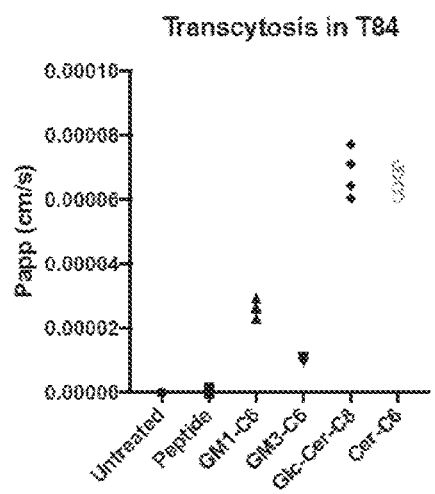

A panel of ceramides and ceramide analogs were synthesized (FIG. 27). Transcytosis of the ceramides and ceramide analogs in MDCKII cells was evaluated, and the apparent permeability coefficient (Papp) values are shown in FIG. 28. Transcytosis of the ceramides and ceramide analogs in T84 intestinal cells was also evaluated, and the apparent permeability coefficient (Papp) values are shown in FIG. 29. The result shows that glycoceramide and ceramide alone are functional as delivery platforms and exhibited even more efficient than GM1.

Figure 30:
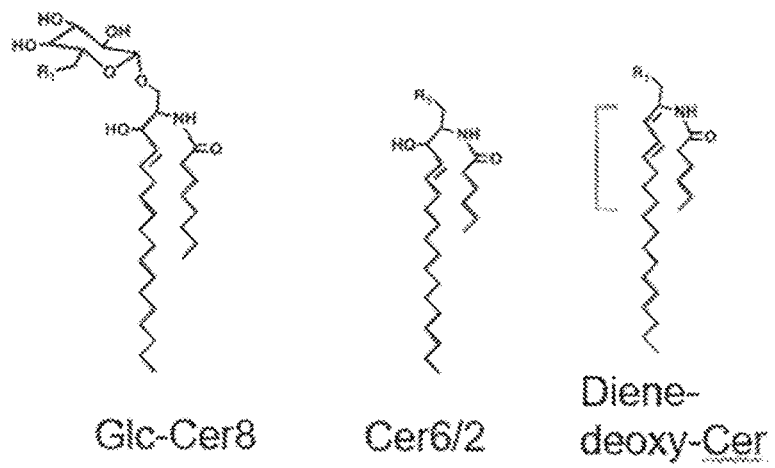
FIG. 30 shows transcytosis of peptides fused to ceramide-like molecules. They are as efficient as the ceramide-alone vehicles. FIG. also shows that low temperature (4° C.) blocks transport of the indicated ceramides or ceramide analogs across the MDCKII cell layer, indicating that the transportation is via transcytosis.
Figure 30:
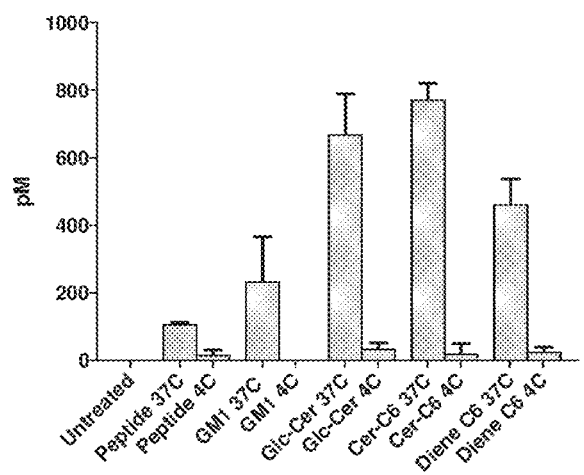

Cer-C6 was tested along with a 4° C. temperature block to demonstrate evidence for the mechanism of transport by transcytosis. The ceramide analog Diene C6 along (structure shown in FIG. 27) was also tested in the same experiment. The results show that the low temperature reduced the uptake of Cer-C6 and the Diene C6 ceramide analog by MDCK H cells, indicating that the transport was via transcytosis with a 4° C. temperature block (FIG. 30). This experiment was repeated with ceramides of different fatty acid chain length (C4, C6. C8 (C8 results not shown)), and with or without a sugar moiety. The results show that ceramide Cer-C6:0 carrier (without sugar) and the ceramide analog diene carrier (C6:0) is effective in transporting across the MDCKII cells via transcytosis, with the Cer-C6:0 being more effective. The glucoceramide C8:0 carriers also effectively transported via transcytosis (data now shown).

Figure 31:
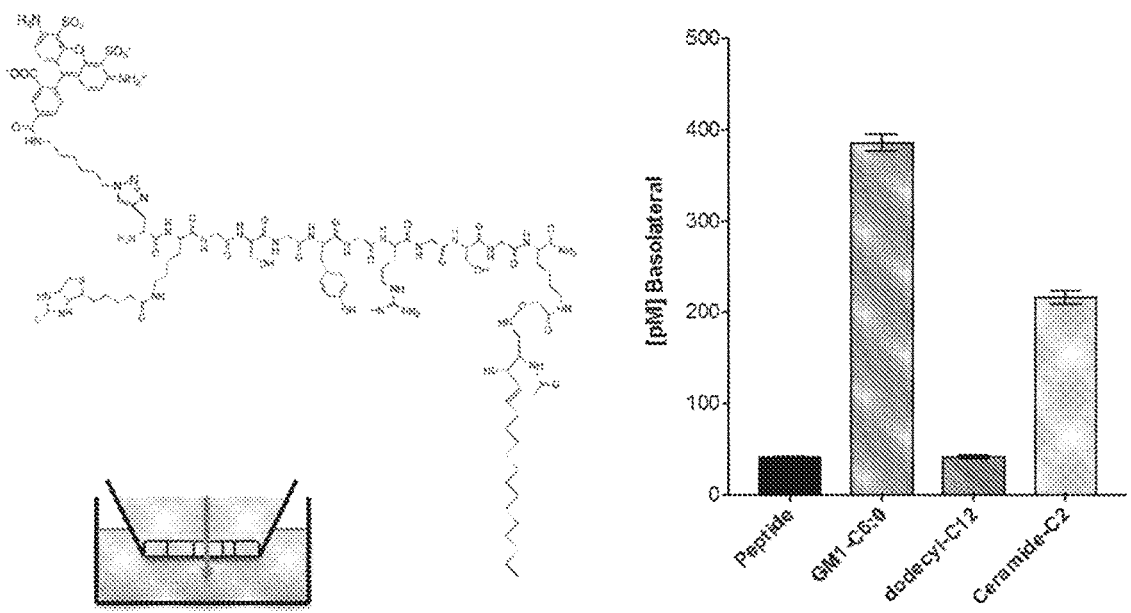
FIG. 31 shows that peptide fused to ceramide-C2, transports across MDCK monolayer. Peptide fusion to a C12 fatty acid alone, did not transport across MDCK cells by transcytosis.

Next, a ceramide with a C2 fatty acid chain and without a sugar moiety (Cer-C2) was tested. Peptide fused to Cer-C2 was able to transport across monolayers of MDCKI cells in a transcytosis assay (FIG. 31). The GM1-C6:0 molecule was used as a positive control, and a peptide fused to a fatty acid dodecyl-C12 was used as a negative control. Dodecyl-C12 did not enable transport across MDCKII cells by transcytosis (FIG. 31).

Figure 33:
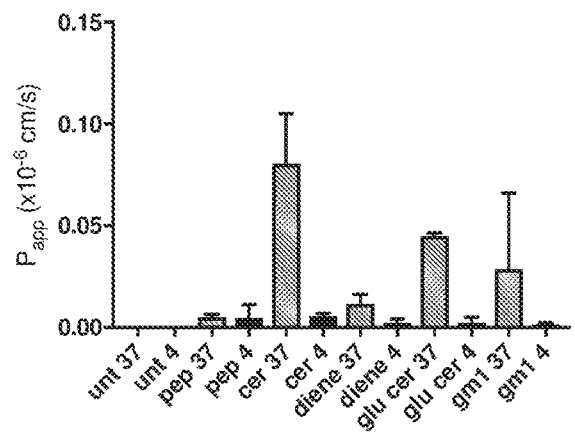
FIG. 33 shows that several ceramides or ceramide analogs can transport across MDCK cells and the transport is via transcytosis.
Figure 34:
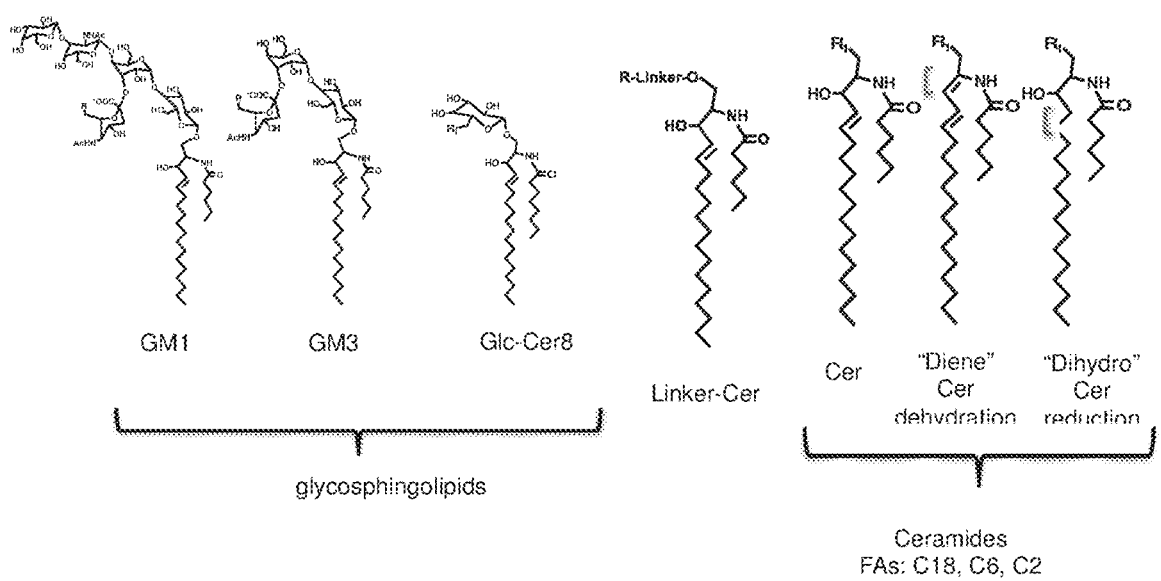
FIG. 34 shows the structures of a panel of glycosphingolipids, ceramides or ceramide analogs to be conjugated to cargos.

A repeat experiment of transcytosis in MDCK cells is shown in FIG. 33. Papp at 37° C. was paired with 4° C. to test for transport by transcytosis (and not paracellular leak). Another independent experiment that shows the ceramide alone Cer-C6:0 carrier is effective. The ceramide-like diene carrier (C6:0) also works, but is less effective compared to the ceramide-C6:0 species. The glucoceramide C8:0 carriers also work and are probably as effective as ceramide C6:0 alone. Both are more effective than the original fusion molecules using GM1 C6:0.

Figure 38:
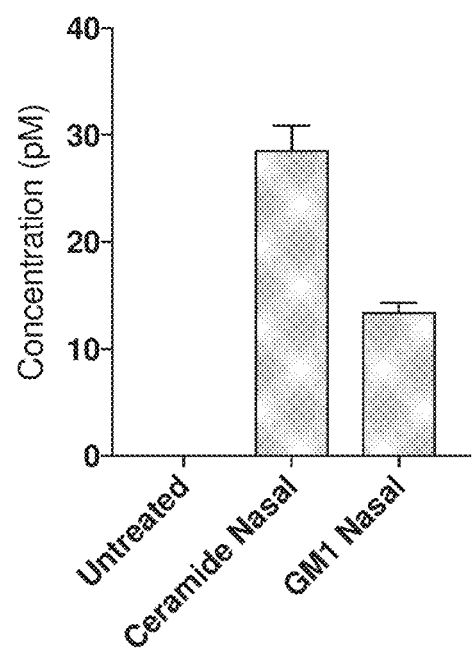
FIG. 38 shows that ceramide C6 (Cer0C6) is absorbed via the nose in mice 15 minutes after dosing.

Further, whether a ceramide can be absorbed via the nose is tested. A reporter peptide was conjugated to a ceramide-C6 (Cer-C6) was administered to C57BL/6J mice (n=1, from Jackson Labs) at a dose of 2 nmol/kg. GM1-C6 conjugated to the same reported peptide was used as control. A total of 5 µl per nostril was administered over 5 minutes under isoflurane. Blood was collected via cardiac puncture 15 minutes post dose and the amount of the conjugate was evaluated by pulling down with magnetic streptavidin beads followed by elution and plate fluorescence measurement. The data showed that ceramide-C6-reporter peptide conjugate can be absorbed via nose in mice, and that the peptide conjugated to Cer-C6 is absorbed more efficiently than peptide conjugated to GM1-C6 (FIG. 38).

Figure 35:
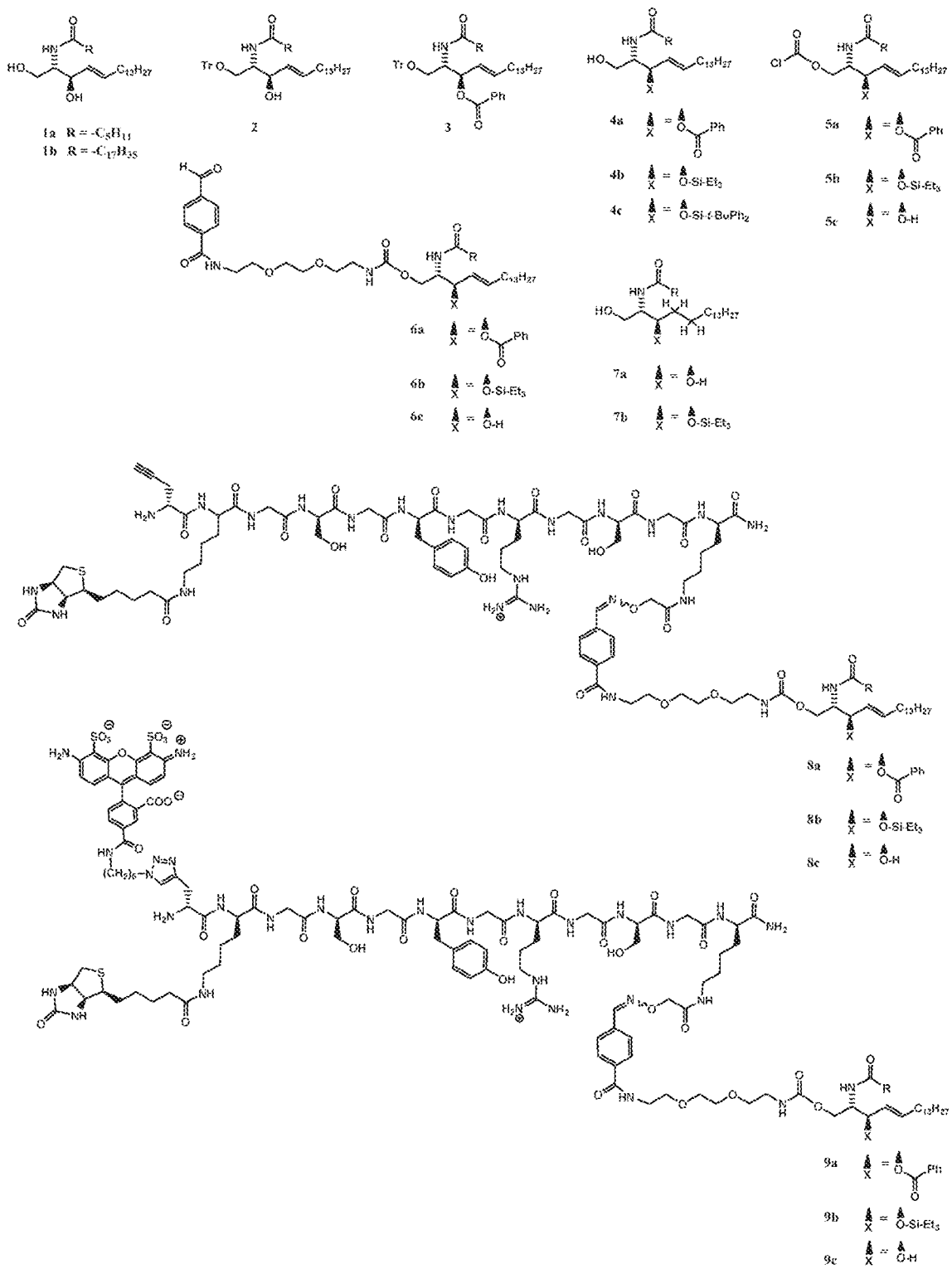
FIG. 35 shows ceramides, linker-ceramides, LC9-linker ceramides, and AF488-LC9-linker ceramides that were tested.
Figure 36:
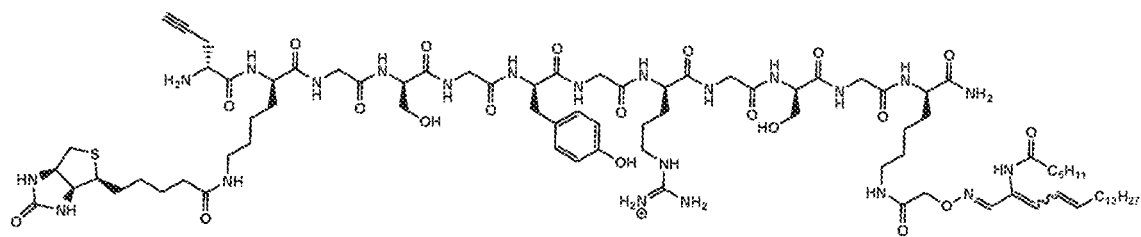
FIG. 36 shows LC9 oximes.
Figure 36:
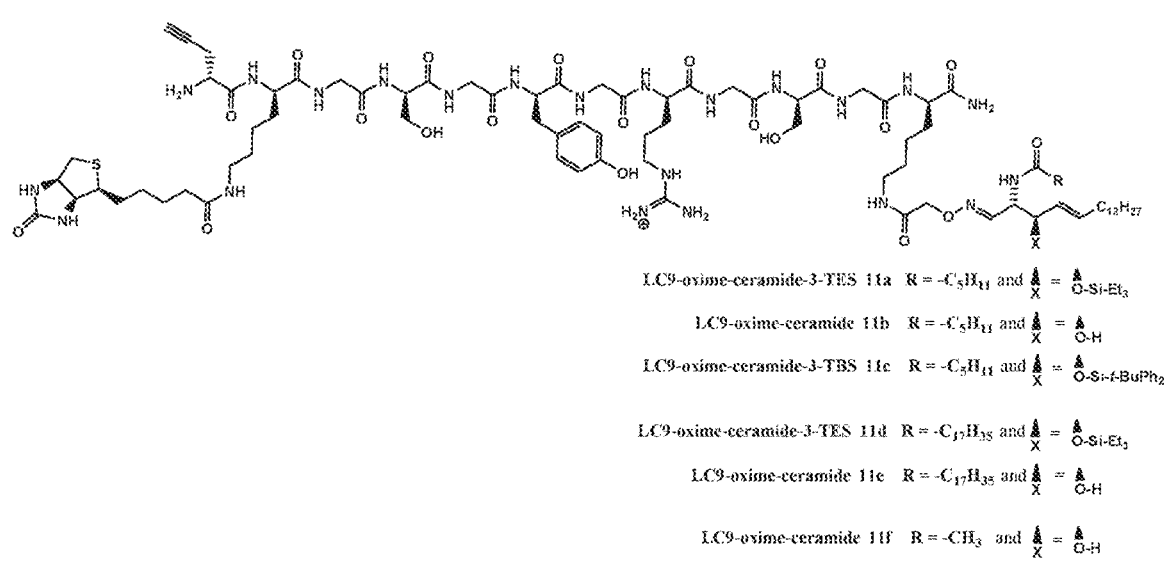
Figure 36:
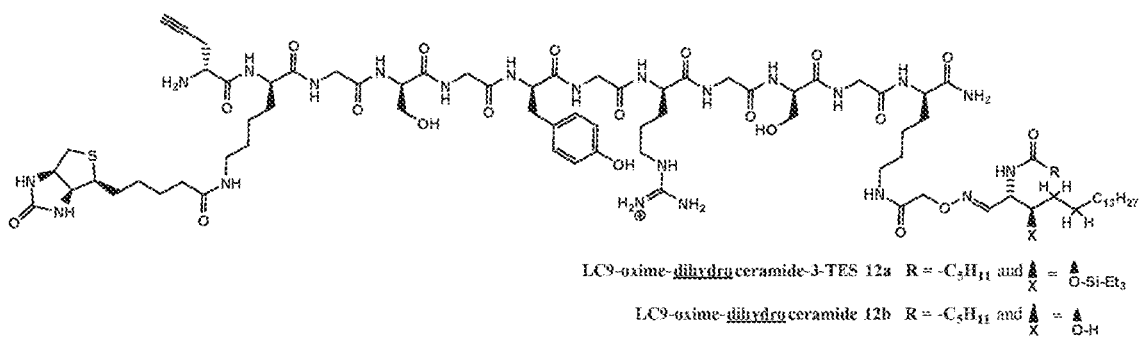

Example 6. Synthesis of Peptide-Ceramide Conjugates as a Platform for Protein Drug Delivery Diene-analogs (due to dehydration) and dihydro-analogs of ceramide have been underlined for clarity in this disclosure. Oximes may be a mix of cis and trans geometric isomers. Oximes have been arbitrarily drawn as cis-isomers in FIG. 35 and as trans-isomers (likely the predominant isomer) in FIG. 36 and FIG. 37. Some oximes have been reduced to the corresponding O-alkylhydroxylamine analogs. (Data not shown). Reactions were run in Wheaton vials with triangular magnets unless otherwise stated. Chromatography on flash silica gel 60 (230-400 mesh) at 35° C. unless otherwise stated. Analytical thin layer chromatography (TLC) utilized silica gel 60 on glass plates that were visualized by UV 254, and by phosphoric acid charring on a hot plate at 240° C. HPLC purifications on RP-C3 columns eluting with acetonitrile/water containing 0.1% formic acid. Mass Spectral data from an Agilent Technologies 6120 quadripole LC-MS.

Linker Chemistry and "diene"-analog of ceramide (dehydration compound) (2S,3R,4E)-1-(O-Triphenylmethyl)-2-(N-hexanoylamino)-4-octadecene-1,3-diol [1-trityl-C6-ceramide 2 (R=—$C_5H_{11}$)]. To a vigorously stirred solution of C6-ceramide 1 (R=—$C_5H_{11}$) (30.3 mg, 7.62×$10^{-5}$ mol), ethyldiisopropylamine (18 µL, 13 mg, 1.0×$10^{-4}$ mol), and DMAP (1.1 mg, 9.0×$10^{-6}$ mol) in 500 µL of dry $CH_2Cl_2$, was added trityl chloride (23.4 mg, 8.4×$10^5$ mol) in 200 µL of $CH_2Cl_2$ at mom temperature over 5 min. The reaction mixture was stirred for 3 days. The mixture was concentrated and chromatographed to give 1-trityl-C6-ceramide 2 (R=—$C5H_{11}$) (32.0 mg, 5.00×$10^5$ mol, 66%) as a clear and colorless viscous liquid that was homogeneous by TLC (90:10:0.1 $CHCl_3$/EtOAc/TEA $R_f$ 0.42): $^1$H NMR (DMSO-$d_6$).

(2S,3R,4E)-3-O-Benzoyl-1-(O-triphenylmethyl)-2-(N-hexanoylamino)-4-octadecene-1,3-diol [1-trityl-3-benzoyl-C6-ceramide 3 (R=—$C_5H_{11}$)]. To a vigorously stirred solution of 1-trityl-C6-ceramide 2 (R=—$C_5H_{11}$) (9.5 mg, 1.5× $10^5$ mol), ethyldiisopropylamine (13.1 µL, 9.7 mg, 7.5×$10^5$ mol, 500 mol %), and catalytic DMAP in 500 µL of dry toluene, was added benzoyl chloride (2.5 mg, 1.8×$10^5$ mol). After 1 day, additional ethyldiisopropylamine (13.1 µL) and benzoyl chloride (2.5 mg) were added. The reaction was filtered through a plug of 0.2 g silica gel eluting with $CHCl_3$/EtOAc/TEA (97:3:0.1 $CHCl_3$/EtOAc/TEA). The filtrate containing product was chromatographed (97:3:0.1 $CHCl_3$/EtOAc/TEA) to give 1-trityl-3-benzoyl-C6-ceramide 3 (R=—$C_5H_{11}$) (10.0 mg, 1.34×$10^{-5}$ mol, 89%) as a clear and colorless viscous liquid that was homogeneous by TLC (97:3:0.1 $CHCl_3$/EtOAc/TEA $R_f$ 0.45): $^1$H NMR (DMSO-$d_6$).

(2S,3R,4E)-3-O-Benzoyl-2-(N-hexanoylamino)-4-octadecene-1,3-diol [3-benzoyl-C6-ceramide 4a (R=—$C_5H_{11}$)]. To a stirred solution of 1-trityl-3-benzoyl-C6-ceramide 3 (R=—$C_{51}Hu$) (10. mg, 1.3×$10^5$ mol) in 2 mL of $CH_2Cl_2$MeOH (1:1) was added a solution of p-toluenesulfonic acid monohydrate 13.8 mg, 2.0×10 mol) in 0.5 mL of MeOH. After 3 days. $CH_2Cl_2$ was added and the solution washed twice with 1 mL portions of 8.5 mg/mL aqueous $NaHCO_3$. The organic phase was then washed with $H_2O$, dried over $Na_2SO_4$, and chromatographed (96:4 $CH_2Cl_2$MeOH) to give 3-benzoyl-C6-ceramide 4a (R=—$C_5H_{11}$) (6.5 mg, 1.3×$10^{-5}$ mol, 100%) as a white solid that was nearly homogeneous by TLC (96:4 $CH_2Cl_2$/MeOH, $R_f$ 0.20): $^1$H NMR (DMSO-$d_6$): mass spectrum $C_{37}H_{52}NO_4^+$: m/z calculated 502.4, observed 502.5.

Linker (2S,3R,4E)-3-O-Benzoyl-1-O— (2-(2-(2-(4-formylbenzamido)ethoxy)ethoxy)ethan-1-carbamoyl)-2-(N-hexanoylamino)-4-octadecene-1,3-diol [1-(Ald-PEG2-carbamoyl)-C6-ceramide-3-benzoate 6a (R=—$C_5H_{11}$)]. To a stirred solution of triphosgene (5.9 mg, 2.0×$10^5$ mol, 20 eq) in 0.2 mL of anhydrous $CH_2C2$ was added dropwise over 2 min a solution of 3-benzoyl-C6-ceramide 4a (R=—$C_5H_{11}$) (1.5 mg, 3.0×$10^5$ mol, 1 eq) in 0.2 mL of anhydrous $CH_2C12$ containing ethyldiisopropylamine (22 µL, 16 mg, 3.0×$10^{-5}$ mol, 43 eq). After 2 h, the reaction mixture was distilled using a stream of nitrogen gas blowing over the reaction mixture and out through a solution of aqueous ammonium hydroxide/$H_2O$/i-PrOH (1:1:1). The residue was redissolved in 0.1 mL of anhydrous $CH_2Cl_2$ to give a light yellow solution. To this solution of crude chloroformate 5a (R=—$C_5H_{11}$) was added rapidly dropwise a freshly prepared solution of Ald-PEG2-ammonium trifluoracetate (3.9 mg, 9.9×$10^{-6}$ mol, 3.3 eq. Broadpharm, CAS 2055013-56-2) in 0.1 mL of dry $CH_2C12$ containing ethyldiisopropylamine (12 µL, 8.9 mg, 6.9×$10^5$ mol, 7 eq). After 1 h 15 min, the solvent was removed to give a yellow semi-solid that was chromatographed (96:4:0.1 $CHCl_3$/EtOAc/TEA) to give a nearly quantitative yield of 1-(Ald-PEG2-carbamoyl)-C6-ceramide-3-benzoate 6a (R=—$C_5H_{11}$) as a faint yellow semisolid that was nearly homogeneous by TLC (96:4:0.1 $CHCl_3$/EtOAc/TEA. $R_f$ 0.18): $^1$H NMR (DMSO-$d_6$).

Linker

The linker already has aldehyde function.

Coupling with LC9 to Give the Oxime

LC9-oxime-PEG2-carbamoyl-C6-ceramide-3-benzoate 8a (R=—$C_5H_{11}$). To a solution of 1-(Ald-PEG2-carbamoyl)-C6-ceramide-3-benzoate 6a (R=—$C_5H_{11}$) (1.5 mg, $1.9 \times 10^{-6}$ mol) and LC9 (2.7 mg, $1.9 \times 10^{-6}$ mol) in 800 µL of DMF was added 1 µL of aniline and the reaction stirred overnight. HPLC purification of the reaction mixture gave LC9-oxime-PEG2-carbamoyl-C6-ceramide-3-benzoate 8a (R=—$C_5H_{11}$); mass spectrum $C_{106}H_{163}N_{24}O_4S^+$: m/z calculated for $(M+2H)^{+2}$ 1118.6, observed 1118.9.

Figure 37:
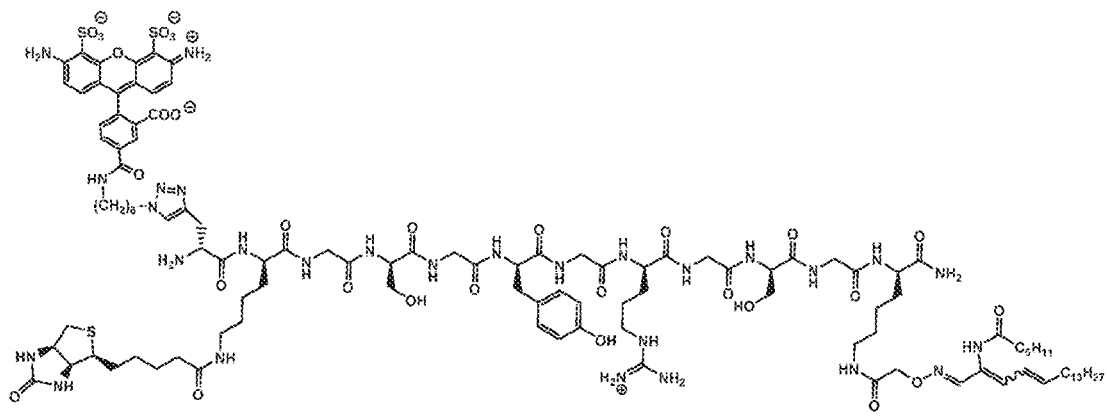
FIG. 37 shows AF488-LC9 oximes.
Figure 37:
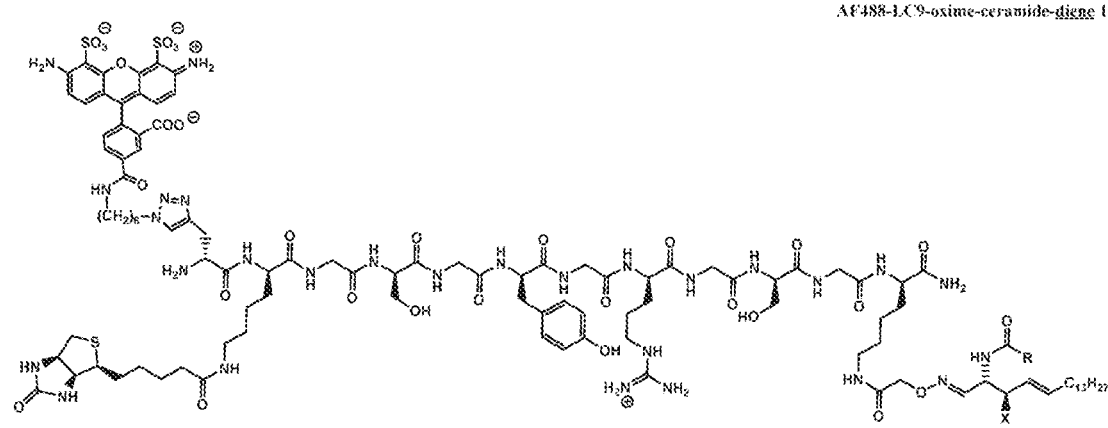
Figure 37:
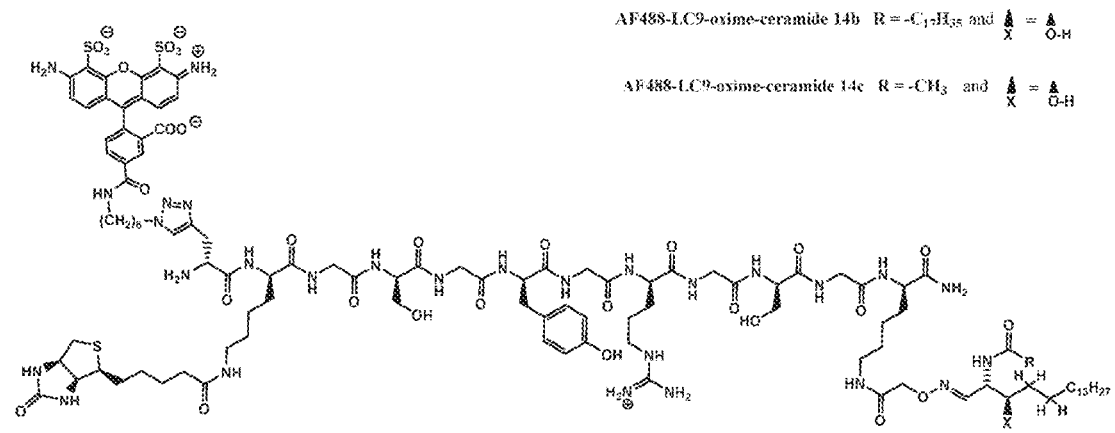

The "click" reaction with AF488-azide which is a copper (I)-catalyzed azide-alkyne cycloaddition (CuAAC Reaction) to give the corresponding predominantly 1,4-substituted-1,2,3-triazole (as drawn in FIG. 37, though may contain some 1.5-substituted triazole). AF488-LC9-oxime-PEG2-carbamoyl-C6-ceramide-3 benzoate 9a (R=—$C_5H_{11}$), mass spectrum m/z calculated for $(M+2H)^{+2}$, observed.

Diene

Oxidation of Primary Alcohol to Aldehyde

To a solution of C6-ceramide-3-benzoate 4a (R=—$C_5H_{11}$) (1 mg, $2 \times 10^{-6}$ mol) in 0.2 mL of dry $CH_2Cl_2$, was added a 0.30 M solution of Dess-Martin periodinane (13 µL, $4 \times 10^{-6}$ mol) dropwise over 1 min during which time the solution remained homogeneous. After 10 min, a vortex-mixed solution of $H_2O$ (0.04 µL, 0.04 mg, $2 \times 10^{-6}$ mol) in 40 µL of $CH_2Cl_2$ was added dropwise over 10 min during which time the reaction mixture became cloudy. The reaction mixture was vigorously stirred for an additional 1.5 h. The reaction mixture was then washed with 0.2 mL of 1:1 saturated aqueous $NaHCO_3$/15% $Na_2S_2O_3$, dried over $Na_2SO_4$, filtered through a 0.45 µm GHP filtration cartridge, and the solvent removed to give a light yellow viscous oil that contained the corresponding aldehyde by TLC (90:10:0.1 $CHCl_3$/EtOAc/TEA. $R_f$ 0.66) and was used immediately.

Diene

Coupling with LC9 to Give the Oxime

LC9-oxime-C6-ceramide-diene 10 (R=—$C_5H_{11}$). To a solution of the crude aldehyde (0.5 mg, $1 \times 10^{-6}$ mol) and LC9 (1.7 mg, $1.2 \times 10^{-6}$ mol) in 1 mL of DMF was added 1 µL of aniline and the reaction stirred overnight. HPLC purification of the reaction mixture gave LC9-oxime-C6-ceramide-diene analog 10 (R=—$C_5H_{11}$) (0.4 mg, $2 \times 10^{-7}$ mol): mass spectrum $C_{84}H_{137}N_{22}O_{20}S^+$: m/z calculated for $(M+2H)^{+2}$ 903.5, observed 903.8, calculated for $(M+3H)^{+3}$ 602.7, observed 603.1.

Diene

The "click" reaction with AF488-azide which is a copper (I)-catalyzed azide-alkyne cycloaddition (CuAAC Reaction) to give the corresponding predominantly 1,4-substituted-1,2,3-triazole (as drawn in FIG. 37, though may contain some 1.5-substituted triazole). AF488-LC9-oxime-C6-ceramide-diene analog 13 (R=—$C_5H_{11}$). A solution of LC9-oxime-C6-ceramide-diene analog 10 (R=—$C_5H_{11}$) (0.4 mg, $2 \times 10^{-7}$ mol). Alexa Fluor® 488 (0.38 mg, $4.4 \times 10^{-7}$ mol), tris[(1-benzyl-1H-1,2,3-triazol-4-yl)methyl]amine ($6 \times 10^{-6}$ mol), tris(2-carboxyethyl)phosphine ($1 \times 10^{-6}$ mol), ascorbic acid ($1 \times 10^4$ mol). Cu(II)$SO_4$ ($5 \times 10^{-6}$ mol), in 1 mL of 8:2 DMSO/Tris buffer pH 8, was stirred overnight protecting from light. The reaction mixture was centrifuged, and the colored precipitate was purified by HPLC to give AF488-LC9-oxime-C6-ceramide-diene analog 13 (R=—$C_5H_{11}$) (14 µg, $5.7 \times 10^{-9}$ mol, 2.8% yield); mass spectrum $C_{111}H_{163}N28O_{30}S_3^+$: m/z calculated for $(M+2H)^{+2}$ 1232.6, observed 1232.5, calculated for $(M+3H)+^3$ 822.1, observed 822.2.

AF488-LC9-Oxime-C6 Ceramide

C6

(2S,3R,4E)-3-O-Triethylsilyl-2-(N-hexanoylamino)-4-octadecene-1,3-diol [3-TES-C6-ceramide 4b (R=—$C_5H_{11}$)]. To a stirred solution of C6-ceramide 1 (R=—$C_5H$ a) (30.3 mg, $7.62 \times 10^{-5}$ mol), ethyldiisopropylamine (150 µL, 111 mg, $8.5 \times 10^4$ mol), and DMAP (9.5 mg, $7.8 \times 10^{-5}$ mol) in 1.5 mL of dry $CH_2Cl_2$, was added triethylsilyl chloride (12 µL, 11 mg, $7.3 \times 10^{-5}$ mol) dropwise at room temperature over 2 min. The reaction mixture was stirred for 1.5 h. The mixture was concentrated and chromatographed (90:10:0.1 $CHCl_3$/EtOAc/TEA) first eluting 1,3-diTES-C6-ceramide R=—$C_5H_{11}$) followed by 1-TES-C6-ceramide (R=—$C_5H_{11}$), then the desired 3-TES-C6-ceramide 4b (R=—$C_5H_{11}$) as the minor product (3.7 mg, $7.2 \times 10^{-6}$ mol, 9.4%) as a clear and colorless viscous liquid that was homogeneous by TLC (90:10:0.1 $CHCl_3$/EtOAc/TEA $R_f$ 0.15): $^1H$ NMR (DMSO-$d_6$); mass spectrum $C_{30}H_{62}NO_3Si^+$: m/z calculated 512.5, observed 512.4.

C6

Step One is oxidation of primary alcohol to aldehyde. To a solution of C6-ceramide-3-TES 4b (R=—$C_5H_{11}$) (2.2 mg, $4.3 \times 10^{-6}$ mol) in 0.2 mL of dry $CH_2C_2$, was added a 0.30 M solution of Dess-Martin periodinane (22 µL, $5.7 \times 10^{-6}$ mol, 1.5 eq) dropwise over 1 min during which time the solution remained homogeneous. After 10 min, a vortex-mixed solution of $H_2O$ (0.13 µL, 0.13 mg, $7.2 \times 10^{-6}$ mol) in 130 µL of $CH_2Cl_2$ was added dropwise over 10 min during which time the reaction mixture became cloudy. The reaction mixture was vigorously stirred for an additional 15 min. The reaction mixture was then washed with 0.2 mL of 1:1 saturated aqueous $NaHCO_3$/15% $Na_2S203$, dried over $Na_2SO_4$, filtered through a 0.45 µm GHP filtration cartridge, and the solvent removed to give a light yellow viscous oil that contained the corresponding aldehyde by TLC (90:10:0.1 CHCb3/EtOAc/TEA, $R_f$ 0.62) and was used immediately.

C6

Step Two is the coupling with LC9 to give the oxime. LC9-oxime-C6-ceramide-3-TES 11a (R=—$C_5H_{11}$). To a solution of the crude aldehyde (2 mg, $4 \times 10^{-6}$ mol) and LC9 (6.2 mg, $4.3 \times 10^{-6}$ mol) in 1 mL of DMF was added 1 µL of aniline and the reaction stirred overnight. HPLC purification of the reaction mixture gave LC9-oxime-C6-ceramide-3-TES 11a (R=—$C_5H_{11}$); mass spectrum $C_{90}H_{153}N_{22}O_{21}SSi^+$: m/z calculated for $(M+2H)^{+2}$ 969.6, observed 970.5, calculated for $(M+3H)*^3$ 646.7, observed 647.2.

C6

Step Three is removal of the TES, LC9-oxime-C6-ceramide 11b (R=—$C_5H_{11}$). A solution of LC9-oxime-C6- ceramide-3-TES 11a (R=—C$_5$H$_{11}$) in 80:20 acetic acid/ H$_2$O was stirred for two hours. Solvents were removed by lyophilization. HPLC purification of the reaction mixture gave LC9-oxime-C6-ceramide 11b (R=—C$_5$H$_{11}$) (1.0 mg, 5.5×10$^{-7}$ mol); mass spectrum C$_{84}$H$_{139}$N$_{22}$O$_{21}$S$^+$: m/z calculated for (M+2H)$^{+2}$ 912.5, observed 912.7, calculated for (M+3H)$^{+3}$ 608.7, observed 609.1.

C6

Step Four is the "click" reaction with AF488-azide which is a copper(I)-catalyzed azide-alkyne cycloaddition (CuAAC Reaction) to give the corresponding predominantly 1,4-substituted-1,2,3-triazole (as drawn in FIG. 37, though may contain some 1,5-substituted triazole).

AF488-LC9-oxime-C6-ceramide 14b (R=—CH$_5$H$_{11}$). A solution of LC9-oxime-C$_6$-ceramide 11b (R=—C$_5$H$_{11}$) (1.0 mg, 5.5×10$^{-7}$ mol), Alexa Fluor® 488 (0.71 mg, 8.2×10$^{-7}$ mol), tris[(1-benzyl-1H-1,2,3-triazol-4-yl)methyl]amine 16×10$^{-8}$ mol), tris(2-carboxyethyl)phosphine (1×10$^{-6}$ mol), ascorbic acid (1×10$^{-4}$ mol), Cu(II)SO$_4$ (5×10$^{-6}$ mol), in 1 mL of 8:2 DMSO/Tris buffer pH 8, was stirred overnight protected from light. The reaction mixture was centrifuged, and the colored precipitate was purified by HPLC to give AF488-LC9-oxime-C6-ceramide 14a (R=—C$_5$H$_{11}$) (100 □g, 6.2×10$^{-8}$ mol), mass spectrum Cu$_{111}$H$_{165}$N$_{28}$O$_{31}$S$_3^+$: m/z calculated for (M+2H)$^{+2}$ 1241.1, observed 1241.6, calculated for (M+3H)+$^3$ 827.7, observed 828.2.

AF488-LC9-Oxime-C18 Ceramide

C18

(2S,3R,4E)-3-O-Triethylsilyl-2-(N-octadecanoylamino)-4-octadecene-1,3-diol [3-TES-C18-ceramide 4b (R=—C$_{17}$H$_{35}$)]. To a stirred solution of C18-ceramide 1 (R=—C$_{17}$H$_{35}$) (41.2 mg, 7.28×10$^{-5}$ mol), ethyldiisopropylamine (150 µL, 111 mg, 8.5×10$^{-4}$ mol), and DMAP (12.7 mg, 1.04×10 mol) in 1.5 mL of dry CH$_2$Cl$_2$, was added triethylsilyl chloride (14 µL, 13 mg, 8.6×10$^{-5}$ mol) dropwise at room temperature over 2 min. The reaction mixture was stirred for 1.5 h. The mixture was concentrated and chromatographed (90:10:0.1 CHCl$_3$/EtOAc/TEA) first eluting 1,3-diTES-C18-ceramide R=—C$_{17}$H$_{35}$) followed by 1-TES-C$_{18}$-ceramide (R=—C$_{17}$H$_{35}$), then the desired 3-TES-C18-ceramide 4b (R=—C$_{17}$H$_{35}$) as the minor product (2.5 mg, 3.7×10$^{-6}$ mol, 5.1%) as an amorphous white solid that was homogeneous by TLC (90:10:0.1 CHCl$_3$/EtOAc/TEA R$_f$ 0.15): $^1$H NMR (DMSO-d$_6$).

C18

Step One is oxidation of primary alcohol to aldehyde. To a solution of 3-TES-C18-ceramide 4b (R=—C$_{17}$H$_{35}$) (2.5 mg, 3.7×10$^{-6}$ mol) in 0.2 mL of dry CH$_2$Cl$_2$, was added a 0.30 M solution of Dess-Martin periodinane (19 µL, 5.7×10$^{-6}$ mol, 1.5 eq) dropwise over 1 min during which time the solution became cloudy. After 10 min, a vortex mixed solution of H$_2$O (0.11 µL, 0.11 mg, 6.1×10$^{-6}$ mol) in 110 µL of CH$_2$Cl$_2$ was added dropwise over 10 min. The reaction mixture was vigorously stirred for an additional 15 min. The reaction mixture was then washed with 0.2 mL of 1:1 saturated aqueous NaHCO$_3$/15% Na$_2$S$_2$O$_3$, dried over Na$_2$SO$_4$, filtered through a 0.45 µm GHP filtration cartridge, and the solvent removed to give yellow viscous oil that was highly homogeneous aldehyde by TLC (90:10:0.1 CHCl$_3$/EtOAc/TEA. R$_f$ 0.59) and was used immediately.

C18

Step Two is the coupling with LC9 to give the oxine with protecting group removal. LC9-oxime-C18-ceramide 11e (R=—C$_{17}$H$_{35}$). To a solution of the crude aldehyde (2.5 mg, 3.7×10$^{-6}$ mol) and LC9 (5.3 mg, 3.7×10$^{-6}$ mol) in 1 mL of DMF was added 1 µL of aniline and the reaction stirred overnight. HPLC purification of the reaction mixture gave only a small amount of LC9-oxime-C18-ceramide-3-TES 11d (R=—C$_{17}$H$_{35}$), but most of the TES had fallen off and gave LC9-oxime-C18-ceramide 11e (R=—C$_{17}$H$_{35}$) (3.9 mg, 2.0×10$^{-6}$ mol, 54% yield) as a white solid: $^1$H NMR (DMSO-d$_6$): mass spectrum C$_{96}$H$_{163}$N$_{22}$O$_{21}$S$^+$: m/z calculated for (M+2H)$^{+2}$ 996.6, observed 996.9, calculated for (M+3H)$^{+3}$ 664.7, observed 665.1.

C18

Finally, the "click" reaction with AF488-azide which is a copper(I)-catalyzed azide-alkyne cycloaddition (CuAAC Reaction) to give the corresponding predominantly 1,4-substituted-1,2,3-triazole (as drawn in FIG. 37, though may contain some 1.5-substituted triazole).

AF488-LC9-oxime-C18-ceramide 14b (R=—C$_{17}$H$_{35}$). A solution of LC9-oxime-C18-ceramide 11e (R=—C$_{17}$H$_{35}$) (0.64 mg, 5.5×10$^{-4}$ mol). Alexa Fluor® 488 (0.71 mg, 4.9×10$^7$ mol), tris[(1-benzyl-1H-1,2,3-triazol-4-yl)methyl]amine (6×10$^{-8}$ mol), tris(2-carboxyethyl)phosphine (1×10$^{-4}$ mol), ascorbic acid (1×10$^{-4}$ mol), Cu(II)SO$_4$ (5×10$^{-6}$ mol), in 1 mL of 8:2 DMSO/Tris buffer pH 8, was stirred overnight protected from light. The reaction mixture was centrifuged, and the colored precipitate purified by HPLC to give AF488-LC9-oxime-C18-ceramide 14b (R=—C$_{17}$H$_{35}$); mass spectrum C$_{123}$H$_{189}$N$_{28}$O$_{31}$S$_3^+$: m/z calculated for (M+2H)$^{+2}$ 1325.7, observed 1325.6, calculated for (M+3H)$^{+3}$ 884.1, observed 884.8.

AF488-LC9-Oxime-Dihydroceramide

Dihydro (2S,3R)-3-O-Triethylsilyl-2-(N-hexanoylamino)-octadecane-1,3-diol [3-TES-C6-dihydroceramide 7b (R=—C$_5$H$_{11}$)]. To a stirred solution of C6-dihydroceramide 7a (R=—C$_5$H$_{11}$) (27.8 mg, 6.96×10$^{-5}$ mol), ethyldiisopropylamine (280 µL, 208 mg, 1.61×10$^{-3}$ mol), and DMAP (12 mg, 9.8×10$^{-5}$ mol) in 1.5 mL of dry CH$_2$Cl$_2$, was added triethylsilyl chloride (14 µL, 13 mg, 8.6×10$^{-5}$ mol) dropwise at room temperature over 2 min. The reaction mixture was stirred for 1.5 h. The mixture was concentrated and chromatographed (90:10:0.1 CHCl/EtOAc/TEA) first eluting 1,3-diTES-C6-dihydroceramide (R=—C$_5$H$_{11}$) followed by 1-TES-C6-dihydroceramide (R=—C$_5$H$_{11}$), then the desired 3-TES-C6-dihydroceramide 7b (R=—C$_5$H$_{11}$) as the minor product 12.7 mg, 5.2×10$^{-6}$ mol, 7.5%) as a white waxy solid that was homogeneous by TLC (90:10:0.1 CHCl/EtOAc/TEA, R$_f$ 0.14): $^1$H NMR (DMSO-d$_6$).

Dihydro

Step One is oxidation of primary alcohol to aldehyde. To a solution of C6-dihydroceramide-3-TES 7b (R=—C$_5$H$_{11}$) (2 mg, 4×10$^{-6}$ mol) in 0.2 mL of dry CH$_2$Cl$_2$, was added a 0.30 M solution of Dess-Martin periodinane (13 µL, 3.9×

$10^{-6}$ mol, 1.5 eq) dropwise over 1 min during which time the solution remained homogeneous. After 10 min, a vortex-mixed solution of $H_2O$ (0.079 μL, 0.079 mg, $4.4 \times 10^{-6}$ mol) in 10 μL of $CH_2Cl_2$ was added dropwise over 10 min during which time the reaction mixture became cloudy. The reaction mixture was vigorously stirred for an additional 30 min. The reaction mixture was then washed with 0.2 mL of 1:1 saturated aqueous $NaHCO_3$/15% $Na_2S_2O_3$, dried over $Na_2SO_4$, filtered through a 0.45 μm GHP filtration cartridge, and the solvent removed to give a light yellow viscous oil that contained the corresponding aldehyde by TLC (90:10: 0.1 $CHCl_3$/EtOAc/TEA. $R_f$ 0.71) and was used immediately.

Dihydro

Step Two is the coupling with LC9 to give the oxime with protecting group removal. LC9-oxime-C6-dihydroceramide 12b (R=—$C_5H_{11}$). To a solution of the crude aldehyde (2 mg, $4 \times 10^{-6}$ mol) and LC9 (5.6 mg, $3.9 \times 10^{-6}$ mol) in 1 mL of DMF was added 1 μL of aniline and the reaction stirred overnight. HPLC purification of the reaction mixture gave only a small amount of protecting group removed LC9-oxime-C6-dihydroceramide 12b (R=—$C_5H_{11}$); mass spectrum $C_{84}H_{141}N_{22}O_{21}S^+$: m/z calculated for $(M+2H)^{+2}$ 913.5, observed 913.7, calculated for $(M+3H)^{+3}$ 609.4, observed 609.7.

All publications, patents, patent applications, publication, and database entries (e.g., sequence database entries) mentioned herein. e.g., in the Background, Summary, Detailed Description, Examples and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a." "an." and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided. URI, addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A delivery vehicle comprising a ceramide and an agent to be delivered, wherein the ceramide comprises a fatty acid of C1-C28; and wherein the agent is attached to the ceramide; wherein the ceramide does not comprise an oligosaccharide; and wherein the agent is not a nucleic acid.

2. The delivery vehicle of claim 1, wherein the ceramide is a ceramide analog.

3. The delivery vehicle of claim 1, wherein the ceramide is a glycoceramide, wherein the sugar of the glycoceramide is a simple sugar.

4. The delivery vehicle of claim 3, wherein the simple sugar is glucose, galactose, fructose, or GalNac.

5. The delivery vehicle of claim 4, wherein the agent to be delivered is attached to the sugar.

6. The delivery vehicle of claim 1, wherein no sugar is attached to the ceramide.

7. The delivery vehicle of claim 6, wherein the agent to be delivered is attached to the primary or secondary hydroxyl group of the ceramide.

8. The delivery vehicle of claim 1, wherein the agent to be delivered is attached to the ceramide via a linker.

9. The delivery vehicle of claim 1, wherein the ceramide comprises a fatty acid of C1-C6.

10. The delivery vehicle of claim 1, wherein the ceramide comprises a fatty acid of C7-C28.

11. The delivery vehicle claim 1, wherein the agent to be delivered is selected from the group consisting of proteins, peptides, polysaccharides and carbohydrates, lipids, glycoproteins, small molecules, synthetic organic and inorganic drugs exerting a biological effect when administered to a subject, and combinations thereof.

12. The delivery vehicle of claim 11, wherein the protein or peptide is an antibody, a ScFv, or a nanobody.

13. The delivery vehicle of claim 1, wherein the agent to be delivered is a therapeutic agent.

14. The delivery vehicle of claim 13, wherein the therapeutic agent is an anti-inflammatory agent, a vaccine antigen, a small molecule drug, an anti-cancer drug or chemotherapeutic drug, a clotting factor, a hormone, a steroid, a cytokine, an antibiotic, an antibody, a ScFv, a nanobody, a vaccine adjuvant, an agent that induces immune tolerance, or a drug for the treatment of a cardiovascular disease, an infectious disease, an autoimmune disease, allergy, a blood disorder, a metabolic disorder, a skin disease, an eye disease, a lysosomal storage disease, or a neurological disease.

15. A method of delivering an agent into a cell, across an epithelial barrier, or across an endothelial barrier, the method comprising contacting a delivery vehicle with the cell, the epithelial barrier, or the endothelial lumenal surface, under conditions appropriate for uptake of the delivery vehicle or the agent into the cell or absorption of the delivery vehicle or the agent across the mucosal surface or the endothelial surface, wherein the delivery vehicle comprises a ceramide and the agent, wherein the ceramide: (a) does not comprise a fatty acid; or (b) comprises a fatty acid of C1-C28; wherein the agent is attached to the ceramide; and wherein the ceramide does not comprise an oligosaccharide.

16. The method of claim 15, wherein the ceramide is a glycoceramide, and wherein the sugar of the glycoceramide is a simple sugar.

17. The method of claim 16, wherein the agent to be delivered is attached to the sugar.

18. The method of claim 15, wherein no sugar is attached to the ceramide.

19. A method of enhancing the half-life of an agent in a subject, the method comprising administering to the subject a delivery vehicle comprising a ceramide and the agent, wherein the ceramide comprises a fatty acid of C1-C28; wherein the agent is attached to the ceramide; and wherein the ceramide does not comprise an oligosaccharide.

20. A method of treating a disease or condition in a subject in need thereof, the method comprising administering to the subject an effective amount of a delivery vehicle comprising a ceramide and an agent to be delivered, wherein the ceramide comprises a fatty acid of C1-C28; wherein the agent is attached to the ceramide; and wherein the ceramide does not comprise an oligosaccharide.

21. A delivery vehicle comprising a ceramide and an agent to be delivered, wherein the ceramide: (a) does not comprise a fatty acid; or (b) comprises a fatty acid of C1-C28; and wherein the agent is attached to the primary hydroxyl or secondary hydroxyl of the ceramide, wherein the ceramide does not comprise an oligosaccharide; and wherein the agent is a protein, a peptide, or nucleic acids.

22. A method of enhancing the half-life of an agent in a subject, the method comprising administering to the subject a delivery vehicle comprising a ceramide and the agent, wherein the ceramide: (a) does not comprises a fatty acid; or (b) comprises a fatty acid of C1-C28; and wherein the agent is attached to the primary hydroxyl or secondary hydroxyl of the ceramide, wherein the ceramide does not comprise an oligosaccharide.

23. A method of treating a disease or condition in a subject in need thereof, the method comprising administering to the subject an effective amount of a delivery vehicle comprising a ceramide and an agent to be delivered, wherein the ceramide: (a) does not comprise a fatty acid; or (b) comprises a fatty acid of C1-C28; and wherein the agent is attached to the primary hydroxyl or secondary hydroxyl of the ceramide, wherein the ceramide does not comprise an oligosaccharide.

* * * * *